(12) United States Patent
Staten et al.

(10) Patent No.: US 6,254,870 B1
(45) Date of Patent: Jul. 3, 2001

(54) THROMBOPOIETIN: IL-3 FUSION PROTEIN

(75) Inventors: Nicholas R. Staten, St. Louis; Jean P. Favara, Ballwin; Larry E. Kahn, St. Louis; Lyle E. Pegg, Ballwin; John P. McKearn, Glencoe, all of MO (US); Charles M. Baum, Evanston, IL (US)

(73) Assignee: G. D. Searle & Co., Chicago, IL (US)

( * ) Notice: Subject to any disclaimer, the term of this patent is extended or adjusted under 35 U.S.C. 154(b) by 0 days.

(21) Appl. No.: 08/875,533

(22) PCT Filed: Feb. 1, 1996

(86) PCT No.: PCT/US96/00830

§ 371 Date: Jan. 30, 1998

§ 102(e) Date: Jan. 30, 1998

(87) PCT Pub. No.: WO96/23888

PCT Pub. Date: Aug. 8, 1996

Related U.S. Application Data

(63) Continuation-in-part of application No. 08/383,035, filed on Feb. 3, 1995, now abandoned.

(51) Int. Cl.⁷ ......................... C12N 15/19; C07K 14/475
(52) U.S. Cl. ..................... 424/192.1; 435/69.7; 530/351; 536/23.1; 424/85.1; 424/85.2; 424/198.1
(58) Field of Search ........................... 530/351; 435/69.7; 536/23.1; 424/85.1, 85.2, 192.1

(56) References Cited

FOREIGN PATENT DOCUMENTS

| 0 668 352 A1 | 2/1995 | (EP) . |
|---|---|---|
| 0 675 201 A1 | 3/1995 | (EP) . |
| 8-168386 * | 7/1996 | (JP) . |
| WO 92/04455 | 8/1991 | (WO) . |
| WO 93/05169 | 8/1992 | (WO) . |
| WO 95/21920 | 8/1994 | (WO) . |
| WO 95/18858 | 12/1994 | (WO) . |
| WO 95/21254 | 2/1995 | (WO) . |

OTHER PUBLICATIONS

Eaton et al, "Platelets and Megakaryocytes–1", Blood, vol. 84, No. 10 Suppl 1., 1994.

Foster et al, "Human thrombopoietin: Gene structure, cDNA sequence, expresion, and chromosomal localization" Proc. Natl. Acad. Sci. USA vol. 91. pp 13023–13027, 1994.

Chang et al, "Coning and Characterization of the Human Megakaryocyte rowth and Development Factor Gene" Jor. Bio. Chem. vol. 270, No. 2 pp. 511–514, 1995.

Metcalf et al, "Thrombopoietin— at last" Nature, vol. 369 pp. 519–520, 1994.

* cited by examiner

Primary Examiner—Lorraine Spector
(74) Attorney, Agent, or Firm—S. Christopher Bauer

(57) ABSTRACT

The present invention relates to variants of human c-mpl ligands (thrombopoietin) with activity on hematopoietic differentiation and expansion.

6 Claims, No Drawings

SEQUENCE LISTING (1) GENERAL INFORMATION:

(iii) NUMBER OF SEQUENCES: 73

(2) INFORMATION FOR SEQ ID NO: 1:

(i) SEQUENCE CHARACTERISTICS:
       (A) LENGTH: 332 amino acids
       (B) TYPE: amino acid
       (C) STRANDEDNESS:
       (D) TOPOLOGY: linear (ii) MOLECULE TYPE: protein (ix) FEATURE:
       (A) NAME/KEY: Modified-site
       (B) LOCATION: 37
       (D) OTHER INFORMATION: /note= "Xaa at position 37 is Thr, Asp, or Glu"

(ix) FEATURE:
       (A) NAME/KEY: Modified-site
       (B) LOCATION: 46
       (D) OTHER INFORMATION: /note= "Xaa at position 46 is Phe, Ala, Val, Leu, Ile, Pro, Trp, or Met"

(ix) FEATURE:
       (A) NAME/KEY: Modified-site
       (B) LOCATION: 47
       (D) OTHER INFORMATION: /note= "Xaa at position 47 is Ser, Asp, or Glu"

(ix) FEATURE:
       (A) NAME/KEY: Modified-site
       (B) LOCATION: 112
       (D) OTHER INFORMATION: /note= "Xaa at position 112 is deleted or Leu, Ala, Val, Ile, Pro, Phe, Trp, or Met"

(ix) FEATURE:
       (A) NAME/KEY: Modified-site
       (B) LOCATION: 113
       (D) OTHER INFORMATION: /note= "Xaa at position 113 is deleted or Pro, Phe, Ala, Val, Leu, Ile, Trp, or Met"

(ix) FEATURE:
       (A) NAME/KEY: Modified-site
       (B) LOCATION: 114
       (D) OTHER INFORMATION: /note= "Xaa at position 114 is deleted or Pro, Phe, Ala, Val, Leu, Ile, Trp, or Met"

(ix) FEATURE:
       (A) NAME/KEY: Modified-site
       (B) LOCATION: 115
       (D) OTHER INFORMATION: /note= "Xaa at position 115 is deleted or Gln, Gly, Ser, Thr, Tyr, or Asn"

(ix) FEATURE:
       (A) NAME/KEY: Modified-site
       (B) LOCATION: 122
       (D) OTHER INFORMATION: /note= "Xaa at position 122 is Lys, Arg, His, Glu, or Asp"

(ix) FEATURE:
       (A) NAME/KEY: Modified-site
       (B) LOCATION: 200
       (D) OTHER INFORMATION: /note= "Xaa at position 200 is Trp, Ala, Val, Leu, Ile, Pro, Phe, Met, Arg and Lys, or His"

(xi) SEQUENCE DESCRIPTION: SEQ ID NO: 1:

| | | | | | | | | | | | | | | |
|---|---|---|---|---|---|---|---|---|---|---|---|---|---|---|
|Ser|Pro|Ala|Pro|Ala|Cys|Asp|Leu|Arg|Val|Leu|Ser|Lys|Leu|Leu|
|1| | |5| | | |10| | | |15| | | |

Arg Asp Ser His Val Leu His Ser Arg Leu Ser Gln Cys Pro Glu Val
              20                  25                  30

His Pro Leu Pro Xaa Pro Val Leu Leu Pro Ala Val Asp Xaa Xaa Leu
              35                  40                  45

Gly Glu Trp Lys Thr Gln Met Glu Glu Thr Lys Ala Gln Asp Ile Leu
50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
              85                  90                  95

Val Arg Leu Leu Leu Gly Ala Leu Gln Ser Leu Leu Gly Thr Gln Xaa
              100                 105                 110

Xaa Xaa Xaa Gly Arg Thr Thr Ala His Xaa Asp Pro Asn Ala Ile Phe
        115                 120                 125

Leu Ser Phe Gln His Leu Leu Arg Gly Lys Val Arg Phe Leu Met Leu
130                 135                 140

Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu Pro Asn
                165                 170                 175

Arg Thr Ser Gly Leu Leu Glu Thr Asn Phe Thr Ala Ser Ala Arg Thr
                180                 185                 190

Thr Gly Ser Gly Leu Leu Lys Xaa Gln Gln Gly Phe Arg Ala Lys Ile
                195                 200                 205

Pro Gly Leu Leu Asn Gln Thr Ser Arg Ser Leu Asp Gln Ile Pro Gly
210                 215                 220

Tyr Leu Asn Arg Ile His Glu Leu Leu Asn Gly Thr Arg Gly Leu Phe
225                 230                 235                 240

Pro Gly Pro Ser Arg Arg Thr Leu Gly Ala Pro Asp Ile Ser Ser Gly
                245                 250                 255

Thr Ser Asp Thr Gly Ser Leu Pro Pro Asn Leu Gln Pro Gly Tyr Ser
                260                 265                 270

Pro Ser Pro Thr His Pro Pro Thr Gly Gln Tyr Thr Leu Phe Pro Leu
            275                 280                 285

Pro Pro Thr Leu Pro Thr Pro Val Val Gln Leu His Pro Leu Leu Pro
290                 295                 300

Asp Pro Ser Ala Pro Thr Pro Thr Pro Thr Ser Pro Leu Leu Asn Thr
305                 310                 315                 320

Ser Tyr Thr His Ser Gln Asn Leu Ser Gln Glu Gly
                325                 330

(2) INFORMATION FOR SEQ ID NO: 2:

(i) SEQUENCE CHARACTERISTICS:
        (A) LENGTH: 332 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Modified-site
        (B) LOCATION: 37

(D) OTHER INFORMATION: /note= "Xaa at position 37 is Thr,
                Asp, or Glu"

(ix) FEATURE:
            (A) NAME/KEY: Modified-site
            (B) LOCATION: 46
            (D) OTHER INFORMATION: /note= "Xaa at position 46 is Ala,
                Val, Leu, Ile, Pro, Trp, or Met"

(ix) FEATURE:
            (A) NAME/KEY: Modified-site
            (B) LOCATION: 47
            (D) OTHER INFORMATION: /note= "Xaa at position 47 is Ser,
                Asp, or Glu"

(ix) FEATURE:
            (A) NAME/KEY: Modified-site
            (B) LOCATION: 112
            (D) OTHER INFORMATION: /note= "Xaa at position 112 is
                deleted or Ala, Val, Ile, Pro, Phe, Trp, or Met"

(ix) FEATURE:
            (A) NAME/KEY: Modified-site
            (B) LOCATION: 113
            (D) OTHER INFORMATION: /note= "Xaa at position 113 is
                deleted or Phe, Ala, Val, Leu, Ile, Trp, or Met"

(ix) FEATURE:
            (A) NAME/KEY: Modified-site
            (B) LOCATION: 114
            (D) OTHER INFORMATION: /note= "Xaa at position 114 is
                deleted or Phe, Ala, Val, Leu, Ile, Trp, or Met"

(ix) FEATURE:
            (A) NAME/KEY: Modified-site
            (B) LOCATION: 115
            (D) OTHER INFORMATION: /note= "Xaa at position 115 is
                deleted or Gly, Ser, Thr, Tyr, or Asn"

(ix) FEATURE:
            (A) NAME/KEY: Modified-site
            (B) LOCATION: 122
            (D) OTHER INFORMATION: /note= "Xaa at position 122 is Arg,
                His, Glu, or Asp"

(ix) FEATURE:
            (A) NAME/KEY: Modified-site
            (B) LOCATION: 200
            (D) OTHER INFORMATION: /note= "Xaa at position 200 is Ala,
                Val, Leu, Ile, Pro, Phe, Met, Arg, Lys, or His"

(xi) SEQUENCE DESCRIPTION: SEQ ID NO: 2:

Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
            20                  25                  30

His Pro Leu Pro Xaa Pro Val Leu Leu Pro Ala Val Asp Xaa Xaa Leu
        35                  40                  45

Gly Glu Trp Lys Thr Gln Met Glu Glu Thr Lys Ala Gln Asp Ile Leu
    50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Xaa
            100                 105                 110

Xaa Xaa Xaa Gly Arg Thr Thr Ala His Xaa Asp Pro Asn Ala Ile Phe
        115                 120                 125

Leu Ser Phe Gln His Leu Leu Arg Gly Lys Val Arg Phe Leu Met Leu
130                 135                 140

```
Val Gly Gly Ser Thr Leu Cys Val Arg Arg Ala Pro Thr Thr Ala
145                 150                 155                 160

Val Pro Ser Arg Thr Ser Leu Val Leu Thr Leu Asn Glu Leu Pro Asn
                165                 170                 175

Arg Thr Ser Gly Leu Leu Glu Thr Asn Phe Thr Ala Ser Ala Arg Thr
            180                 185                 190

Thr Gly Ser Gly Leu Leu Lys Xaa Gln Gln Gly Phe Arg Ala Lys Ile
            195                 200                 205

Pro Gly Leu Leu Asn Gln Thr Ser Arg Ser Leu Asp Gln Ile Pro Gly
        210                 215                 220

Tyr Leu Asn Arg Ile His Glu Leu Leu Asn Gly Thr Arg Gly Leu Phe
225                 230                 235                 240

Pro Gly Pro Ser Arg Arg Thr Leu Gly Ala Pro Asp Ile Ser Ser Gly
                245                 250                 255

Thr Ser Asp Thr Gly Ser Leu Pro Pro Asn Leu Gln Pro Gly Tyr Ser
            260                 265                 270

Pro Ser Pro Thr His Pro Pro Thr Gly Gln Tyr Thr Leu Phe Pro Leu
        275                 280                 285

Pro Pro Thr Leu Pro Thr Pro Val Val Gln Leu His Pro Leu Leu Pro
290                 295                 300

Asp Pro Ser Ala Pro Thr Pro Thr Pro Thr Ser Pro Leu Leu Asn Thr
305                 310                 315                 320

Ser Tyr Thr His Ser Gln Asn Leu Ser Gln Glu Gly
                325                 330
```

(2) INFORMATION FOR SEQ ID NO: 3:

(i) SEQUENCE CHARACTERISTICS:
        (A) LENGTH: 332 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Modified-site
        (B) LOCATION: 37
        (D) OTHER INFORMATION: /note= "Xaa at position 37 is Thr, Asp, or Glu"

(ix) FEATURE:
        (A) NAME/KEY: Modified-site
        (B) LOCATION: 46
        (D) OTHER INFORMATION: /note= "Xaa at position 46 is Ala, Val, Leu, Ile, Pro, Trp, or Met"

(ix) FEATURE:
        (A) NAME/KEY: Modified-site
        (B) LOCATION: 47
        (D) OTHER INFORMATION: /note= "Xaa at position 47 is Ser, Asp, or Glu"

(ix) FEATURE:
        (A) NAME/KEY: Modified-site
        (B) LOCATION: 112
        (D) OTHER INFORMATION: /note= "Xaa at position 112 is deleted or Ala, Val, Ile, Pro, Phe, Trp, or Met"

(ix) FEATURE:
        (A) NAME/KEY: Modified-site
        (B) LOCATION: 113
        (D) OTHER INFORMATION: /note= "Xaa at position 113 is deleted or Phe, Ala, Val, Leu, Ile, Trp, or Met"

(ix) FEATURE:

(A) NAME/KEY: Modified-site
         (B) LOCATION: 114
         (D) OTHER INFORMATION: /note= "Xaa at position 114 is
             deleted or Phe, Ala, Val, Leu, Ile, Trp, or Met"

(ix) FEATURE:
         (A) NAME/KEY: Modified-site
         (B) LOCATION: 115
         (D) OTHER INFORMATION: /note= "Xaa at position 115 is
             deleted or Gly, Ser, Thr, Tyr, or Asn"

(ix) FEATURE:
         (A) NAME/KEY: Modified-site
         (B) LOCATION: 122
         (D) OTHER INFORMATION: /note= "Xaa at position 122 is Arg,
             His, Glu, or Asp"

(ix) FEATURE:
         (A) NAME/KEY: Modified-site
         (B) LOCATION: 200
         (D) OTHER INFORMATION: /note= "Xaa at position 200 is Ala,
             Val, Leu, Ile, Pro, Phe, Met, Arg, Lys, or His"

(xi) SEQUENCE DESCRIPTION: SEQ ID NO: 3:

```
Ser Pro Ala Pro Pro Ala Cys Asp Leu Arg Val Leu Ser Lys Leu Leu
 1               5                  10                  15

Arg Asp Ser His Val Leu His Ser Arg Leu Ser Gln Cys Pro Glu Val
            20                  25                  30

His Pro Leu Pro Xaa Pro Val Leu Leu Pro Ala Val Asp Xaa Xaa Leu
        35                  40                  45

Gly Glu Trp Lys Thr Gln Met Glu Glu Thr Lys Ala Gln Asp Ile Leu
    50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Xaa
                100                 105                 110

Xaa Xaa Xaa Gly Arg Thr Thr Ala His Xaa Asp Pro Asn Ala Ile Phe
        115                 120                 125

Leu Ser Phe Gln His Leu Leu Arg Gly Lys Val Arg Phe Leu Met Leu
    130                 135                 140

Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu Pro Asn
                165                 170                 175

Arg Thr Ser Gly Leu Leu Glu Thr Asn Phe Thr Ala Ser Ala Arg Thr
            180                 185                 190

Thr Gly Ser Gly Leu Leu Lys Xaa Gln Gln Gly Phe Arg Ala Lys Ile
        195                 200                 205

Pro Gly Leu Leu Asn Gln Thr Ser Arg Ser Leu Asp Gln Ile Pro Gly
    210                 215                 220

Tyr Leu Asn Arg Ile His Glu Leu Leu Asn Gly Thr Arg Gly Leu Phe
225                 230                 235                 240

Pro Gly Pro Ser Arg Arg Thr Leu Gly Ala Pro Asp Ile Ser Ser Gly
                245                 250                 255

Thr Ser Asp Thr Gly Ser Leu Pro Pro Asn Leu Gln Pro Gly Tyr Ser
            260                 265                 270

Pro Ser Pro Thr His Pro Pro Thr Gly Gln Tyr Thr Leu Phe Pro Leu
        275                 280                 285
```

```
Pro Pro Thr Leu Pro Thr Pro Val Val Gln Leu His Pro Leu Leu Pro
    290                 295                 300

Asp Pro Ser Ala Pro Thr Pro Thr Pro Thr Ser Pro Leu Leu Asn Thr
305                 310                 315                 320

Ser Tyr Thr His Ser Gln Asn Leu Ser Gln Glu Gly
                325                 330
```

(2) INFORMATION FOR SEQ ID NO: 4:

(i) SEQUENCE CHARACTERISTICS:
        (A) LENGTH: 332 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Modified-site
        (B) LOCATION: 37
        (D) OTHER INFORMATION: /note= "Xaa at position 37 is Thr,
            Asp, or Glu"

(ix) FEATURE:
        (A) NAME/KEY: Modified-site
        (B) LOCATION: 46
        (D) OTHER INFORMATION: /note= "Xaa at position 46 is Ala,
            Val, Leu, or Ile"

(ix) FEATURE:
        (A) NAME/KEY: Modified-site
        (B) LOCATION: 47
        (D) OTHER INFORMATION: /note= "Xaa at position 47 is Ser,
            Asp, or Glu"

(ix) FEATURE:
        (A) NAME/KEY: Modified-site
        (B) LOCATION: 112
        (D) OTHER INFORMATION: /note= "Xaa at position 112 is
            deleted or Ala, Val, Ile, or Phe"

(ix) FEATURE:
        (A) NAME/KEY: Modified-site
        (B) LOCATION: 113
        (D) OTHER INFORMATION: /note= "Xaa at position 113 is
            deleted or Phe, Ala, Val, Leu, Ile, Trp, or Met"

(ix) FEATURE:
        (A) NAME/KEY: Modified-site
        (B) LOCATION: 114
        (D) OTHER INFORMATION: /note= "Xaa at position 114 is
            deleted or Phe, Ala, Val, Leu, Ile, Trp, or Met"

(ix) FEATURE:
        (A) NAME/KEY: Modified-site
        (B) LOCATION: 115
        (D) OTHER INFORMATION: /note= "Xaa at position 115 is
            deleted or Asn"

(ix) FEATURE:
        (A) NAME/KEY: Modified-site
        (B) LOCATION: 122
        (D) OTHER INFORMATION: /note= "Xaa at position 122 is Arg,
            His, Glu, or Asp"

(ix) FEATURE:
        (A) NAME/KEY: Modified-site
        (B) LOCATION: 200
        (D) OTHER INFORMATION: /note= "Xaa at position 200 is Ala,
            Val, Leu, Ile, Phe, or Met"

(xi) SEQUENCE DESCRIPTION: SEQ ID NO: 4:

```
Ser Pro Ala Pro Pro Ala Cys Asp Leu Arg Val Leu Ser Lys Leu Leu
1               5                   10                  15
```

```
Arg Asp Ser His Val Leu His Ser Arg Leu Ser Gln Cys Pro Glu Val
            20                  25                  30

His Pro Leu Pro Xaa Pro Val Leu Leu Pro Ala Val Asp Xaa Xaa Leu
            35                  40                  45

Gly Glu Trp Lys Thr Gln Met Glu Glu Thr Lys Ala Gln Asp Ile Leu
50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Xaa
                100                 105                 110

Xaa Xaa Xaa Gly Arg Thr Thr Ala His Xaa Asp Pro Asn Ala Ile Phe
            115                 120                 125

Leu Ser Phe Gln His Leu Leu Arg Gly Lys Val Arg Phe Leu Met Leu
130                 135                 140

Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu Pro Asn
                165                 170                 175

Arg Thr Ser Gly Leu Leu Glu Thr Asn Phe Thr Ala Ser Ala Arg Thr
                180                 185                 190

Thr Gly Ser Gly Leu Leu Lys Xaa Gln Gln Gly Phe Arg Ala Lys Ile
                195                 200                 205

Pro Gly Leu Leu Asn Gln Thr Ser Arg Ser Leu Asp Gln Ile Pro Gly
                210                 215                 220

Tyr Leu Asn Arg Ile His Glu Leu Leu Asn Gly Thr Arg Gly Leu Phe
225                 230                 235                 240

Pro Gly Pro Ser Arg Arg Thr Leu Gly Ala Pro Asp Ile Ser Ser Gly
                245                 250                 255

Thr Ser Asp Thr Gly Ser Leu Pro Pro Asn Leu Gln Pro Gly Tyr Ser
                260                 265                 270

Pro Ser Pro Thr His Pro Pro Thr Gly Gln Tyr Thr Leu Phe Pro Leu
                275                 280                 285

Pro Pro Thr Leu Pro Thr Pro Val Val Gln Leu His Pro Leu Leu Pro
                290                 295                 300

Asp Pro Ser Ala Pro Thr Pro Thr Pro Thr Ser Pro Leu Leu Asn Thr
305                 310                 315                 320

Ser Tyr Thr His Ser Gln Asn Leu Ser Gln Glu Gly
                325                 330
```

(2) INFORMATION FOR SEQ ID NO: 5:

(i) SEQUENCE CHARACTERISTICS:
        (A) LENGTH: 332 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Modified-site
        (B) LOCATION: 37
        (D) OTHER INFORMATION: /note= "Xaa at position 37 is Thr, Asp, or Glu"

(ix) FEATURE:
        (A) NAME/KEY: Modified-site

```
            (B) LOCATION: 46
            (D) OTHER INFORMATION: /note= "Xaa at position 46 is Ala,
                Val, Leu, or Ile"

(ix) FEATURE:
            (A) NAME/KEY: Modified-site
            (B) LOCATION: 47
            (D) OTHER INFORMATION: /note= "Xaa at position 47 is Ser,
                Asp, or Glu"

(ix) FEATURE:
            (A) NAME/KEY: Modified-site
            (B) LOCATION: 112
            (D) OTHER INFORMATION: /note= "Xaa at position 112 is Ala,
                Val, Ile, or Phe"

(ix) FEATURE:
            (A) NAME/KEY: Modified-site
            (B) LOCATION: 113
            (D) OTHER INFORMATION: /note= "Xaa at position 113 is Phe,
                Ala, Val, Leu, Ile, Trp, or Met"

(ix) FEATURE:
            (A) NAME/KEY: Modified-site
            (B) LOCATION: 114
            (D) OTHER INFORMATION: /note= "Xaa at position 114 is Phe,
                Ala, Val, Leu, Ile, Trp, or Met"

(ix) FEATURE:
            (A) NAME/KEY: Modified-site
            (B) LOCATION: 115
            (D) OTHER INFORMATION: /note= "Xaa at position 115 is Asn"

(ix) FEATURE:
            (A) NAME/KEY: Modified-site
            (B) LOCATION: 122
            (D) OTHER INFORMATION: /note= "Xaa at position 122 is Arg,
                His, Glu, or Asp"

(ix) FEATURE:
            (A) NAME/KEY: Modified-site
            (B) LOCATION: 200
            (D) OTHER INFORMATION: /note= "Xaa at position 200 is Ala,
                Val, Leu, Ile, Phe, or Met"

(xi) SEQUENCE DESCRIPTION: SEQ ID NO: 5:

Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
            20                  25                  30

His Pro Leu Pro Xaa Pro Val Leu Leu Pro Ala Val Asp Xaa Xaa Leu
        35                  40                  45

Gly Glu Trp Lys Thr Gln Met Glu Glu Thr Lys Ala Gln Asp Ile Leu
    50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
            85                  90                  95

Val Arg Leu Leu Leu Gly Ala Leu Gln Ser Leu Leu Gly Thr Gln Xaa
            100                 105                 110

Xaa Xaa Xaa Gly Arg Thr Thr Ala His Xaa Asp Pro Asn Ala Ile Phe
        115                 120                 125

Leu Ser Phe Gln His Leu Leu Arg Gly Lys Val Arg Phe Leu Met Leu
    130                 135                 140

Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu Pro Asn
            165                 170                 175
```

```
Arg Thr Ser Gly Leu Leu Glu Thr Asn Phe Thr Ala Ser Ala Arg Thr
            180                 185                 190

Thr Gly Ser Gly Leu Leu Lys Xaa Gln Gln Gly Phe Arg Ala Lys Ile
            195                 200                 205

Pro Gly Leu Leu Asn Gln Thr Ser Arg Ser Leu Asp Gln Ile Pro Gly
            210                 215                 220

Tyr Leu Asn Arg Ile His Glu Leu Leu Asn Gly Thr Arg Gly Leu Phe
225                 230                 235                 240

Pro Gly Pro Ser Arg Arg Thr Leu Gly Ala Pro Asp Ile Ser Ser Gly
            245                 250                 255

Thr Ser Asp Thr Gly Ser Leu Pro Pro Asn Leu Gln Pro Gly Tyr Ser
            260                 265                 270

Pro Ser Pro Thr His Pro Pro Thr Gly Gln Tyr Thr Leu Phe Pro Leu
            275                 280                 285

Pro Pro Thr Leu Pro Thr Pro Val Val Gln Leu His Pro Leu Leu Pro
            290                 295                 300

Asp Pro Ser Ala Pro Thr Pro Thr Pro Thr Ser Pro Leu Leu Asn Thr
305                 310                 315                 320

Ser Tyr Thr His Ser Gln Asn Leu Ser Gln Glu Gly
            325                 330
```

(2) INFORMATION FOR SEQ ID NO: 6:

(i) SEQUENCE CHARACTERISTICS:
        (A) LENGTH: 332 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Modified-site
        (B) LOCATION: 37
        (D) OTHER INFORMATION: /note= "Xaa at position 37 is Thr, Asp, or Glu"

(ix) FEATURE:
        (A) NAME/KEY: Modified-site
        (B) LOCATION: 46
        (D) OTHER INFORMATION: /note= "Xaa at position 46 is Phe, Ala, Val, Leu, Ile, Pro, Trp, or Met"

(ix) FEATURE:
        (A) NAME/KEY: Modified-site
        (B) LOCATION: 47
        (D) OTHER INFORMATION: /note= "Xaa at position 47 is Ser, Asp, or Glu"

(ix) FEATURE:
        (A) NAME/KEY: Modified-site
        (B) LOCATION: 112
        (D) OTHER INFORMATION: /note= "Xaa at position 112 is deleted or Leu, Ala, Val, Ile, Pro, Phe, Trp, or Met"

(ix) FEATURE:
        (A) NAME/KEY: Modified-site
        (B) LOCATION: 113
        (D) OTHER INFORMATION: /note= "Xaa at position 113 is deleted or Pro, Phe, Ala, Val, Leu, Ile, Trp, or Met"

(ix) FEATURE:
        (A) NAME/KEY: Modified-site
        (B) LOCATION: 114
        (D) OTHER INFORMATION: /note= "Xaa at position 114 is deleted or Pro, Phe, Ala, Val, Leu, Ile, Trp, or Met"

(ix) FEATURE:

(A) NAME/KEY: Modified-site
(B) LOCATION: 115
(D) OTHER INFORMATION: /note= "Xaa at position 115 is deleted or Gln, Gly, Ser, Thr, Tyr, or Asn"

(ix) FEATURE:
(A) NAME/KEY: Modified-site
(B) LOCATION: 122
(D) OTHER INFORMATION: /note= "Xaa at position 122 is Lys, Arg, His, Glu, or Asp"

(ix) FEATURE:
(A) NAME/KEY: Modified-site
(B) LOCATION: 200
(D) OTHER INFORMATION: /note= "Xaa at position 200 is Trp, Ala, Val, Leu, Ile, Pro, Phe, Met, Arg, Lys, or His"

(xi) SEQUENCE DESCRIPTION: SEQ ID NO: 6:

```
Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
            20                  25                  30

His Pro Leu Pro Xaa Pro Val Leu Leu Pro Ala Val Asp Xaa Xaa Leu
            35                  40                  45

Gly Glu Trp Lys Thr Gln Met Glu Glu Thr Lys Ala Gln Asp Ile Leu
50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Xaa
                100                 105                 110

Xaa Xaa Xaa Gly Arg Thr Thr Ala His Xaa Asp Pro Asn Ala Ile Phe
    115                 120                 125

Leu Ser Phe Gln His Leu Leu Arg Gly Lys Val Arg Phe Leu Met Leu
130                 135                 140

Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu Pro Asn
                165                 170                 175

Arg Thr Ser Gly Leu Leu Glu Thr Asn Phe Thr Ala Ser Ala Arg Thr
                180                 185                 190

Thr Gly Ser Gly Leu Leu Lys Xaa Gln Gln Gly Phe Arg Ala Lys Ile
                195                 200                 205

Pro Gly Leu Leu Asn Gln Thr Ser Arg Ser Leu Asp Gln Ile Pro Gly
210                 215                 220

Tyr Leu Asn Arg Ile His Glu Leu Leu Asn Gly Thr Arg Gly Leu Phe
225                 230                 235                 240

Pro Gly Pro Ser Arg Arg Thr Leu Gly Ala Pro Asp Ile Ser Ser Gly
                245                 250                 255

Thr Ser Asp Thr Gly Ser Leu Pro Pro Asn Leu Gln Pro Gly Tyr Ser
                260                 265                 270

Pro Ser Pro Thr His Pro Pro Thr Gly Gln Tyr Thr Leu Phe Pro Leu
                275                 280                 285

Pro Pro Thr Leu Pro Thr Pro Val Val Gln Leu His Pro Leu Leu Pro
                290                 295                 300

Asp Pro Ser Ala Pro Thr Pro Thr Pro Thr Ser Pro Leu Leu Asn Thr
305                 310                 315                 320
```

Ser Tyr Thr His Ser Gln Asn Leu Ser Gln Glu Gly
            325                 330

(2) INFORMATION FOR SEQ ID NO: 7:

(i) SEQUENCE CHARACTERISTICS:
        (A) LENGTH: 332 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Modified-site
        (B) LOCATION: 37
        (D) OTHER INFORMATION: /note= "Xaa at position 37 is Thr,
            Asp, or Glu"

(ix) FEATURE:
        (A) NAME/KEY: Modified-site
        (B) LOCATION: 46
        (D) OTHER INFORMATION: /note= "Xaa at position 46 is Ala,
            Val, Leu, or Ile"

(ix) FEATURE:
        (A) NAME/KEY: Modified-site
        (B) LOCATION: 47
        (D) OTHER INFORMATION: /note= "Xaa at position 47 is Ser,
            Asp, or Glu"

(ix) FEATURE:
        (A) NAME/KEY: Modified-site
        (B) LOCATION: 112
        (D) OTHER INFORMATION: /note= "Xaa at position 112 is
            deleted or Ala, Val, Ile, or Phe"

(ix) FEATURE:
        (A) NAME/KEY: Modified-site
        (B) LOCATION: 113
        (D) OTHER INFORMATION: /note= "Xaa at position 113 is
            deleted or Phe, Ala, Val, Leu, Ile, Trp, or Met"

(ix) FEATURE:
        (A) NAME/KEY: Modified-site
        (B) LOCATION: 114
        (D) OTHER INFORMATION: /note= "Xaa at position 114 is
            deleted or Phe, Ala, Val, Leu, Ile, Trp, or Met"

(ix) FEATURE:
        (A) NAME/KEY: Modified-site
        (B) LOCATION: 115
        (D) OTHER INFORMATION: /note= "Xaa at position 115 is
            deleted or Asn"

(ix) FEATURE:
        (A) NAME/KEY: Modified-site
        (B) LOCATION: 122
        (D) OTHER INFORMATION: /note= "Xaa at position 122 is Arg,
            His, Glu, or Asp"

(ix) FEATURE:
        (A) NAME/KEY: Modified-site
        (B) LOCATION: 200
        (D) OTHER INFORMATION: /note= "Xaa at position 200 is Ala,
            Val, Leu, Ile, Phe, or Met"

(xi) SEQUENCE DESCRIPTION: SEQ ID NO: 7:

Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
                20                  25                  30

His Pro Leu Pro Xaa Pro Val Leu Leu Pro Ala Val Asp Xaa Xaa Leu
            35                  40                  45

```
Gly Glu Trp Lys Thr Gln Met Glu Thr Lys Ala Gln Asp Ile Leu
    50                  55                  60

Gly Ala Val Thr Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Xaa
            100                 105                 110

Xaa Xaa Xaa Gly Arg Thr Thr Ala His Xaa Asp Pro Asn Ala Ile Phe
        115                 120                 125

Leu Ser Phe Gln His Leu Leu Arg Gly Lys Val Arg Phe Leu Met Leu
    130                 135                 140

Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu Pro Asn
            165                 170                 175

Arg Thr Ser Gly Leu Leu Glu Thr Asn Phe Thr Ala Ser Ala Arg Thr
        180                 185                 190

Thr Gly Ser Gly Leu Leu Lys Xaa Gln Gln Gly Phe Arg Ala Lys Ile
    195                 200                 205

Pro Gly Leu Leu Asn Gln Thr Ser Arg Ser Leu Asp Gln Ile Pro Gly
    210                 215                 220

Tyr Leu Asn Arg Ile His Glu Leu Leu Asn Gly Thr Arg Gly Leu Phe
225                 230                 235                 240

Pro Gly Pro Ser Arg Arg Thr Leu Gly Ala Pro Asp Ile Ser Ser Gly
            245                 250                 255

Thr Ser Asp Thr Gly Ser Leu Pro Pro Asn Leu Gln Pro Gly Tyr Ser
        260                 265                 270

Pro Ser Pro Thr His Pro Pro Thr Gly Gln Tyr Thr Leu Phe Pro Leu
    275                 280                 285

Pro Pro Thr Leu Pro Thr Pro Val Val Gln Leu His Pro Leu Leu Pro
    290                 295                 300

Asp Pro Ser Ala Pro Thr Pro Thr Ser Pro Leu Leu Asn Thr
305                 310                 315                 320

Ser Tyr Thr His Ser Gln Asn Leu Ser Gln Glu Gly
            325                 330
```

(2) INFORMATION FOR SEQ ID NO: 8:

(i) SEQUENCE CHARACTERISTICS:
        (A) LENGTH: 332 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Modified-site
        (B) LOCATION: 37
        (D) OTHER INFORMATION: /note= "Xaa at position 37 is Thr, Asp, or Glu"

(ix) FEATURE:
        (A) NAME/KEY: Modified-site
        (B) LOCATION: 46
        (D) OTHER INFORMATION: /note= "Xaa at position 46 is Ala, Val, Leu, or Ile"

(ix) FEATURE:
        (A) NAME/KEY: Modified-site

```
         (B) LOCATION: 47
         (D) OTHER INFORMATION: /note= "Xaa at position 47 is Ser,
             Asp, or Glu"

(ix) FEATURE:
         (A) NAME/KEY: Modified-site
         (B) LOCATION: 112
         (D) OTHER INFORMATION: /note= "Xaa at position 112 is Ala,
             Val, Ile, or Phe"

(ix) FEATURE:
         (A) NAME/KEY: Modified-site
         (B) LOCATION: 113
         (D) OTHER INFORMATION: /note= "Xaa at position 113 is Pro,
             Phe, Ala, Val, Leu, Ile, Trp, or Met"

(ix) FEATURE:
         (A) NAME/KEY: Modified-si te
         (B) LOCATION: 114
         (D) OTHER INFORMATION: /note= "Xaa at position 114 is Pro,
             Phe, Ala, Val, Leu, Ile, Trp, or Met"

(ix) FEATURE:
         (A) NAME/KEY: Modified-site
         (B) LOCATION: 115
         (D) OTHER INFORMATION: /note= "Xaa at position 115 is Asn"

(ix) FEATURE:
         (A) NAME/KEY: Modified-site
         (B) LOCATION: 122
         (D) OTHER INFORMATION: /note= "Xaa at position 122 is Arg,
             His, Glu, or Asp"

(ix) FEATURE:
         (A) NAME/KEY: Modified-site
         (B) LOCATION: 200
         (D) OTHER INFORMATION: /note= "Xaa at position 200 is Ala,
             Val, Leu, Ile, Phe, or Met"

(xi) SEQUENCE DESCRIPTION: SEQ ID NO: 8:

Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
            20                  25                  30

His Pro Leu Pro Xaa Pro Val Leu Leu Pro Ala Val Asp Xaa Xaa Leu
        35                  40                  45

Gly Glu Trp Lys Thr Gln Met Glu Glu Thr Lys Ala Gln Asp Ile Leu
50                      55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Xaa
                100                 105                 110

Xaa Xaa Xaa Gly Arg Thr Thr Ala His Xaa Asp Pro Asn Ala Ile Phe
        115                 120                 125

Leu Ser Phe Gln His Leu Leu Arg Gly Lys Val Arg Phe Leu Met Leu
130                 135                 140

Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu Pro Asn
                165                 170                 175

Arg Thr Ser Gly Leu Leu Glu Thr Asn Phe Thr Ala Ser Ala Arg Thr
                180                 185                 190

Thr Gly Ser Gly Leu Leu Lys Xaa Gln Gln Gly Phe Arg Ala Lys Ile
                195                 200                 205
```

```
Pro Gly Leu Leu Asn Gln Thr Ser Arg Ser Leu Asp Gln Ile Pro Gly
    210                 215                 220

Tyr Leu Asn Arg Ile His Glu Leu Leu Asn Gly Thr Arg Gly Leu Phe
225                 230                 235                 240

Pro Gly Pro Ser Arg Arg Thr Leu Gly Ala Pro Asp Ile Ser Ser Gly
                245                 250                 255

Thr Ser Asp Thr Gly Ser Leu Pro Pro Asn Leu Gln Pro Gly Tyr Ser
                260                 265                 270

Pro Ser Pro Thr His Pro Pro Thr Gly Gln Tyr Thr Leu Phe Pro Leu
            275                 280                 285

Pro Pro Thr Leu Pro Thr Pro Val Val Gln Leu His Pro Leu Leu Pro
        290                 295                 300

Asp Pro Ser Ala Pro Thr Pro Thr Pro Thr Ser Pro Leu Leu Asn Thr
305                 310                 315                 320

Ser Tyr Thr His Ser Gln Asn Leu Ser Gln Glu Gly
                325                 330
```

(2) INFORMATION FOR SEQ ID NO: 9:

(i) SEQUENCE CHARACTERISTICS:
        (A) LENGTH: 332 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Modified-site
        (B) LOCATION: 37
        (D) OTHER INFORMATION: /note= "Xaa at position 37 is Thr, Asp, or Glu"

(ix) FEATURE:
        (A) NAME/KEY: Modified-site
        (B) LOCATION: 46
        (D) OTHER INFORMATION: /note= "Xaa at position 46 is Leu or Phe"

(ix) FEATURE:
        (A) NAME/KEY: Modified-site
        (B) LOCATION: 47
        (D) OTHER INFORMATION: /note= "Xaa at position 47 is Ser, Asp, or Glu"

(ix) FEATURE:
        (A) NAME/KEY: Modified-site
        (B) LOCATION: 112
        (D) OTHER INFORMATION: /note= "Xaa at position 112 is deleted or Leu"

(ix) FEATURE:
        (A) NAME/KEY: Modified-site
        (B) LOCATION: 113
        (D) OTHER INFORMATION: /note= "Xaa at position 113 is deleted or Pro"

(ix) FEATURE:
        (A) NAME/KEY: Modified-site
        (B) LOCATION: 114
        (D) OTHER INFORMATION: /note= "Xaa at position 114 is deleted or Pro"

(ix) FEATURE:
        (A) NAME/KEY: Modified-site
        (B) LOCATION: 115
        (D) OTHER INFORMATION: /note= "Xaa at position 115 is deleted or Gln"

(ix) FEATURE:

(A) NAME/KEY: Modified-site
              (B) LOCATION: 122
              (D) OTHER INFORMATION: /note= "Xaa at position 122 is Lys or
                  Glu"

(ix) FEATURE:
              (A) NAME/KEY: Modified-site
              (B) LOCATION: 200
              (D) OTHER INFORMATION: /note= "Xaa at position 200 is Trp or
                  Arg"

(xi) SEQUENCE DESCRIPTION: SEQ ID NO: 9:

```
Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
            20                  25                  30

His Pro Leu Pro Xaa Pro Val Leu Leu Pro Ala Val Asp Xaa Xaa Leu
        35                  40                  45

Gly Glu Trp Lys Thr Gln Met Glu Glu Thr Lys Ala Gln Asp Ile Leu
    50                  55                  60

Gly Ala Val Thr Leu Leu Glu Gly Val Met Ala Ala Arg Gly Gln
65              70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Xaa
                100                 105                 110

Xaa Xaa Xaa Gly Arg Thr Thr Ala His Xaa Asp Pro Asn Ala Ile Phe
        115                 120                 125

Leu Ser Phe Gln His Leu Leu Arg Gly Lys Val Arg Phe Leu Met Leu
130                 135                 140

Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu Pro Asn
                165                 170                 175

Arg Thr Ser Gly Leu Leu Glu Ser Asn Phe Thr Ala Ser Ala Arg Thr
            180                 185                 190

Thr Gly Ser Gly Leu Leu Lys Xaa Gln Gln Gly Phe Arg Ala Lys Ile
        195                 200                 205

Pro Gly Leu Leu Asn Gln Thr Ser Arg Ser Leu Asp Gln Ile Pro Gly
210                 215                 220

Tyr Leu Asn Arg Ile His Glu Leu Leu Asn Gly Thr Arg Gly Leu Phe
225                 230                 235                 240

Pro Gly Pro Ser Arg Arg Thr Leu Gly Ala Pro Asp Ile Ser Ser Gly
            245                 250                 255

Thr Ser Asp Thr Gly Ser Leu Pro Pro Asn Leu Gln Pro Gly Tyr Ser
        260                 265                 270

Pro Ser Pro Thr His Pro Pro Thr Gly Gln Tyr Thr Leu Phe Pro Leu
    275                 280                 285

Pro Pro Thr Leu Pro Thr Pro Val Val Gln Leu His Pro Leu Leu Pro
290                 295                 300

Asp Pro Ser Ala Pro Thr Pro Thr Pro Thr Ser Pro Leu Leu Asn Thr
305                 310                 315                 320

Ser Tyr Thr His Ser Gln Asn Leu Ser Gln Glu Gly
                325                 330
```

(2) INFORMATION FOR SEQ ID NO: 10:

```
    (i) SEQUENCE CHARACTERISTICS:
        (A) LENGTH: 332 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Modified-site
        (B) LOCATION: 37
        (D) OTHER INFORMATION: /note= "Xaa at position 37 is Thr,
            Asp, or Glu"

(ix) FEATURE:
        (A) NAME/KEY: Modified-site
        (B) LOCATION: 46
        (D) OTHER INFORMATION: /note= "Xaa at position 46 is Leu"

(ix) FEATURE:
        (A) NAME/KEY: Modified-site
        (B) LOCATION: 47
        (D) OTHER INFORMATION: /note= "Xaa at position 47 is Ser,
            Asp, or Glu"

(ix) FEATURE:
        (A) NAME/KEY: Modified-site
        (B) LOCATION: 112
        (D) OTHER INFORMATION: /note= "Xaa at position 112 is Leu"

(ix) FEATURE:
        (A) NAME/KEY: Modified-site
        (B) LOCATION: 113
        (D) OTHER INFORMATION: /note= "Xaa at position 113 is Pro"

(ix) FEATURE:
        (A) NAME/KEY: Modified-site
        (B) LOCATION: 114
        (D) OTHER INFORMATION: /note= "Xaa at position 114 is Pro"

(ix) FEATURE:
        (A) NAME/KEY: Modified-site
        (B) LOCATION: 115
        (D) OTHER INFORMATION: /note= "Xaa at position 115 is Gln"

(ix) FEATURE:
        (A) NAME/KEY: Modified-site
        (B) LOCATION: 122
        (D) OTHER INFORMATION: /note= "Xaa at position 122 is Glu"

(ix) FEATURE:
        (A) NAME/KEY: Modified-site
        (B) LOCATION: 200
        (D) OTHER INFORMATION: /note= "Xaa at position 200 is Arg"

(xi) SEQUENCE DESCRIPTION: SEQ ID NO: 10:

Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
                20                  25                  30

His Pro Leu Pro Xaa Pro Val Leu Leu Pro Ala Val Asp Xaa Xaa Leu
            35                  40                  45

Gly Glu Trp Lys Thr Gln Met Glu Glu Thr Lys Ala Gln Asp Ile Leu
50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Xaa
                100                 105                 110

Xaa Xaa Xaa Gly Arg Thr Thr Ala His Xaa Asp Pro Asn Ala Ile Phe
```

```
                    115                 120                     125
Leu Ser Phe Gln His Leu Leu Arg Gly Lys Val Arg Phe Leu Met Leu
    130                 135                 140
Val Gly Gly Ser Thr Leu Cys Val Arg Arg Ala Pro Pro Thr Thr Ala
145                 150                 155                 160
Val Pro Ser Arg Thr Ser Leu Val Leu Thr Leu Asn Glu Leu Pro Asn
                165                 170                 175
Arg Thr Ser Gly Leu Leu Glu Thr Asn Phe Thr Ala Ser Ala Arg Thr
            180                 185                 190
Thr Gly Ser Gly Leu Leu Lys Xaa Gln Gln Gly Phe Arg Ala Lys Ile
            195                 200                 205
Pro Gly Leu Leu Asn Gln Thr Ser Arg Ser Leu Asp Gln Ile Pro Gly
    210                 215                 220
Tyr Leu Asn Arg Ile His Glu Leu Leu Asn Gly Thr Arg Gly Leu Phe
225                 230                 235                 240
Pro Gly Pro Ser Arg Arg Thr Leu Gly Ala Pro Asp Ile Ser Ser Gly
                245                 250                 255
Thr Ser Asp Thr Gly Ser Leu Pro Pro Asn Leu Gln Pro Gly Tyr Ser
            260                 265                 270
Pro Ser Pro Thr His Pro Pro Thr Gly Gln Tyr Thr Leu Phe Pro Leu
            275                 280                 285
Pro Pro Thr Leu Pro Thr Pro Val Val Gln Leu His Pro Leu Leu Pro
    290                 295                 300
Asp Pro Ser Ala Pro Thr Pro Thr Pro Thr Ser Pro Leu Leu Asn Thr
305                 310                 315                 320
Ser Tyr Thr His Ser Gln Asn Leu Ser Gln Glu Gly
                325                 330
```

(2) INFORMATION FOR SEQ ID NO: 11:

(i) SEQUENCE CHARACTERISTICS:
        (A) LENGTH: 332 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Modified-site
        (B) LOCATION: 37
        (D) OTHER INFORMATION: /note= "Xaa at position 37 is Thr,
            Asp, or Glu"

(ix) FEATURE:
        (A) NAME/KEY: Modified-site
        (B) LOCATION: 46
        (D) OTHER INFORMATION: /note= "Xaa at position 46 is Phe or
            Leu"

(ix) FEATURE:
        (A) NAME/KEY: Modified-site
        (B) LOCATION: 47
        (D) OTHER INFORMATION: /note= "Xaa at position 47 is Ser,
            Asp, or Glu"

(ix) FEATURE:
        (A) NAME/KEY: Modified-site
        (B) LOCATION: 122
        (D) OTHER INFORMATION: /note= "Xaa at position 122 is Lys or
            Glu"

(ix) FEATURE:
        (A) NAME/KEY: Modified-site
        (B) LOCATION: 200

(D) OTHER INFORMATION: /note= "Xaa at position 200 is Trp or Arg"

(xi) SEQUENCE DESCRIPTION: SEQ ID NO: 11:

```
Ser Pro Ala Pro Pro Ala Cys Asp Leu Arg Val Leu Ser Lys Leu Leu
 1               5                  10                  15

Arg Asp Ser His Val Leu His Ser Arg Leu Ser Gln Cys Pro Glu Val
             20                  25                  30

His Pro Leu Pro Xaa Pro Val Leu Leu Pro Ala Val Asp Xaa Xaa Leu
         35                  40                  45

Gly Glu Trp Lys Thr Gln Met Glu Glu Thr Lys Ala Gln Asp Ile Leu
 50                  55                  60

Gly Ala Val Thr Leu Leu Leu Glu Gly Val Met Ala Ala Arg Gly Gln
 65                  70                  75                  80

Leu Gly Pro Thr Cys Leu Ser Ser Leu Leu Gly Gln Leu Ser Gly Gln
                 85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Xaa Asp Pro Asn Ala Ile Phe
            115                 120                 125

Leu Ser Phe Gln His Leu Leu Arg Gly Lys Val Arg Phe Leu Met Leu
130                 135                 140

Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu Pro Asn
                165                 170                 175

Arg Thr Ser Gly Leu Leu Glu Thr Asn Phe Thr Ala Ser Ala Arg Thr
                180                 185                 190

Thr Gly Ser Gly Leu Leu Lys Xaa Gln Gln Gly Phe Arg Ala Lys Ile
                195                 200                 205

Pro Gly Leu Leu Asn Gln Thr Ser Arg Ser Leu Asp Gln Ile Pro Gly
210                 215                 220

Tyr Leu Asn Arg Ile His Glu Leu Leu Asn Gly Thr Arg Gly Leu Phe
225                 230                 235                 240

Pro Gly Pro Ser Arg Arg Thr Leu Gly Ala Pro Asp Ile Ser Ser Gly
                245                 250                 255

Thr Ser Asp Thr Gly Ser Leu Pro Pro Asn Leu Gln Pro Gly Tyr Ser
                260                 265                 270

Pro Ser Pro Thr His Pro Pro Thr Gly Gln Tyr Thr Leu Phe Pro Leu
                275                 280                 285

Pro Pro Thr Leu Pro Thr Pro Val Val Gln Leu His Pro Leu Leu Pro
                290                 295                 300

Asp Pro Ser Ala Pro Thr Pro Thr Pro Thr Ser Pro Leu Leu Asn Thr
305                 310                 315                 320

Ser Tyr Thr His Ser Gln Asn Leu Ser Gln Glu Gly
                325                 330
```

(2) INFORMATION FOR SEQ ID NO: 12:

(i) SEQUENCE CHARACTERISTICS:
      (A) LENGTH: 153 amino acids
      (B) TYPE: amino acid
      (C) STRANDEDNESS:
      (D) TOPOLOGY: linear (ii) MOLECULE TYPE: protein -continued

```
    (ix) FEATURE:
         (A) NAME/KEY: Modified-site
         (B) LOCATION: 37
         (D) OTHER INFORMATION: /note= "Xaa at position 37 is Thr,
             Asp, or Glu"

(ix) FEATURE:
         (A) NAME/KEY: Modified-site
         (B) LOCATION: 46
         (D) OTHER INFORMATION: /note= "Xaa at position 46 is
             Phe, Ala, Val, Leu, Ile, Pro, Trp, or Met"

(ix) FEATURE:
         (A) NAME/KEY: Modified-site
         (B) LOCATION: 47
         (D) OTHER INFORMATION: /note= "Xaa at position 47 is Ser,
             Asp, or Glu"

(ix) FEATURE:
         (A) NAME/KEY: Modified-site
         (B) LOCATION: 112
         (D) OTHER INFORMATION: /note= "Xaa at position 112 is
             deleted or Leu, Ala, Val, Ile, Pro, Phe, Trp, or Met"

(ix) FEATURE:
         (A) NAME/KEY: Modified-site
         (B) LOCATION: 113
         (D) OTHER INFORMATION: /note= "Xaa at position 113  is
             deleted or Pro, Phe, Ala, Val, Leu, Ile, Trp, or Met"

(ix) FEATURE:
         (A) NAME/KEY: Modified-site
         (B) LOCATION: 114
         (D) OTHER INFORMATION: /note= "Xaa at position 114 is
             deleted or Pro, Phe, Ala, Val, Leu, Ile, Trp, or Met"

(ix) FEATURE:
         (A) NAME/KEY: Modified-site
         (B) LOCATION: 115
         (D) OTHER INFORMATION: /note= "Xaa at position 115 is
             deleted or Gln, Gly, Ser, Thr, Tyr, or Asn"

(ix) FEATURE:
         (A) NAME/KEY: Modified-site
         (B) LOCATION: 122
         (D) OTHER INFORMATION: /note= "Xaa at position 122 is Lys,
             Arg, His, Glu, or Asp"

(xi) SEQUENCE DESCRIPTION: SEQ ID NO: 12:

Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
            20                  25                  30

His Pro Leu Pro Xaa Pro Val Leu Leu Pro Ala Val Asp Xaa Xaa Leu
        35                  40                  45

Gly Glu Trp Lys Thr Gln Met Glu Glu Thr Lys Ala Gln Asp Ile Leu
    50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Xaa
            100                 105                 110

Xaa Xaa Xaa Gly Arg Thr Thr Ala His Xaa Asp Pro Asn Ala Ile Phe
        115                 120                 125

Leu Ser Phe Gln His Leu Leu Arg Gly Lys Val Arg Phe Leu Met Leu
    130                 135                 140

Val Gly Gly Ser Thr Leu Cys Val Arg
145                 150
```

INFORMATION FOR SEQ ID NO: 13:

(i) SEQUENCE CHARACTERISTICS:
        (A) LENGTH: 153 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Modified-site
        (B) LOCATION: 37
        (D) OTHER INFORMATION: /note= "Xaa at position 37 is Thr,
            Asp, or Glu"

(ix) FEATURE:
        (A) NAME/KEY: Modified-site
        (B) LOCATION: 46
        (D) OTHER INFORMATION: /note= "Xaa at position 46 is Ala,
            Val, Leu, Ile, Pro, Trp, or Met"

(ix) FEATURE:
        (A) NAME/KEY: Modified-site
        (B) LOCATION: 47
        (D) OTHER INFORMATION: /note= "Xaa at position 47 is Ser,
            Asp, or Glu"

(ix) FEATURE:
        (A) NAME/KEY: Modified-site
        (B) LOCATION: 112
        (D) OTHER INFORMATION: /note= "Xaa at position 112 is
            deleted or Ala, Val, Ile, Pro, Phe, Trp, or Met"

(ix) FEATURE:
        (A) NAME/KEY: Modified-site
        (B) LOCATION: 113
        (D) OTHER INFORMATION: /note= "Xaa at position 113 is
            deleted or Phe, Ala, Val, Leu, Ile, Trp, or Met"

(ix) FEATURE:
        (A) NAME/KEY: Modified-site
        (B) LOCATION: 114
        (D) OTHER INFORMATION: /note= "Xaa at position 114 is
            deleted or Phe, Ala, Val, Leu, Ile, Trp, or Met"

(ix) FEATURE:
        (A) NAME/KEY: Modified-site
        (B) LOCATION: 115
        (D) OTHER INFORMATION: /note= "Xaa at position 115 is
            deleted or Gly, Ser, Thr, Tyr, or Asn"

(ix) FEATURE:
        (A) NAME/KEY: Modified-site
        (B) LOCATION: 122
        (D) OTHER INFORMATION: /note= "Xaa at position 122 is Arg,
            His, Glu, or Asp"

(xi) SEQUENCE DESCRIPTION: SEQ ID NO: 13:

```
Ser Pro Ala Pro Pro Ala Cys Asp Leu Arg Val Leu Ser Lys Leu Leu
 1               5                  10                  15

Arg Asp Ser His Val Leu His Ser Arg Leu Ser Gln Cys Pro Glu Val
            20                  25                  30

His Pro Leu Pro Xaa Pro Val Leu Pro Ala Val Asp Xaa Xaa Leu
        35                  40                  45

Gly Glu Trp Lys Thr Gln Met Glu Glu Thr Lys Ala Gln Asp Ile Leu
 50                  55                  60

Gly Ala Val Thr Leu Leu Leu Glu Gly Val Met Ala Ala Arg Gly Gln
 65                  70                  75                  80

Leu Gly Pro Thr Cys Leu Ser Ser Leu Leu Gly Gln Leu Ser Gly Gln
            85                  90                  95
```

```
Val Arg Leu Leu Leu Gly Ala Leu Gln Ser Leu Leu Gly Thr Gln Xaa
            100                 105                 110

Xaa Xaa Xaa Gly Arg Thr Thr Ala His Xaa Asp Pro Asn Ala Ile Phe
        115                 120                 125

Leu Ser Phe Gln His Leu Leu Arg Gly Lys Val Arg Phe Leu Met Leu
130                 135                 140

Val Gly Gly Ser Thr Leu Cys Val Arg
145                 150
```

(2) INFORMATION FOR SEQ ID NO: 14:

(i) SEQUENCE CHARACTERISTICS:
        (A) LENGTH: 153 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Modified-site
        (B) LOCATION: 37
        (D) OTHER INFORMATION: /note= "Xaa at position 37 is Thr,
            Asp, or Glu"

(ix) FEATURE:
        (A) NAME/KEY: Modified-site
        (B) LOCATION: 46
        (D) OTHER INFORMATION: /note= "Xaa at position 46 is Ala,
            Val, Leu, Ile, Pro, Trp, or Met"

(ix) FEATURE:
        (A) NAME/KEY: Modified-site
        (B) LOCATION: 47
        (D) OTHER INFORMATION: /note= "Xaa at position 47 is Ser,
            Asp, or Glu"

(ix) FEATURE:
        (A) NAME/KEY: Modified-site
        (B) LOCATION: 112
        (D) OTHER INFORMATION: /note= "Xaa at position 112 is
            deleted or Ala, Val, Ile, Pro, Phe, Trp, or Met"

(ix) FEATURE:
        (A) NAME/KEY: Modified-site
        (B) LOCATION: 113
        (D) OTHER INFORMATION: /note= "Xaa at position 113 is
            deleted or Phe, Ala, Val, Leu, Ile, Trp, or Met"

(ix) FEATURE:
        (A) NAME/KEY: Modified-site
        (B) LOCATION: 114
        (D) OTHER INFORMATION: /note= "Xaa at position 114 is
            deleted or Phe, Ala, Val, Leu, Ile, Trp, or Met"

(ix) FEATURE:
        (A) NAME/KEY: Modified-site
        (B) LOCATION: 115
        (D) OTHER INFORMATION: /note= "Xaa at position 115 is
            deleted or Gly, Ser, Thr, Tyr, or Asn"

(ix) FEATURE:
        (A) NAME/KEY: Modified-site
        (B) LOCATION: 122
        (D) OTHER INFORMATION: /note= "Xaa at position 122 is Arg,
            His, Glu, or Asp"

(xi) SEQUENCE DESCRIPTION: SEQ ID NO: 14:

```
Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
            20                  25                  30
```

His Pro Leu Pro Xaa Pro Val Leu Leu Pro Ala Val Asp Xaa Xaa Leu
        35              40                  45
Gly Glu Trp Lys Thr Gln Met Glu Gly Thr Lys Ala Gln Asp Ile Leu
 50              55                  60
Gly Ala Val Thr Leu Leu Glu Gly Val Met Ala Ala Arg Gly Gln
 65              70                  75              80
Leu Gly Pro Thr Cys Leu Ser Ser Leu Leu Gly Gln Leu Ser Gly Gln
                 85              90                  95
Val Arg Leu Leu Leu Gly Ala Leu Gln Ser Leu Leu Gly Thr Gln Xaa
            100             105                 110
Xaa Xaa Xaa Gly Arg Thr Thr Ala His Xaa Asp Pro Asn Ala Ile Phe
        115             120                 125
Leu Ser Phe Gln His Leu Leu Arg Gly Lys Val Arg Phe Leu Met Leu
130             135                 140
Val Gly Gly Ser Thr Leu Cys Val Arg
145             150

(2) INFORMATION FOR SEQ ID NO: 15:

(i) SEQUENCE CHARACTERISTICS:
        (A) LENGTH: 153 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Modified-site
        (B) LOCATION: 37
        (D) OTHER INFORMATION: /note= "Xaa at position 37 is Thr,
            Asp, or Glu"

(ix) FEATURE:
        (A) NAME/KEY: Modified-site
        (B) LOCATION: 46
        (D) OTHER INFORMATION: /note= "Xaa at position 46 is Ala,
            Val, Leu, or Ile"

(ix) FEATURE:
        (A) NAME/KEY: Modified-site
        (B) LOCATION: 47
        (D) OTHER INFORMATION: /note= "Xaa at position 47 is Ser,
            Asp, or Glu"

(ix) FEATURE:
        (A) NAME/KEY: Modified-site
        (B) LOCATION: 112
        (D) OTHER INFORMATION: /note= "Xaa at position 112 is
            deleted or Ala, Val, Ile, or Phe"

(ix) FEATURE:
        (A) NAME/KEY: Modified-site
        (B) LOCATION: 113
        (D) OTHER INFORMATION: /note= "Xaa at position 113 is
            deleted or Phe, Ala, Val, Leu, Ile, Trp, or Met"

(ix) FEATURE:
        (A) NAME/KEY: Modified-site
        (B) LOCATION: 114
        (D) OTHER INFORMATION: /note= "Xaa at position 114 is
            deleted or Phe, Ala, Val, Leu, Ile, Trp, or Met"

(ix) FEATURE:
        (A) NAME/KEY: Modified-site
        (B) LOCATION: 115
        (D) OTHER INFORMATION: /note= "Xaa at position 115 is
            deleted or Asn"

(ix) FEATURE:

(A) NAME/KEY: Modified-site
                (B) LOCATION: 122
                (D) OTHER INFORMATION: /note= "Xaa at position 122 is Arg,
                    His, Glu, or Asp"

(xi) SEQUENCE DESCRIPTION: SEQ ID NO: 15:

Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
                20                  25                  30

His Pro Leu Pro Xaa Pro Val Leu Leu Pro Ala Val Asp Xaa Xaa Leu
                35                  40                  45

Gly Glu Trp Lys Thr Gln Met Glu Gly Thr Lys Ala Gln Asp Ile Leu
    50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Xaa
                100                 105                 110

Xaa Xaa Xaa Gly Arg Thr Thr Ala His Xaa Asp Pro Asn Ala Ile Phe
        115                 120                 125

Leu Ser Phe Gln His Leu Leu Arg Gly Lys Val Arg Phe Leu Met Leu
130                 135                 140

Val Gly Gly Ser Thr Leu Cys Val Arg
145                 150

(2) INFORMATION FOR SEQ ID NO: 16:

(i) SEQUENCE CHARACTERISTICS:
                (A) LENGTH: 153 amino acids
                (B) TYPE: amino acid
                (C) STRANDEDNESS:
                (D) TOPOLOGY: linear (ii) MOLECULE TYPE: protein (ix) FEATURE:
                (A) NAME/KEY: Modified-site
                (B) LOCATION: 37
                (D) OTHER INFORMATION: /note= "Xaa at position 37 is Thr,
                    Asp, or Glu"

(ix) FEATURE:
                (A) NAME/KEY: Modified-site
                (B) LOCATION: 46
                (D) OTHER INFORMATION: /note= "Xaa at position 46 is Ala,
                    Val, Leu, or Ile"

(ix) FEATURE:
                (A) NAME/KEY: Modified-site
                (B) LOCATION: 47
                (D) OTHER INFORMATION: /note= "Xaa at position 47 is Ser,
                    Asp, or Glu"

(ix) FEATURE:
                (A) NAME/KEY: Modified-site
                (B) LOCATION: 112
                (D) OTHER INFORMATION: /note= "Xaa at position 112 is Ala,
                    Val, Ile, or Phe"

(ix) FEATURE:
                (A) NAME/KEY: Modified-site
                (B) LOCATION: 113
                (D) OTHER INFORMATION: /note= "Xaa at position 113 is Phe,
                    Ala, Val, Leu, Ile, Trp, or Met"

(ix) FEATURE:

(A) NAME/KEY: Modified-site
(B) LOCATION: 114
(D) OTHER INFORMATION: /note= "Xaa at position 114 is Phe, Ala, Val, Leu, Ile, Trp, or Met"

(ix) FEATURE:
(A) NAME/KEY: Modified-site
(B) LOCATION: 115
(D) OTHER INFORMATION: /note= "Xaa at position 115 is Asn"

(ix) FEATURE:
(A) NAME/KEY: Modified-site
(B) LOCATION: 122
(D) OTHER INFORMATION: /note= "Xaa at position 122 is Arg, His, Glu, or Asp"

(xi) SEQUENCE DESCRIPTION: SEQ ID NO: 16:

```
Ser Pro Ala Pro Pro Ala Cys Asp Leu Arg Val Leu Ser Lys Leu Leu
 1               5                  10                  15

Arg Asp Ser His Val Leu His Ser Arg Leu Ser Gln Cys Pro Glu Val
            20                  25                  30

His Pro Leu Pro Xaa Pro Val Leu Leu Pro Ala Val Asp Xaa Xaa Leu
        35                  40                  45

Gly Glu Trp Lys Thr Gln Met Glu Glu Thr Lys Ala Gln Asp Ile Leu
    50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Xaa
                100                 105                 110

Xaa Xaa Xaa Gly Arg Thr Thr Ala His Xaa Asp Pro Asn Ala Ile Phe
        115                 120                 125

Leu Ser Phe Gln His Leu Leu Arg Gly Lys Val Arg Phe Leu Met Leu
        130                 135                 140

Val Gly Gly Ser Thr Leu Cys Val Arg
145                 150
```

(2) INFORMATION FOR SEQ ID NO: 17:

(i) SEQUENCE CHARACTERISTICS:
(A) LENGTH: 153 amino acids
(B) TYPE: amino acid
(C) STRANDEDNESS:
(D) TOPOLOGY: linear (ii) MOLECULE TYPE: protein (ix) FEATURE:
(A) NAME/KEY: Modified-site
(B) LOCATION: 37
(D) OTHER INFORMATION: /note= "Xaa at position 37 is Thr, Asp, or Glu"

(ix) FEATURE:
(A) NAME/KEY: Modified-site
(B) LOCATION: 46
(D) OTHER INFORMATION: /note= "Xaa at position 46 is Phe, Ala, Val, Leu, Ile, Pro, Trp, or Met"

(ix) FEATURE:
(A) NAME/KEY: Modified-site
(B) LOCATION: 47
(D) OTHER INFORMATION: /note= "Xaa at position 47 is Ser, Asp, or Glu"

(ix) FEATURE:
(A) NAME/KEY: Modified-site (B) LOCATION: 112
                (D) OTHER INFORMATION: /note= "Xaa at position 112 is
                    deleted or Leu, Ala, Val, Ile, Pro, Phe, Trp, or Met"

(ix) FEATURE:
                (A) NAME/KEY: Modified-site
                (B) LOCATION: 113
                (D) OTHER INFORMATION: /note= "Xaa at position 113 is
                    deleted or Pro, Phe, Ala, Val, Leu, Ile, Trp, or Met"

(ix) FEATURE:
                (A) NAME/KEY: Modified-site
                (B) LOCATION: 114
                (D) OTHER INFORMATION: /note= "Xaa at position 114 is
                    deleted or Pro, Phe, Ala, Val, Leu, Ile, Trp, or Met"

(ix) FEATURE:
                (A) NAME/KEY: Modified-site
                (B) LOCATION: 115
                (D) OTHER INFORMATION: /note= "Xaa at position 115 is
                    deleted or Gln, Gly, Ser, Thr, Tyr, or Asn"

(ix) FEATURE:
                (A) NAME/KEY: Modified-site
                (B) LOCATION: 122
                (D) OTHER INFORMATION: /note= "Xaa at position 122 is Lys,
                    Arg, His, Glu, or Asp"

(xi) SEQUENCE DESCRIPTION: SEQ ID NO: 17:

Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
            20                  25                  30

His Pro Leu Pro Xaa Pro Val Leu Leu Pro Ala Val Asp Xaa Xaa Leu
        35                  40                  45

Gly Glu Trp Lys Thr Gln Met Glu Glu Thr Lys Ala Gln Asp Ile Leu
    50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Xaa
                100                 105                 110

Xaa Xaa Xaa Gly Arg Thr Thr Ala His Xaa Asp Pro Asn Ala Ile Phe
        115                 120                 125

Leu Ser Phe Gln His Leu Leu Arg Gly Lys Val Arg Phe Leu Met Leu
        130                 135                 140

Val Gly Gly Ser Thr Leu Cys Val Arg
145                 150

(2) INFORMATION FOR SEQ ID NO: 18:

(i) SEQUENCE CHARACTERISTICS:
            (A) LENGTH: 153 amino acids
            (B) TYPE: amino acid
            (C) STRANDEDNESS:
            (D) TOPOLOGY: linear (ii) MOLECULE TYPE: protein (ix) FEATURE:
            (A) NAME/KEY: Modified-site
            (B) LOCATION: 37
            (D) OTHER INFORMATION: /note= "Xaa at position 37 is Thr,
                Asp, or Glu"

(ix) FEATURE:
            (A) NAME/KEY: Modified-site

```
        (B) LOCATION: 46
        (D) OTHER INFORMATION: /note= "Xaa at position 46 is Ala,
            Val, Leu, or Ile"

(ix) FEATURE:
        (A) NAME/KEY: Modified-site
        (B) LOCATION: 47
        (D) OTHER INFORMATION: /note= "Xaa at position 47 is Ser,
            Asp, or Glu"

(ix) FEATURE:
        (A) NAME/KEY: Modified-site
        (B) LOCATION: 112
        (D) OTHER INFORMATION: /note= "Xaa at position 112 is
            deleted or Ala, Val, Ile, or Phe"

(ix) FEATURE:
        (A) NAME/KEY: Modified-site
        (B) LOCATION: 113
        (D) OTHER INFORMATION: /note= "Xaa at position 113 is
            deleted or Phe, Ala, Val, Leu, Ile, Trp, or Met"

(ix) FEATURE:
        (A) NAME/KEY: Modified-site
        (B) LOCATION: 114
        (D) OTHER INFORMATION: /note= "Xaa at position 114 is
            deleted or Phe, Ala, Val, Leu, Ile, Trp, or Met"

(ix) FEATURE:
        (A) NAME/KEY: Modified-site
        (B) LOCATION: 115
        (D) OTHER INFORMATION: /note= "Xaa at position 115 is
            deleted or Asn"

(ix) FEATURE:
        (A) NAME/KEY: Modified-site
        (B) LOCATION: 122
        (D) OTHER INFORMATION: /note= "Xaa at position 122 is Arg,
            His, Glu, or Asp"

(xi) SEQUENCE DESCRIPTION: SEQ ID NO: 18:

Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
            20                  25                  30

His Pro Leu Pro Xaa Pro Val Leu Leu Pro Ala Val Asp Xaa Xaa Leu
        35                  40                  45

Gly Glu Trp Lys Thr Gln Met Glu Glu Thr Lys Ala Gln Asp Ile Leu
    50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
            85                  90                  95

Val Arg Leu Leu Leu Gly Ala Leu Gln Ser Leu Leu Gly Thr Gln Xaa
            100                 105                 110

Xaa Xaa Xaa Gly Arg Thr Thr Ala His Xaa Asp Pro Asn Ala Ile Phe
        115                 120                 125

Leu Ser Phe Gln His Leu Leu Arg Gly Lys Val Arg Phe Leu Met Leu
    130                 135                 140

Val Gly Gly Ser Thr Leu Cys Val Arg
145                 150

(2) INFORMATION FOR SEQ ID NO: 19:

(i) SEQUENCE CHARACTERISTICS:
        (A) LENGTH: 153 amino acids
        (B) TYPE: amino acid
        (C) STRANDEDNESS:
```

```
        (D) TOPOLOGY: linear (ii) MOLECULE TYPE: protein (ix) FEATURE:
        (A) NAME/KEY: Modified-site
        (B) LOCATION: 37
        (D) OTHER INFORMATION: /note= "Xaa at position 37 is Thr,
            Asp, or Glu"

(ix) FEATURE:
        (A) NAME/KEY: Modified-site
        (B) LOCATION: 46
        (D) OTHER INFORMATION: /note= "Xaa at position 46 is Ala,
            Val, Leu, or Ile"

(ix) FEATURE:
        (A) NAME/KEY: Modified-site
        (B) LOCATION: 47
        (D) OTHER INFORMATION: /note= "Xaa at position 47 is Ser,
            Asp, or Glu"

(ix) FEATURE:
        (A) NAME/KEY: Modified-site
        (B) LOCATION: 112
        (D) OTHER INFORMATION: /note= "Xaa at position 112 is Ala,
            Val, Ile, or Phe"

(ix) FEATURE:
        (A) NAME/KEY: Modified-site
        (B) LOCATION: 113
        (D) OTHER INFORMATION: /note= "Xaa at position 113 is Pro,
            Phe, Ala, Val, Leu, Ile, Trp, or Met"

(ix) FEATURE:
        (A) NAME/KEY: Modified-site
        (B) LOCATION: 114
        (D) OTHER INFORMATION: /note= "Xaa at position 114 is Pro,
            Phe, Ala, Val, Leu, Ile, Trp, or Met"

(ix) FEATURE:
        (A) NAME/KEY: Modified-site
        (B) LOCATION: 115
        (D) OTHER INFORMATION: /note= "Xaa at position 115 is Asn"

(ix) FEATURE:
        (A) NAME/KEY: Modified-site
        (B) LOCATION: 122
        (D) OTHER INFORMATION: /note= "Xaa at position 122 is Arg,
            His, Glu, or Asp"

(xi) SEQUENCE DESCRIPTION: SEQ ID NO: 19:

Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
                20                  25                  30

His Pro Leu Pro Xaa Pro Val Leu Leu Pro Ala Val Asp Xaa Xaa Leu
            35                  40                  45

Gly Glu Trp Lys Thr Gln Met Glu Glu Thr Lys Ala Gln Asp Ile Leu
50                  55                  60

Gly Ala Val Thr Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Xaa
                100                 105                 110

Xaa Xaa Xaa Gly Arg Thr Thr Ala His Xaa Asp Pro Asn Ala Ile Phe
        115                 120                 125

Leu Ser Phe Gln His Leu Leu Arg Gly Lys Val Arg Phe Leu Met Leu
130                 135                 140
```

```
Val Gly Gly Ser Thr Leu Cys Val Arg
145                 150
```

(2) INFORMATION FOR SEQ ID NO: 20:

(i) SEQUENCE CHARACTERISTICS:
        (A) LENGTH: 153 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Modified-site
        (B) LOCATION: 37
        (D) OTHER INFORMATION: /note= "Xaa at position 37 is Thr,
            Asp, or Glu"

(ix) FEATURE:
        (A) NAME/KEY: Modified-site
        (B) LOCATION: 46
        (D) OTHER INFORMATION: /note= "Xaa at position 46 is Leu or
            Phe"

(ix) FEATURE:
        (A) NAME/KEY: Modified-site
        (B) LOCATION: 47
        (D) OTHER INFORMATION: /note= "Xaa at position 47 is Ser,
            Asp, or Glu"

(ix) FEATURE:
        (A) NAME/KEY: Modified-site
        (B) LOCATION: 112
        (D) OTHER INFORMATION: /note= "Xaa at position 112 is
            deleted or Leu"

(ix) FEATURE:
        (A) NAME/KEY: Modified-site
        (B) LOCATION: 113
        (D) OTHER INFORMATION: /note= "Xaa at position 113 is
            deleted or Pro"

(ix) FEATURE:
        (A) NAME/KEY: Modified-site
        (B) LOCATION: 114
        (D) OTHER INFORMATION: /note= "Xaa at position 114 is
            deleted or Pro"

(ix) FEATURE:
        (A) NAME/KEY: Modified-site
        (B) LOCATION: 115
        (D) OTHER INFORMATION: /note= "Xaa at position 115 is
            deleted or Gln"

(ix) FEATURE:
        (A) NAME/KEY: Modified-site
        (B) LOCATION: 122
        (D) OTHER INFORMATION: /note= "Xaa at position 122 is Lys or
            Glu"

(xi) SEQUENCE DESCRIPTION: SEQ ID NO: 20:

```
Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
                20                  25                  30

His Pro Leu Pro Xaa Pro Val Leu Leu Pro Ala Val Asp Xaa Xaa Leu
                35                  40                  45

Gly Glu Trp Lys Thr Gln Met Glu Glu Thr Lys Ala Gln Asp Ile Leu
            50                  55                  60

Gly Ala Val Thr Leu Leu Leu Glu Gly Val Met Ala Ala Arg Gly Gln
65                  70                  75                  80
```

```
Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Xaa
            100                 105                 110

Xaa Xaa Xaa Gly Arg Thr Thr Ala His Xaa Asp Pro Asn Ala Ile Phe
        115                 120                 125

Leu Ser Phe Gln His Leu Leu Arg Gly Lys Val Arg Phe Leu Met Leu
    130                 135                 140

Val Gly Gly Ser Thr Leu Cys Val Arg
145                 150
```

(2) INFORMATION FOR SEQ ID NO: 21:

(i) SEQUENCE CHARACTERISTICS:
        (A) LENGTH: 153 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Modified-site
        (B) LOCATION: 37
        (D) OTHER INFORMATION: /note= "Xaa at position 37 is Thr,
            Asp, or Glu"

(ix) FEATURE:
        (A) NAME/KEY: Modified-site
        (B) LOCATION: 46
        (D) OTHER INFORMATION: /note= "Xaa at position 46 is Leu"

(ix) FEATURE:
        (A) NAME/KEY: Modified-site
        (B) LOCATION: 47
        (D) OTHER INFORMATION: /note= "Xaa at position 47 is Ser,
            Asp, or Glu"

(ix) FEATURE:
        (A) NAME/KEY: Modified-site
        (B) LOCATION: 112
        (D) OTHER INFORMATION: /note= "Xaa at position 112 is Leu"

(ix) FEATURE:
        (A) NAME/KEY: Modified-site
        (B) LOCATION: 113
        (D) OTHER INFORMATION: /note= "Xaa at position 113 is Pro"

(ix) FEATURE:
        (A) NAME/KEY: Modified-site
        (B) LOCATION: 114
        (D) OTHER INFORMATION: /note= "Xaa at position 114 is Pro"

(ix) FEATURE:
        (A) NAME/KEY: Modified-site
        (B) LOCATION: 115
        (D) OTHER INFORMATION: /note= "Xaa at position 115 is Gln"

(ix) FEATURE:
        (A) NAME/KEY: Modified-site
        (B) LOCATION: 122
        (D) OTHER INFORMATION: /note= "Xaa at position 122 is Glu"

(xi) SEQUENCE DESCRIPTION: SEQ ID NO: 21:

```
Ser Pro Ala Pro Pro Ala Cys Asp Leu Arg Val Leu Ser Lys Leu Leu
1               5                  10                  15

Arg Asp Ser His Val Leu His Ser Arg Leu Ser Gln Cys Pro Glu Val
            20                  25                  30

His Pro Leu Pro Xaa Pro Val Leu Leu Pro Ala Val Asp Xaa Xaa Leu
        35                  40                  45
```

```
Gly Glu Trp Lys Thr Gln Met Glu Glu Thr Lys Ala Gln Asp Ile Leu
 50                  55                  60

Gly Ala Val Thr Leu Leu Glu Gly Val Met Ala Ala Arg Gly Gln
 65                  70                  75                  80

Leu Gly Pro Thr Cys Leu Ser Ser Leu Leu Gly Gln Leu Ser Gly Gln
                 85                  90                  95

Val Arg Leu Leu Leu Gly Ala Leu Gln Ser Leu Leu Gly Thr Gln Xaa
             100                 105                 110

Xaa Xaa Xaa Gly Arg Thr Thr Ala His Xaa Asp Pro Asn Ala Ile Phe
         115                 120                 125

Leu Ser Phe Gln His Leu Leu Arg Gly Lys Val Arg Phe Leu Met Leu
130                 135                 140

Val Gly Gly Ser Thr Leu Cys Val Arg
145                 150
```

(2) INFORMATION FOR SEQ ID NO: 22:

(i) SEQUENCE CHARACTERISTICS:
  (A) LENGTH: 332 amino acids
  (B) TYPE: amino acid
  (C) STRANDEDNESS:
  (D) TOPOLOGY: linear (ii) MOLECULE TYPE: protein (ix) FEATURE:
  (A) NAME/KEY: Modified-site
  (B) LOCATION: 46
  (D) OTHER INFORMATION: /note= "Xaa at position 46 is Phe or Leu"

(ix) FEATURE:
  (A) NAME/KEY: Modified-site
  (B) LOCATION: 122
  (D) OTHER INFORMATION: /note= "Xaa at position 122 is Lys or Glu"

(ix) FEATURE:
  (A) NAME/KEY: Modified-site
  (B) LOCATION: 200
  (D) OTHER INFORMATION: /note= "Xaa at position 200 is Trp or Arg"

(xi) SEQUENCE DESCRIPTION: SEQ ID NO: 22:

```
Ser Pro Ala Pro Pro Ala Cys Asp Leu Arg Val Leu Ser Lys Leu Leu
 1                   5                  10                  15

Arg Asp Ser His Val Leu His Ser Arg Leu Ser Gln Cys Pro Glu Val
                 20                  25                  30

His Pro Leu Pro Thr Pro Val Leu Leu Pro Ala Val Asp Xaa Ser Leu
             35                  40                  45

Gly Glu Trp Lys Thr Gln Met Glu Glu Thr Lys Ala Gln Asp Ile Leu
 50                  55                  60

Gly Ala Val Thr Leu Leu Glu Gly Val Met Ala Ala Arg Gly Gln
 65                  70                  75                  80

Leu Gly Pro Thr Cys Leu Ser Ser Leu Leu Gly Gln Leu Ser Gly Gln
                 85                  90                  95

Val Arg Leu Leu Leu Gly Ala Leu Gln Ser Leu Leu Gly Thr Gln Leu
             100                 105                 110

Pro Pro Gln Gly Arg Thr Thr Ala His Xaa Asp Pro Asn Ala Ile Phe
         115                 120                 125

Leu Ser Phe Gln His Leu Leu Arg Gly Lys Val Arg Phe Leu Met Leu
130                 135                 140
```

```
Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu Pro Asn
                165                 170                 175

Arg Thr Ser Gly Leu Leu Glu Thr Asn Phe Thr Ala Ser Ala Arg Thr
            180                 185                 190

Thr Gly Ser Gly Leu Leu Lys Xaa Gln Gln Gly Phe Arg Ala Lys Ile
            195                 200                 205

Pro Gly Leu Leu Asn Gln Thr Ser Arg Ser Leu Asp Gln Ile Pro Gly
        210                 215                 220

Tyr Leu Asn Arg Ile His Glu Leu Leu Asn Gly Thr Arg Gly Leu Phe
225                 230                 235                 240

Pro Gly Pro Ser Arg Arg Thr Leu Gly Ala Pro Asp Ile Ser Ser Gly
                245                 250                 255

Thr Ser Asp Thr Gly Ser Leu Pro Pro Asn Leu Gln Pro Gly Tyr Ser
            260                 265                 270

Pro Ser Pro Thr His Pro Pro Thr Gly Gln Tyr Thr Leu Phe Pro Leu
            275                 280                 285

Pro Pro Thr Leu Pro Thr Pro Val Val Gln Leu His Pro Leu Leu Pro
290                 295                 300

Asp Pro Ser Ala Pro Thr Pro Thr Pro Thr Ser Pro Leu Leu Asn Thr
305                 310                 315                 320

Ser Tyr Thr His Ser Gln Asn Leu Ser Gln Glu Gly
            325                 330
```

(2) INFORMATION FOR SEQ ID NO: 23:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(iv) ANTI-SENSE: YES (xi) SEQUENCE DESCRIPTION: SEQ ID NO: 23:

```
AATAGCTGAA TTCTTACCCT TCCTGAGACA GATT                                34
```

(2) INFORMATION FOR SEQ ID NO: 24:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 24:

```
CATGGCAAGA TCTCCGGCCA GAATGGAGCT GACTGAA                             37
```

(2) INFORMATION FOR SEQ ID NO: 25:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO: 25:

ACGTCCATGG CNTCNCCNGC NCCNCCTGCT TGTGACCTCC GAGTC                      45

(2) INFORMATION FOR SEQ ID NO: 26:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO: 26:

TGACAAGCTT ACCTGACGCA GAGGGTGGAC CCT                                   33

(2) INFORMATION FOR SEQ ID NO: 27:

(i) SEQUENCE CHARACTERISTICS:
            (A) LENGTH: 64 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO: 27:

GGATCCACCA TGAGCCGCCT GCCCGTCCTG CTCCTGCTCC AACTCCTGGT CCGCCCCGCC      60

ATGG                                                                  64

(2) INFORMATION FOR SEQ ID NO: 28:

(i) SEQUENCE CHARACTERISTICS:
            (A) LENGTH: 18 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO: 28:

Met Ser Arg Leu Pro Val Leu Leu Leu Leu Gln Leu Leu Val Arg Pro
1               5                   10                  15
Ala Met (2) INFORMATION FOR SEQ ID NO: 29:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO: 29:

ATGCACGAAT TCCCTGACGC AGAGGGTGGA                                       30

(2) INFORMATION FOR SEQ ID NO: 30:

(i) SEQUENCE CHARACTERISTICS:

```
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 30:

AATTCCATGC ATAC                                                              14

(2) INFORMATION FOR SEQ ID NO: 31:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 31:

GTATGCATGG                                                                   10

(2) INFORMATION FOR SEQ ID NO: 32:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 32:

AATTCCATCA CCATCACCAT CACT                                                   24

(2) INFORMATION FOR SEQ ID NO: 33:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 33:

AATTAGTGAT GGTGATGGTG ATGG                                                   24

(2) INFORMATION FOR SEQ ID NO: 34:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 34:

CATGCATCAC CATCACCATC ACGC                                                   24

(2) INFORMATION FOR SEQ ID NO: 35:
```

```
    (i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 35:

CATGGCGTGA TGGTGATGGT GATG                                                   24

(2) INFORMATION FOR SEQ ID NO: 36:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 36:

His His His His His His Ala Met Ala
1               5

(2) INFORMATION FOR SEQ ID NO: 37:

(i) SEQUENCE CHARACTERISTICS:
        (A) LENGTH: 328 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 37:

Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
                20                  25                  30

His Pro Leu Pro Thr Pro Val Leu Leu Pro Ala Val Asp Phe Ser Leu
            35                  40                  45

Gly Glu Trp Lys Thr Gln Met Glu Glu Thr Lys Ala Gln Asp Ile Leu
        50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Gly
                100                 105                 110

Arg Thr Thr Ala His Lys Asp Pro Asn Ala Ile Phe Leu Ser Phe Gln
            115                 120                 125

His Leu Leu Arg Gly Lys Val Arg Phe Leu Met Leu Val Gly Gly Ser
        130                 135                 140

Thr Leu Cys Val Arg Arg Ala Pro Pro Thr Thr Ala Val Pro Ser Arg
145                 150                 155                 160

Thr Ser Leu Val Leu Thr Leu Asn Glu Leu Pro Asn Arg Thr Ser Gly
                165                 170                 175

Leu Leu Glu Thr Asn Phe Thr Ala Ser Ala Arg Thr Thr Gly Ser Gly
                180                 185                 190

Leu Leu Lys Trp Gln Gln Gly Phe Arg Ala Lys Ile Pro Gly Leu Leu
```

-continued

```
                  195                 200                      205
Asn Gln Thr Ser Arg Ser Leu Asp Gln Ile Pro Gly Tyr Leu Asn Arg
        210                 215                 220
Ile His Glu Leu Leu Asn Gly Thr Arg Gly Leu Phe Pro Gly Pro Ser
225                 230                 235                 240
Arg Arg Thr Leu Gly Ala Pro Asp Ile Ser Ser Gly Thr Ser Asp Thr
                245                 250                 255
Gly Ser Leu Pro Pro Asn Leu Gln Pro Gly Tyr Ser Pro Ser Pro Thr
                260                 265                 270
His Pro Pro Thr Gly Gln Tyr Thr Leu Phe Pro Leu Pro Pro Thr Leu
                275                 280                 285
Pro Thr Pro Val Val Gln Leu His Pro Leu Leu Pro Asp Pro Ser Ala
                290                 295                 300
Pro Thr Pro Thr Pro Thr Ser Pro Leu Leu Asn Thr Ser Tyr Thr His
305                 310                 315                 320
Ser Gln Asn Leu Ser Gln Glu Gly
                325
```

(2) INFORMATION FOR SEQ ID NO: 38:

(i) SEQUENCE CHARACTERISTICS:
        (A) LENGTH: 149 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 38:

```
Ser Pro Ala Pro Pro Ala Cys Asp Leu Arg Val Leu Ser Lys Leu Leu
1               5                   10                  15
Arg Asp Ser His Val Leu His Ser Arg Leu Ser Gln Cys Pro Glu Val
                20                  25                  30
His Pro Leu Pro Thr Pro Val Leu Leu Pro Ala Val Asp Phe Ser Leu
                35                  40                  45
Gly Glu Trp Lys Thr Gln Met Glu Glu Thr Lys Ala Gln Asp Ile Leu
50                  55                  60
Gly Ala Val Thr Leu Leu Leu Glu Gly Val Met Ala Ala Arg Gly Gln
65                  70                  75                  80
Leu Gly Pro Thr Cys Leu Ser Ser Leu Leu Gly Gln Leu Ser Gly Gln
                85                  90                  95
Val Arg Leu Leu Leu Gly Ala Leu Gln Ser Leu Leu Gly Thr Gln Gly
                100                 105                 110
Arg Thr Thr Ala His Lys Asp Pro Asn Ala Ile Phe Leu Ser Phe Gln
                115                 120                 125
His Leu Leu Arg Gly Lys Val Arg Phe Leu Met Leu Val Gly Gly Ser
                130                 135                 140
Thr Leu Cys Val Arg
145
```

(2) INFORMATION FOR SEQ ID NO: 39:

(i) SEQUENCE CHARACTERISTICS:
        (A) LENGTH: 984 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 39:

```
AGCCCGGCTC CTCCTGCTTG TGACCTCCGA GTCCTCAGTA AACTGCTTCG TGACTCCCAT      60
GTCCTTCACA GCAGACTGAG CCAGTGCCCA GAGGTTCACC CTTTGCCTAC ACCTGTCCTG     120
CTGCCTGCTG TGGACTTTAG CTTGGGAGAA TGGAAAACCC AGATGGAGGA GACCAAGGCA     180
CAGGACATTC TGGGAGCAGT GACCCTTCTG CTGGAGGGAG TGATGGCAGC ACGGGGACAA     240
CTGGGACCCA CTTGCCTCTC ATCCCTCCTG GGGCAGCTTT CTGGACAGGT CCGTCTCCTC     300
CTTGGGGCCC TGCAGAGCCT CCTTGGAACC CAGGGCAGGA CCACAGCTCA CAAGGATCCC     360
AATGCCATCT TCCTGAGCTT CCAACACCTG CTCCGAGGAA AGGTGCGTTT CCTGATGCTT     420
GTAGGAGGGT CCACCCTCTG CGTCAGGCGG GCCCCACCCA CCACAGCTGT CCCCAGCAGA     480
ACCTCTCTAG TCCTCACACT GAACGAGCTC CCAAACAGGA CTTCTGGATT GTTGGAGACA     540
AACTTCACTG CCTCAGCCAG AACTACTGGC TCTGGGCTTC TGAAGTGGCA GCAGGGATTC     600
AGAGCCAAGA TTCCTGGTCT GCTGAACCAA ACCTCCAGGT CCCTGGACCA AATCCCCGGA     660
TACCTGAACA GGATACACGA ACTCTTGAAT GGAACTCGTG GACTCTTTCC TGGACCCTCA     720
CGCAGGACCC TAGGAGCCCC GGACATTTCC TCAGGAACAT CAGACACAGG CTCCCTGCCA     780
CCCAACCTCC AGCCTGGATA TTCTCCTTCC CCAACCCATC CTCCTACTGG ACAGTATACG     840
CTCTTCCCTC TTCCACCCAC CTTGCCCACC CCTGTGGTCC AGCTCCACCC CCTGCTTCCT     900
GACCCTTCTG CTCCAACGCC CACCCCTACC AGCCCTCTTC TAAACACATC CTACACCCAC     960
TCCCAGAATC TGTCTCAGGA AGGG                                            984
```

(2) INFORMATION FOR SEQ ID NO: 40:

(i) SEQUENCE CHARACTERISTICS:
        (A) LENGTH: 447 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 40:

```
TCCCCTGCTC CGCCTGCTTG TGACCTCCGA GTCCTCAGTA AACTGCTTCG TGACTCCCAT      60
GTCCTTCACA GCAGACTGAG CCAGTGCCCA GAGGTTCACC CTTTGCCTAC ACCTGTCCTG     120
CTGCCTGCTG TGGACTTTAG CTTGGGAGAA TGGAAAACCC AGATGGAGGA GACCAAGGCA     180
CAGGACATTC TGGGAGCAGT GACCCTTCTG CTGGAGGGAG TGATGGCAGC ACGGGGACAA     240
CTGGGACCCA CTTGCCTCTC ATCCCTCCTG GGGCAGCTTT CTGGACAGGT CCGTCTCCTC     300
CTTGGGGCCC TGCAGAGCCT CCTTGGAACC CAGGGCAGGA CCACAGCTCA CAAGGATCCC     360
AATGCCATCT TCCTGAGCTT CCAACACCTG CTCCGAGGAA AGGTGCGTTT CCTGATGCTT     420
GTAGGAGGGT CCACCCTCTG CGTCAGG                                         447
```

(2) INFORMATION FOR SEQ ID NO: 41:

(i) SEQUENCE CHARACTERISTICS:
        (A) LENGTH: 392 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 41:

-continued

```
Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
            35                  40                  45

Gly Glu Trp Lys Thr Gln Met Glu Glu Thr Lys Ala Gln Asp Ile Leu
    50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Gly
                100                 105                 110

Arg Thr Thr Ala His Lys Asp Pro Asn Ala Ile Phe Leu Ser Phe Gln
                115                 120                 125

His Leu Leu Arg Gly Lys Val Arg Phe Leu Met Leu Val Gly Gly Ser
            130                 135                 140

Thr Leu Cys Val Arg Glu Phe Ile Glu Gly Arg Gln Phe Lys Leu Glu
145                 150                 155                 160

Pro Arg Gly Pro Thr Ile Lys Pro Cys Pro Pro Cys Lys Cys Pro Ala
                165                 170                 175

Pro Asn Leu Leu Gly Gly Pro Ser Val Phe Ile Phe Pro Pro Lys Ile
                180                 185                 190

Lys Asp Val Leu Met Ile Ser Leu Ser Pro Ile Val Thr Cys Val Val
            195                 200                 205

Val Asp Val Ser Glu Asp Asp Pro Asp Val Gln Ile Ser Trp Phe Val
            210                 215                 220

Asn Asn Val Glu Val His Thr Ala Gln Thr Gln Thr His Arg Glu Asp
225                 230                 235                 240

Tyr Asn Ser Thr Leu Arg Val Val Ser Ala Leu Pro Ile Gln His Gln
                245                 250                 255

Asp Trp Met Ser Gly Lys Glu Phe Lys Cys Lys Val Asn Asn Lys Asp
                260                 265                 270

Leu Pro Ala Pro Ile Glu Arg Thr Ile Ser Lys Pro Lys Gly Ser Val
            275                 280                 285

Arg Ala Pro Gln Val Tyr Val Leu Pro Pro Pro Glu Glu Glu Met Thr
290                 295                 300

Lys Lys Gln Val Thr Leu Thr Cys Met Val Thr Asp Phe Met Pro Glu
305                 310                 315                 320

Asp Ile Tyr Val Glu Trp Thr Asn Asn Gly Lys Thr Glu Leu Asn Tyr
                325                 330                 335

Lys Asn Thr Glu Pro Val Leu Asp Ser Asp Gly Ser Tyr Phe Met Tyr
            340                 345                 350

Ser Lys Leu Arg Val Glu Lys Lys Asn Trp Val Glu Arg Asn Ser Tyr
            355                 360                 365

Ser Cys Ser Val Val His Glu Gly Leu His Asn His Thr Thr Lys
            370                 375                 380

Ser Phe Ser Arg Thr Pro Gly Lys
385                 390
```

(2) INFORMATION FOR SEQ ID NO: 42:

(i) SEQUENCE CHARACTERISTICS:

(A) LENGTH: 386 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO: 42:

```
Ser Pro Ala Pro Pro Ala Cys Asp Leu Arg Val Leu Ser Lys Leu Leu
 1               5                  10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
        35                  40                  45

Gly Glu Trp Lys Thr Gln Met Glu Glu Thr Lys Ala Gln Asp Ile Leu
 50                      55                      60

Gly Ala Val Thr Leu Leu Leu Glu Gly Val Met Ala Ala Arg Gly Gln
 65                  70                      75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Gly
            100                 105                 110

Arg Thr Thr Ala His Lys Asp Pro Asn Ala Ile Phe Leu Ser Phe Gln
            115                 120                 125

His Leu Leu Arg Gly Lys Val Arg Phe Leu Met Leu Val Gly Gly Ser
    130                 135                 140

Thr Leu Cys Val Arg Glu Phe Lys Leu Glu Pro Arg Gly Pro Thr Ile
145                 150                 155                 160

Lys Pro Cys Pro Pro Cys Lys Cys Pro Ala Pro Asn Leu Leu Gly Gly
                165                 170                 175

Pro Ser Val Phe Ile Phe Pro Pro Lys Ile Lys Asp Val Leu Met Ile
                180                 185                 190

Ser Leu Ser Pro Ile Val Thr Cys Val Val Val Asp Val Ser Glu Asp
            195                 200                 205

Asp Pro Asp Val Gln Ile Ser Trp Phe Val Asn Asn Val Glu Val His
    210                 215                 220

Thr Ala Gln Thr Gln Thr His Arg Glu Asp Tyr Asn Ser Thr Leu Arg
225                 230                 235                 240

Val Val Ser Ala Leu Pro Ile Gln His Gln Asp Trp Met Ser Gly Lys
                245                 250                 255

Glu Phe Lys Cys Lys Val Asn Asn Lys Asp Leu Pro Ala Pro Ile Glu
                260                 265                 270

Arg Thr Ile Ser Lys Pro Lys Gly Ser Val Arg Ala Pro Gln Val Tyr
            275                 280                 285

Val Leu Pro Pro Pro Glu Glu Glu Met Thr Lys Lys Gln Val Thr Leu
            290                 295                 300

Thr Cys Met Val Thr Asp Phe Met Pro Glu Asp Ile Tyr Val Glu Trp
305                 310                 315                 320

Thr Asn Asn Gly Lys Thr Glu Leu Asn Tyr Lys Asn Thr Glu Pro Val
                325                 330                 335

Leu Asp Ser Asp Gly Ser Tyr Phe Met Tyr Ser Lys Leu Arg Val Glu
            340                 345                 350

Lys Lys Asn Trp Val Glu Arg Asn Ser Tyr Ser Cys Ser Val Val His
            355                 360                 365

Glu Gly Leu His Asn His His Thr Thr Lys Ser Phe Ser Arg Thr Pro
```

```
                   370                 375                 380
Gly Lys
385

(2) INFORMATION FOR SEQ ID NO: 43:

(i) SEQUENCE CHARACTERISTICS:
        (A) LENGTH: 284 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 43:

Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
        35                  40                  45

Gly Glu Trp Lys Thr Gln Met Glu Glu Thr Lys Ala Gln Asp Ile Leu
    50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Gly
                100                 105                 110

Arg Thr Thr Ala His Lys Asp Pro Asn Ala Ile Phe Leu Ser Phe Gln
            115                 120                 125

His Leu Leu Arg Gly Lys Val Arg Phe Leu Met Leu Val Gly Gly Ser
        130                 135                 140

Thr Leu Cys Val Arg Glu Phe His Ala Tyr Val Ile Glu Gly Arg Ile
145                 150                 155                 160

Ser Pro Gly Gly Gly Ser Gly Gly Ser Asn Met Ala Asn Cys Ser
                165                 170                 175

Ile Met Ile Asp Glu Ile Ile His His Leu Lys Arg Pro Pro Asn Pro
                180                 185                 190

Leu Leu Asp Pro Asn Asn Leu Asn Ser Glu Asp Met Asp Ile Leu Met
            195                 200                 205

Glu Arg Asn Leu Arg Thr Pro Asn Leu Leu Ala Phe Val Arg Ala Val
        210                 215                 220

Lys His Leu Glu Asn Ala Ser Gly Ile Glu Ala Ile Leu Arg Asn Leu
225                 230                 235                 240

Gln Pro Cys Leu Pro Ser Ala Thr Ala Ala Pro Ser Arg His Pro Ile
                245                 250                 255

Ile Ile Lys Ala Gly Asp Trp Gln Glu Phe Arg Glu Lys Leu Thr Phe
                260                 265                 270

Tyr Leu Val Thr Leu Glu Gln Ala Gln Glu Gln Gln
            275                 280

(2) INFORMATION FOR SEQ ID NO: 44:

(i) SEQUENCE CHARACTERISTICS:
        (A) LENGTH: 284 amino acids
        (B) TYPE: amino acid
        (C) STRANDEDNESS:
```

```
            (D) TOPOLOGY: linear (ii) MOLECULE TYPE: protein (xi) SEQUENCE DESCRIPTION: SEQ ID NO: 44:

Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
                20                  25                  30

His Pro Leu Pro Thr Pro Val Leu Leu Pro Ala Val Asp Phe Ser Leu
            35                  40                  45

Gly Glu Trp Lys Thr Gln Met Glu Glu Thr Lys Ala Gln Asp Ile Leu
        50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Gly
                100                 105                 110

Arg Thr Thr Ala His Lys Asp Pro Asn Ala Ile Phe Leu Ser Phe Gln
            115                 120                 125

His Leu Leu Arg Gly Lys Val Arg Phe Leu Met Leu Val Gly Gly Ser
        130                 135                 140

Thr Leu Cys Val Arg Glu Phe His Ala Tyr Val Glu Gly Gly Gly Gly
145                 150                 155                 160

Ser Pro Gly Gly Gly Ser Gly Gly Ser Asn Met Ala Asn Cys Ser
                165                 170                 175

Ile Met Ile Asp Glu Ile Ile His His Leu Lys Arg Pro Pro Asn Pro
                180                 185                 190

Leu Leu Asp Pro Asn Asn Leu Asn Ser Glu Asp Met Asp Ile Leu Met
            195                 200                 205

Glu Arg Asn Leu Arg Thr Pro Asn Leu Leu Ala Phe Val Arg Ala Val
        210                 215                 220

Lys His Leu Glu Asn Ala Ser Gly Ile Glu Ala Ile Leu Arg Asn Leu
225                 230                 235                 240

Gln Pro Cys Leu Pro Ser Ala Thr Ala Ala Pro Ser Arg His Pro Ile
                245                 250                 255

Ile Ile Lys Ala Gly Asp Trp Gln Glu Phe Arg Glu Lys Leu Thr Phe
                260                 265                 270

Tyr Leu Val Thr Leu Glu Gln Ala Gln Glu Gln Gln
            275                 280

(2) INFORMATION FOR SEQ ID NO: 45:

(i) SEQUENCE CHARACTERISTICS:
        (A) LENGTH: 281 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 45:

Ala Asn Cys Ser Ile Met Ile Asp Glu Ile Ile His His Leu Lys Arg
1               5                   10                  15

Pro Pro Asn Pro Leu Leu Asp Pro Asn Asn Leu Asn Ser Glu Asp Met
                20                  25                  30
```

```
Asp Ile Leu Met Glu Arg Asn Leu Arg Thr Pro Asn Leu Leu Ala Phe
         35                  40                  45

Val Arg Ala Val Lys His Leu Glu Asn Ala Ser Gly Ile Glu Ala Ile
 50                  55                  60

Leu Arg Asn Leu Gln Pro Cys Leu Pro Ser Ala Thr Ala Ala Pro Ser
 65                  70                  75                  80

Arg His Pro Ile Ile Ile Lys Ala Gly Asp Trp Gln Glu Phe Arg Glu
                 85                  90                  95

Lys Leu Thr Phe Tyr Leu Val Thr Leu Glu Gln Ala Gln Glu Gln Gln
                100                 105                 110

Tyr Val Glu Gly Gly Gly Ser Pro Gly Gly Ser Gly Gly Gly
                115                 120                 125

Ser Asn Met Ala Ser Pro Ala Pro Pro Ala Cys Asp Leu Arg Val Leu
    130                 135                 140

Ser Lys Leu Leu Arg Asp Ser His Val Leu His Ser Arg Leu Ser Gln
145                 150                 155                 160

Cys Pro Glu Val His Pro Leu Pro Thr Pro Val Leu Leu Pro Ala Val
                165                 170                 175

Asp Phe Ser Leu Gly Glu Trp Lys Thr Gln Met Glu Glu Thr Lys Ala
                180                 185                 190

Gln Asp Ile Leu Gly Ala Val Thr Leu Leu Leu Glu Gly Val Met Ala
        195                 200                 205

Ala Arg Gly Gln Leu Gly Pro Thr Cys Leu Ser Ser Leu Leu Gly Gln
210                 215                 220

Leu Ser Gly Gln Val Arg Leu Leu Leu Gly Ala Leu Gln Ser Leu Leu
225                 230                 235                 240

Gly Thr Gln Gly Arg Thr Thr Ala His Lys Asp Pro Asn Ala Ile Phe
                245                 250                 255

Leu Ser Phe Gln His Leu Leu Arg Gly Lys Val Arg Phe Leu Met Leu
                260                 265                 270

Val Gly Gly Ser Thr Leu Cys Val Arg
        275                 280

(2) INFORMATION FOR SEQ ID NO: 46:

(i) SEQUENCE CHARACTERISTICS:
         (A) LENGTH: 157 amino acids
         (B) TYPE: amino acid
         (C) STRANDEDNESS:
         (D) TOPOLOGY: linear (ii) MOLECULE TYPE: protein (xi) SEQUENCE DESCRIPTION: SEQ ID NO: 46:

Ser Pro Ala Pro Pro Ala Cys Asp Leu Arg Val Leu Ser Lys Leu Leu
 1               5                  10                  15

Arg Asp Ser His Val Leu His Ser Arg Leu Ser Gln Cys Pro Glu Val
                 20                  25                  30

His Pro Leu Pro Thr Pro Val Leu Leu Pro Ala Val Asp Phe Ser Leu
         35                  40                  45

Gly Glu Trp Lys Thr Gln Met Glu Glu Thr Lys Ala Gln Asp Ile Leu
 50                  55                  60

Gly Ala Val Thr Leu Leu Leu Glu Gly Val Met Ala Ala Arg Gly Gln
 65                  70                  75                  80

Leu Gly Pro Thr Cys Leu Ser Ser Leu Leu Gly Gln Leu Ser Gly Gln
                 85                  90                  95
```

```
Val Arg Leu Leu Leu Gly Ala Leu Gln Ser Leu Leu Gly Thr Gln Gly
            100                 105                 110

Arg Thr Thr Ala His Lys Asp Pro Asn Ala Ile Phe Leu Ser Phe Gln
            115                 120                 125

His Leu Leu Arg Gly Lys Val Arg Phe Leu Met Leu Val Gly Gly Ser
            130                 135                 140

Thr Leu Cys Val Arg Glu Phe His His His His His
145                 150                 155
```

(2) INFORMATION FOR SEQ ID NO: 47:

(i) SEQUENCE CHARACTERISTICS:
        (A) LENGTH: 158 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 47:

```
His His His His His His Ala Met Ala Ser Pro Ala Pro Pro Ala Cys
1               5                   10                  15

Asp Leu Arg Val Leu Ser Lys Leu Leu Arg Asp Ser His Val Leu His
            20                  25                  30

Ser Arg Leu Ser Gln Cys Pro Glu Val His Pro Leu Pro Thr Pro Val
            35                  40                  45

Leu Leu Pro Ala Val Asp Phe Ser Leu Gly Glu Trp Lys Thr Gln Met
        50                  55                  60

Glu Glu Thr Lys Ala Gln Asp Ile Leu Gly Ala Val Thr Leu Leu Leu
65                  70                  75                  80

Glu Gly Val Met Ala Ala Arg Gly Gln Leu Gly Pro Thr Cys Leu Ser
            85                  90                  95

Ser Leu Leu Gly Gln Leu Ser Gly Gln Val Arg Leu Leu Leu Gly Ala
            100                 105                 110

Leu Gln Ser Leu Leu Gly Thr Gln Gly Arg Thr Thr Ala His Lys Asp
            115                 120                 125

Pro Asn Ala Ile Phe Leu Ser Phe Gln His Leu Leu Arg Gly Lys Val
            130                 135                 140

Arg Phe Leu Met Leu Val Gly Gly Ser Thr Leu Cys Val Arg
145                 150                 155
```

(2) INFORMATION FOR SEQ ID NO: 48:

(i) SEQUENCE CHARACTERISTICS:
        (A) LENGTH: 447 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 48:

```
TCTCCGGCGC CGCCTGCTTG TGACCTCCGA GTCCTCAGTA AACTGCTTCG TGACTCCCAT      60

GTCCTTCACA GCAGACTGAG CCAGTGCCCA GAGGTTCACC CTTTGCCTAC ACCTGTCCTG    120

CTGCCTGCTG TGGACTTTAG CTTGGGAGAA TGGAAAACCC AGATGGAGGA GACCAAGGCA    180

CAGGACATTC TGGGAGCAGT GACCCTTCTG CTGGAGGGAG TGATGGCAGC ACGGGGACAA    240

CTGGGACCCA CTTGCCTCTC ATCCCTCCTG GGGCAGCTTT CTGGACAGGT CCGTCTCCTC    300

CTTGGGGCCC TGCAGAGCCT CCTTGGAACC CAGGGCAGGA CCACAGCTCA CAAGGATCCC    360
```

```
AATGCCATCT TCCTGAGCTT CCAACACCTG CTCCGAGGAA AGGTGCGTTT CCTGATGCTT    420

GTAGGAGGGT CCACCCTCTG CGTCAGG                                       447

(2) INFORMATION FOR SEQ ID NO: 49:

(i) SEQUENCE CHARACTERISTICS:
        (A) LENGTH: 447 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 49:

TCGCCTGCAC CGCCTGCTTG TGACCTCCGA GTCCTCAGTA AACTGCTTCG TGACTCCCAT     60

GTCCTTCACA GCAGACTGAG CCAGTGCCCA GAGGTTCACC CTTTGCCTAC ACCTGTCCTG    120

CTGCCTGCTG TGGACTTTAG CTTGGGAGAA TGGAAAACCC AGATGGAGGA GACCAAGGCA    180

CAGGACATTC TGGGAGCAGT GACCCTTCTG CTGGAGGGAG TGATGGCAGC ACGGGGACAA    240

CTGGGACCCA CTTGCCTCTC ATCCCTCCTG GGGCAGCTTT CTGGACAGGT CCGTCTCCTC    300

CTTGGGGCCC TGCAGAGCCT CCTTGGAACC CAGGGCAGGA CCACAGCTCA CAAGGATCCC    360

AATGCCATCT TCCTGAGCTT CCAACACCTG CTCCGAGGAA AGGTGCGTTT CCTGATGCTT    420

GTAGGAGGGT CCACCCTCTG CGTCAGG                                       447

(2) INFORMATION FOR SEQ ID NO: 50:

(i) SEQUENCE CHARACTERISTICS:
        (A) LENGTH: 447 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 50:

TCCCCGGCCC CGCCTGCTTG TGACCTCCGA GTCCTCAGTA AACTGCTTCG TGACTCCCAT     60

GTCCTTCACA GCAGACTGAG CCAGTGCCCA GAGGTTCACC CTTTGCCTAC ACCTGTCCTG    120

CTGCCTGCTG TGGACTTTAG CTTGGGAGAA TGGAAAACCC AGATGGAGGA GACCAAGGCA    180

CAGGACATTC TGGGAGCAGT GACCCTTCTG CTGGAGGGAG TGATGGCAGC ACGGGGACAA    240

CTGGGACCCA CTTGCCTCTC ATCCCTCCTG GGGCAGCTTT CTGGACAGGT CCGTCTCCTC    300

CTTGGGGCCC TGCAGAGCCT CCTTGGAACC CAGGGCAGGA CCACAGCTCA CAAGGATCCC    360

AATGCCATCT TCCTGAGCTT CCAACACCTG CTCCGAGGAA AGGTGCGTTT CCTGATGCTT    420

GTAGGAGGGT CCACCCTCTG CGTCAGG                                       447

(2) INFORMATION FOR SEQ ID NO: 51:

(i) SEQUENCE CHARACTERISTICS:
        (A) LENGTH: 1158 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 51:

TCTCCGGCGC CGCCTGCTTG TGACCTCCGA GTCCTCAGTA AACTGCTTCG TGACTCCCAT     60

GTCCTTCACA GCAGACTGAG CCAGTGCCCA GAGGTTCACC CTTTGCCTAC ACCTGTCCTG    120
```

```
CTGCCTGCTG TGGACTTTAG CTTGGGAGAA TGGAAAACCC AGATGGAGGA GACCAAGGCA    180

CAGGACATTC TGGGAGCAGT GACCCTTCTG CTGGAGGGAG TGATGGCAGC ACGGGGACAA    240

CTGGGACCCA CTTGCCTCTC ATCCCTCCTG GGGCAGCTTT CTGGACAGGT CCGTCTCCTC    300

CTTGGGGCCC TGCAGAGCCT CCTTGGAACC CAGGGCAGGA CCACAGCTCA CAAGGATCCC    360

AATGCCATCT TCCTGAGCTT CCAACACCTG CTCCGAGGAA AGGTGCGTTT CCTGATGCTT    420

GTAGGAGGGT CCACCCTCTG CGTCAGGGAA TTCAAGCTTG AGCCCAGAGG GCCCACAATC    480

AAGCCCTGTC CTCCATGCAA ATGCCCAGCA CCTAACCTCT TGGGTGGACC ATCCGTCTTC    540

ATCTTCCCTC CAAAGATCAA GGATGTACTC ATGATCTCCC TGAGCCCCAT AGTCACATGT    600

GTGGTGGTGG ATGTGAGCGA GGATGACCCA GATGTCCAGA TCAGCTGGTT TGTGAACAAC    660

GTGGAAGTAC ACACAGCTCA GACACAAACC CATAGAGAGG ATTACAACAG TACTCTCCGG    720

GTGGTCAGTG CCCTCCCCAT CCAGCACCAG GACTGGATGA GTGGCAAGGA GTTCAAATGC    780

AAGGTCAACA ACAAAGACCT CCCAGCGCCC ATCGAGAGAA CCATCTCAAA ACCCAAAGGG    840

TCAGTAAGAG CTCCACAGGT ATATGTCTTG CCTCCACCAG AAGAAGAGAT GACTAAGAAA    900

CAGGTCACTC TGACCTGCAT GGTCACAGAC TTCATGCCTG AAGACATTTA CGTGGAGTGG    960

ACCAACAACG GGAAAACAGA GCTAAACTAC AAGAACACTG AACCAGTCCT GGACTCTGAT   1020

GGTTCTTACT TCATGTACAG CAAGCTGAGA GTGGAAAAGA GAACTGGGT GGAAAGAAAT   1080

AGCTACTCCT GTTCAGTGGT CCACGAGGGT CTGCACAATC ACCACACGAC TAAGAGCTTC   1140

TCCCGGACTC CGGGTAAA                                                 1158

(2) INFORMATION FOR SEQ ID NO: 52:

(i) SEQUENCE CHARACTERISTICS:
            (A) LENGTH: 852 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO: 52:

TCCCCGGCCC CGCCTGCTTG TGACCTCCGA GTCCTCAGTA AACTGCTTCG TGACTCCCAT     60

GTCCTTCACA GCAGACTGAG CCAGTGCCCA GAGGTTCACC CTTTGCCTAC ACCTGTCCTG    120

CTGCCTGCTG TGGACTTTAG CTTGGGAGAA TGGAAAACCC AGATGGAGGA GACCAAGGCA    180

CAGGACATTC TGGGAGCAGT GACCCTTCTG CTGGAGGGAG TGATGGCAGC ACGGGGACAA    240

CTGGGACCCA CTTGCCTCTC ATCCCTCCTG GGGCAGCTTT CTGGACAGGT CCGTCTCCTC    300

CTTGGGGCCC TGCAGAGCCT CCTTGGAACC CAGGGCAGGA CCACAGCTCA CAAGGATCCC    360

AATGCCATCT TCCTGAGCTT CCAACACCTG CTCCGAGGAA AGGTGCGTTT CCTGATGCTT    420

GTAGGAGGGT CCACCCTCTG CGTCAGGGAA TTCCATGCAT ACGTAATCGA GGGAAGGATT    480

TCCCCGGGTG GTGGTTCTGG CGGCGGCTCC AACATGGCTA ACTGCTCTAT AATGATCGAT    540

GAAATTATAC ATCACTTAAA GAGACCACCT AACCCTTTGC TGGACCCGAA CAACCTCAAT    600

TCCGAAGACA TGGATATCCT GATGGAACGA AACCTTCGAA CTCCAAACCT GCTCGCATTC    660

GTAAGGGCTG TCAAGCACTT AGAAAATGCA TCAGGTATTG AGGCAATTCT TCGTAATCTC    720

CAACCATGTC TGCCCTCTGC CACGGCCGCA CCCTCTCGAC ATCCAATCAT CATCAAGGCA    780

GGTGACTGGC AAGAATTCCG GGAAAAACTG ACGTTCTATC TGGTTACCCT TGAGCAAGCG    840

CAGGAACAAC AG                                                        852
```

(2) INFORMATION FOR SEQ ID NO: 53:

(i) SEQUENCE CHARACTERISTICS:
        (A) LENGTH: 852 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 53:

```
TCCCCGGCCC CGCCTGCTTG TGACCTCCGA GTCCTCAGTA AACTGCTTCG TGACTCCCAT    60
GTCCTTCACA GCAGACTGAG CCAGTGCCCA GAGGTTCACC CTTTGCCTAC ACCTGTCCTG   120
CTGCCTGCTG TGGACTTTAG CTTGGGAGAA TGGAAAACCC AGATGGAGGA GACCAAGGCA   180
CAGGACATTC TGGGAGCAGT GACCCTTCTG CTGGAGGGAG TGATGGCAGC ACGGGGACAA   240
CTGGGACCCA CTTGCCTCTC ATCCCTCCTG GGGCAGCTTT CTGGACAGGT CCGTCTCCTC   300
CTTGGGGCCC TGCAGAGCCT CCTTGGAACC CAGGGCAGGA CCACAGCTCA CAAGGATCCC   360
AATGCCATCT TCCTGAGCTT CCAACACCTG CTCCGAGGAA AGGTGCGTTT CCTGATGCTT   420
GTAGGAGGGT CCACCCTCTG CGTCAGGAA TTCCATGCAT ACGTAGAGGG CGGTGGAGGC    480
TCCCCGGGTG GTGGTTCTGG CGGCGGCTCC AACATGGCTA ACTGCTCTAT AATGATCGAT   540
GAAATTATAC ATCACTTAAA GAGACCACCT AACCCTTTGC TGGACCCGAA CAACCTCAAT   600
TCCGAAGACA TGGATATCCT GATGGAACGA AACCTTGAA CTCCAAACCT GCTCGCATTC    660
GTAAGGGCTG TCAAGCACTT AGAAAATGCA TCAGGTATTG AGGCAATTCT TCGTAATCTC   720
CAACCATGTC TGCCCTCTGC CACGGCCGCA CCCTCTCGAC ATCAATCAT CATCAAGGCA    780
GGTGACTGGC AAGAATTCCG GGAAAAACTG ACGTTCTATC TGGTTACCCT TGAGCAAGCG   840
CAGGAACAAC AG                                                       852
```

(2) INFORMATION FOR SEQ ID NO: 54:

(i) SEQUENCE CHARACTERISTICS:
        (A) LENGTH: 840 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 54:

```
GCTAACTGCT CTATAATGAT CGATGAAATT ATACATCACT TAAAGAGACC ACCTAACCCT    60
TTGCTGGACC CGAACAACCT CAATTCCGAA GACATGGATA TCCTGATGGA ACGAAACCTT   120
CGAACTCCAA ACCTGCTCGC ATTCGTAAGG GCTGTCAAGC ACTTAGAAAA TGCATCAGGT   180
ATTGAGGCAA TTCTTCGTAA TCTCCAACCA TGTCTGCCCT CTGCCACGGC CGCACCCTCT   240
CGACATCCAA TCATCATCAA GGCAGGTGAC TGGCAAGAAT TCCGGGAAAA ACTGACGTTC   300
TATCTGGTTA CCCTTGAGCA AGCGCAGGAA CAACAGTACG TAGAGGGCGG TGGAGGCTCC   360
CCGGGTGGTG GTTCTGGCGG CGGCTCCAAC ATGTCCCCGG CCCCGCCTGC TTGTGACCTC   420
CGAGTCCTCA GTAAACTGCT TCGTGACTCC CATGTCCTTC ACAGCAGACT GAGCCAGTGC   480
CCAGAGGTTC ACCCTTTGCC TACACCTGTC CTGCTGCCTG CTGTGGACTT TAGCTTGGGA   540
GAATGGAAAA CCCAGATGGA GGAGACCAAG GCACAGGACA TTCTGGGAGC AGTGACCCTT   600
CTGCTGGAGG GAGTGATGGC AGCACGGGGA CAACTGGGAC CCACTTGCCT CTCATCCCTC   660
```

```
CTGGGGCAGC TTTCTGGACA GGTCCGTCTC CTCCTTGGGG CCCTGCAGAG CCTCCTTGGA      720

ACCCAGGGCA GGACCACAGC TCACAAGGAT CCCAATGCCA TCTTCCTGAG CTTCCAACAC      780

CTGCTCCGAG GAAAGGTGCG TTTCCTGATG CTTGTAGGAG GGTCCACCCT CTGCGTCAGG      840
```

(2) INFORMATION FOR SEQ ID NO: 55:

(i) SEQUENCE CHARACTERISTICS:
        (A) LENGTH: 471 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 55:

```
TCTCCGGCGC CGCCTGCTTG TGACCTCCGA GTCCTCAGTA AACTGCTTCG TGACTCCCAT       60

GTCCTTCACA GCAGACTGAG CCAGTGCCCA GAGGTTCACC CTTTGCCTAC ACCTGTCCTG      120

CTGCCTGCTG TGGACTTTAG CTTGGGAGAA TGGAAAACCC AGATGGAGGA GACCAAGGCA      180

CAGGACATTC TGGGAGCAGT GACCCTTCTG CTGGAGGGAG TGATGGCAGC ACGGGGACAA      240

CTGGGACCCA CTTGCCTCTC ATCCCTCCTG GGGCAGCTTT CTGGACAGGT CCGTCTCCTC      300

CTTGGGGCCC TGCAGAGCCT CCTTGGAACC CAGGGCAGGA CCACAGCTCA CAAGGATCCC      360

AATGCCATCT TCCTGAGCTT CCAACACCTG CTCCGAGGAA AGGTGCGTTT CCTGATGCTT      420

GTAGGAGGGT CCACCCTCTG CGTCAGGGAA TTCCATCACC ATCACCATCA C              471
```

(2) INFORMATION FOR SEQ ID NO: 56:

(i) SEQUENCE CHARACTERISTICS:
        (A) LENGTH: 474 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 56:

```
CATCACCATC ACCATCACGC CATGGCGTCT CCGGCGCCGC CTGCTTGTGA CCTCCGAGTC       60

CTCAGTAAAC TGCTTCGTGA CTCCCATGTC CTTCACAGCA GACTGAGCCA GTGCCCAGAG      120

GTTCACCCTT TGCCTACACC TGTCCTGCTG CCTGCTGTGG ACTTTAGCTT GGGAGAATGG      180

AAAACCCAGA TGGAGGAGAC CAAGGCACAG GACATTCTGG GAGCAGTGAC CCTTCTGCTG      240

GAGGGAGTGA TGGCAGCACG GGGACAACTG GGACCCACTT GCCTCTCATC CCTCCTGGGG      300

CAGCTTTCTG GACAGGTCCG TCTCCTCCTT GGGGCCCTGC AGAGCCTCCT TGGAACCCAG      360

GGCAGGACCA CAGCTCACAA GGATCCCAAT GCCATCTTCC TGAGCTTCCA ACACCTGCTC      420

CGAGGAAAGG TGCGTTTCCT GATGCTTGTA GGAGGGTCCA CCCTCTGCGT CAGG           474
```

(2) INFORMATION FOR SEQ ID NO: 57:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 57:

```
Glu Phe His His His His His His
1               5
```

(2) INFORMATION FOR SEQ ID NO: 58:

(i) SEQUENCE CHARACTERISTICS:
        (A) LENGTH: 459 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 58:

```
TCTCCGGCGC CGCCTGCTTG TGACCTCCGA GTCCTCAGTA AACTGCTTCG TGACTCCCAT    60

GTCCTTCACA GCAGACTGAG CCAGTGCCCA GAGGTTCACC CTTTGCCTAC ACCTGTCCTG   120

CTGCCTGCTG TGGACTTTAG CTTGGGAGAA TGGAAAACCC AGATGGAGGA GACCAAGGCA   180

CAGGACATTC TGGGAGCAGT GACCCTTCTG CTGGAGGGAG TGATGGCAGC ACGGGGACAA   240

CTGGGACCCA CTTGCCTCTC ATCCCTCCTG GGCAGCTTT CTGGACAGGT CCGTCTCCTC    300

CTTGGGGCCC TGCAGAGCCT CCTTGGAACC CAGCTTCCTC CACAGGGCAG GACCACAGCT   360

CACAAGGATC CCAATGCCAT CTTCCTGAGC TTCCAACACC TGCTCCGAGG AAAGGTGCGT   420

TTCCTGATGC TTGTAGGAGG GTCCACCCTC TGCGTCAGG                          459
```

(2) INFORMATION FOR SEQ ID NO: 59:

(i) SEQUENCE CHARACTERISTICS:
        (A) LENGTH: 996 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 59:

```
AGCCCGGCTC CTCCTGCTTG TGACCTCCGA GTCCTCAGTA AACTGCTTCG TGACTCCCAT    60

GTCCTTCACA GCAGACTGAG CCAGTGCCCA GAGGTTCACC CTTTGCCTAC ACCTGTCCTG   120

CTGCCTGCTG TGGACTTTAG CTTGGGAGAA TGGAAAACCC AGATGGAGGA GACCAAGGCA   180

CAGGACATTC TGGGAGCAGT GACCCTTCTG CTGGAGGGAG TGATGGCAGC ACGGGGACAA   240

CTGGGACCCA CTTGCCTCTC ATCCCTCCTG GGCAGCTTT CTGGACAGGT CCGTCTCCTC    300

CTTGGGGCCC TGCAGAGCCT CCTTGGAACC CAGCTTCCTC CACAGGGCAG GACCACAGCT   360

CACGAGGATC CCAATGCCAT CTTCCTGAGC TTCCAACACC TGCTCCGAGG AAAGGTGCGT   420

TTCCTGATGC TTGTAGGAGG GTCCACCCTC TGCGTCAGGC GGGCCCCACC CACCACAGCT   480

GTCCCCAGCA GAACCTCTCT AGTCCTCACA CTGAACGAGC TCCCAAACAG GACTTCTGGA   540

TTGTTGGAGA CAAACTTCAC TGCCTCAGCC AGAACAACTG GCTCTGGGCT TCTGAAGTGG   600

CAGCAGGGAT TCAGAGCCAA GATTCCTGGT CTGCTGAACC AAACCTCCAG GTCCCTGGAC   660

CAAATCCCCG GATACCTGAA CAGGATACAC GAACTCTTGA ATGGAACTCG TGGACTCTTT   720

CCTGGACCCT CACGCAGGAC CCTAGGAGCC CCGGACATTT CCTCAGGAAC ATCAGACACA   780

GGCTCCCTGC CACCCAACCT CCAGCCTGGA TATTCTCCTT CCCCAACCCA TCCTCCTACT   840

GGACAGTATA CGCTCTTCCC TCTTCCACCC ACCTTGCCCA CCCCTGTGGT CCAGCTCCAC   900

CCCCTGCTTC CTGACCCTTC TGCTCCAACG CCCACCCCTA CCAGCCCTCT TCTAAACACA   960

TCCTACACCC ACTCCCAGAA TCTGTCTCAG GAAGGG                             996
```

(2) INFORMATION FOR SEQ ID NO: 60:

(i) SEQUENCE CHARACTERISTICS:
        (A) LENGTH: 996 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 60:

| | | |
|---|---|---|
| AGCCCGGCTC CTCCTGCTTG TGACCTCCGA GTCCTCAGTA AACTGCTTCG TGACTCCCAT | 60 |
| GTCCTTCACA GCAGACTGAG CCAGTGCCCA GAGGTTCACC CTTTGCCTAC ACCTGTCCTG | 120 |
| CTGCCTGCTG TGGACCTTAG CTTGGGAGAA TGGAAAACCC AGATGGAGGA GACCAAGGCA | 180 |
| CAGGACATTC TGGGAGCAGT GACCCTTCTG CTGGAGGGAG TGATGGCAGC ACGGGGACAA | 240 |
| CTGGGACCCA CTTGCCTCTC ATCCCTCCTG GGGCAGCTTT CTGGACAGGT CCGTCTCCTC | 300 |
| CTTGGGGCCC TGCAGAGCCT CCTTGGAACC CAGCTTCCTC CACAGGGCAG GACCACAGCT | 360 |
| CACAAGGATC CCAATGCCAT CTTCCTGAGC TTCCAACACC TGCTCCGAGG AAAGGTGCGT | 420 |
| TTCCTGATGC TTGTAGGAGG GTCCACCCTC TGCGTCAGGC GGGCCCCACC CACCACAGCT | 480 |
| GTCCCCAGCA GAACCTCTCT AGTCCTCACA CTGAACGAGC TCCCAAACAG GACTTCTGGA | 540 |
| TTGTTGGAGA CAAACTTCAC TGCCTCAGCC AGAACAACTG GCTCTGGGCT TCTGAAGCGG | 600 |
| CAGCAGGGAT TCAGAGCCAA GATTCCTGGT CTGCTGAACC AAACCTCCAG GTCCCTGGAC | 660 |
| CAAATCCCCG GATACCTGAA CAGGATACAC GAACTCTTGA ATGGAACTCG TGGACTCTTT | 720 |
| CCTGGACCCT CACGCAGGAC CCTAGGAGCC CCGGACATTT CCTCAGGAAC ATCAGACACA | 780 |
| GGCTCCCTGC CACCCAACCT CCAGCCTGGA TATTCTCCTT CCCCAACCCA TCCTCCTACT | 840 |
| GGACAGTATA CGCTCTTCCC TCTTCCACCC ACCTTGCCCA CCCCTGTGGT CCAGCTCCAC | 900 |
| CCCCTGCTTC CTGACCCTTC TGCTCCAACG CCCACCCCTA CCAGCCCTCT TCTAAACACA | 960 |
| TCCTACACCC ACTCCCAGAA TCTGTCTCAG GAAGGG | 996 |

(2) INFORMATION FOR SEQ ID NO: 61:

(i) SEQUENCE CHARACTERISTICS:
        (A) LENGTH: 1188 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 61:

| | | |
|---|---|---|
| TCCCCAGCTC CACCTGCTTG TGACCTCCGA GTCCTCAGTA AACTGCTTCG TGACTCCCAT | 60 |
| GTCCTTCACA GCAGACTGAG CCAGTGCCCA GAGGTTCACC CTTTGCCTAC ACCTGTCCTG | 120 |
| CTGCCTGCTG TGGACTTTAG CTTGGGAGAA TGGAAAACCC AGATGGAGGA GACCAAGGCA | 180 |
| CAGGACATTC TGGGAGCAGT GACCCTTCTG CTGGAGGGAG TGATGGCAGC ACGGGGACAA | 240 |
| CTGGGACCCA CTTGCCTCTC ATCCCTCCTG GGGCAGCTTT CTGGACAGGT CCGTCTCCTC | 300 |
| CTTGGGGCCC TGCAGAGCCT CCTTGGAACC CAGCTTCCTC CACAGGGCAG GACCACAGCT | 360 |
| CACAAGGATC CCAATGCCAT CTTCCTGAGC TTCCAACACC TGCTCCGAGG AAAGGTGCGT | 420 |
| TTCCTGATGC TTGTAGGAGG GTCCACCCTC TGCGTCAGGG AATTCATTGA AGGCCGCCAA | 480 |
| TTCAAGCTTG AGCCCAGAGG GCCCACAATC AAGCCCTGTC CTCCATGCAA ATGCCCAGCA | 540 |
| CCTAACCTCT TGGGTGGACC ATCCGTCTTC ATCTTCCCTC CAAAGATCAA GGATGTACTC | 600 |
| ATGATCTCCC TGAGCCCCAT AGTCACATGT GTGGTGGTGG ATGTGAGCGA GGATGACCCA | 660 |

```
GATGTCCAGA TCAGCTGGTT TGTGAACAAC GTGGAAGTAC ACACAGCTCA GACACAAACC      720

CATAGAGAGG ATTACAACAG TACTCTCCGG GTGGTCAGTG CCCTCCCCAT CCAGCACCAG      780

GACTGGATGA GTGGCAAGGA GTTCAAATGC AAGGTCAACA ACAAAGACCT CCCAGCGCCC      840

ATCGAGAGAA CCATCTCAAA ACCCAAAGGG TCAGTAAGAG CTCCACAGGT ATATGTCTTG      900

CCTCCACCAG AAGAAGAGAT GACTAAGAAA CAGGTCACTC TGACCTGCAT GGTCACAGAC      960

TTCATGCCTG AAGACATTTA CGTGGAGTGG ACCAACAACG GGAAAACAGA GCTAAACTAC     1020

AAGAACACTG AACCAGTCCT GGACTCTGAT GGTTCTTACT TCATGTACAG CAAGCTGAGA     1080

GTGGAAAAGA AGAACTGGGT GGAAAGAAAT AGCTACTCCT GTTCAGTGGT CCACGAGGGT     1140

CTGCACAATC ACCACACGAC TAAGAGCTTC TCCCGGACTC CGGGTAAA               1188

(2) INFORMATION FOR SEQ ID NO: 62:

(i) SEQUENCE CHARACTERISTICS:
           (A) LENGTH: 855 base pairs
           (B) TYPE: nucleic acid
           (C) STRANDEDNESS: double
           (D) TOPOLOGY: linear (ii) MOLECULE TYPE: DNA (genomic)

(xi) SEQUENCE DESCRIPTION: SEQ ID NO: 62:

GCTAACTGCT CTATAATGAT CGATGAAATT ATACATCACT TAAAGAGACC ACCTAACCCT       60

TTGCTGGACC CGAACAACCT CAATTCCGAA GACATGGATA TCCTGATGGA ACGAAACCTT      120

CGAACTCCAA ACCTGCTCGC ATTCGTAAGG GCTGTCAAGC ACTTAGAAAA TGCATCAGGT      180

ATTGAGGCAA TTCTTCGTAA TCTCCAACCA TGTCTGCCCT CTGCCACGGC CGCACCCTCT      240

CGACATCCAA TCATCATCAA GGCAGGTGAC TGGCAAGAAT TCCGGGAAAA ACTGACGTTC      300

TATCTGGTTA CCCTTGAGCA AGCGCAGGAA CAACAGTACG TAATCGAGGG AAGGATTTCC      360

CCGGGTGGTG GTTCTGGCGG CGGCTCCAAC ATGGCGTCTC CGGCGCCGCC TGCTTGTGAC      420

CTCCGAGTCC TCAGTAAACT GCTTCGTGAC TCCCATGTCC TTCACAGCAG ACTGAGCCAG      480

TGCCCAGAGG TTCACCCTTT GCCTACACCT GTCCTGCTGC CTGCTGTGGA CTTTAGCTTG      540

GGAGAATGGA AAACCCAGAT GGAGGAGACC AAGGCACAGG ACATTCTGGG AGCAGTGACC      600

CTTCTGCTGG AGGGAGTGAT GGCAGCACGG GGACAACTGG GACCCACTTG CCTCTCATCC      660

CTCCTGGGGC AGCTTTCTGG ACAGGTCCGT CTCCTCCTTG GGCCCTGCA GAGCCTCCTT       720

GGAACCCAGC TTCCTCCACA GGGCAGGACC ACAGCTCACA AGGATCCCAA TGCCATCTTC      780

CTGAGCTTCC AACACCTGCT CCGAGGAAAG GTGCGTTTCC TGATGCTTGT AGGAGGGTCC      840

ACCCTCTGCG TCAGG                                                       855

(2) INFORMATION FOR SEQ ID NO: 63:

(i) SEQUENCE CHARACTERISTICS:
           (A) LENGTH: 855 base pairs
           (B) TYPE: nucleic acid
           (C) STRANDEDNESS: double
           (D) TOPOLOGY: linear (ii) MOLECULE TYPE: DNA (genomic)

(xi) SEQUENCE DESCRIPTION: SEQ ID NO: 63:

GCTAACTGCT CTATAATGAT CGATGAAATT ATACATCACT TAAAGAGACC ACCTAACCCT       60

TTGCTGGACC CGAACAACCT CAATTCCGAA GACATGGATA TCCTGATGGA ACGAAACCTT      120
```

```
CGAACTCCAA ACCTGCTCGC ATTCGTAAGG GCTGTCAAGC ACTTAGAAAA TGCATCAGGT      180

ATTGAGGCAA TTCTTCGTAA TCTCCAACCA TGTCTGCCCT CTGCCACGGC CGCACCCTCT      240

CGACATCCAA TCATCATCAA GGCAGGTGAC TGGCAAGAAT TCCGGGAAAA ACTGACGTTC      300

TATCTGGTTA CCCTTGAGCA AGCGCAGGAA CAACAGTACG TAGAGGGCGG TGGAGGCTCC      360

CCGGGTGGTG GTTCTGGCGG CGGCTCCAAC ATGGCGTCTC CGGCGCCGCC TGCTTGTGAC      420

CTCCGAGTCC TCAGTAAACT GCTTCGTGAC TCCCATGTCC TTCACAGCAG ACTGAGCCAG      480

TGCCCAGAGG TTCACCCTTT GCCTACACCT GTCCTGCTGC CTGCTGTGGA CTTTAGCTTG      540

GGAGAATGGA AAACCCAGAT GGAGGAGACC AAGGCACAGG ACATTCTGGG AGCAGTGACC      600

CTTCTGCTGG AGGGAGTGAT GGCAGCACGG GGACAACTGG GACCCACTTG CCTCTCATCC      660

CTCCTGGGGC AGCTTTCTGG ACAGGTCCGT CTCCTCCTTG GGGCCCTGCA GAGCCTCCTT      720

GGAACCCAGC TTCCTCCACA GGGCAGGACC ACAGCTCACA AGGATCCCAA TGCCATCTTC      780

CTGAGCTTCC AACACCTGCT CCGAGGAAAG GTGCGTTTCC TGATGCTTGT AGGAGGGTCC      840

ACCCTCTGCG TCAGG                                                       855

(2) INFORMATION FOR SEQ ID NO: 64:

(i) SEQUENCE CHARACTERISTICS:
        (A) LENGTH: 864 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 64:

TCCCCAGCTC CACCTGCTTG TGACCTCCGA GTCCTCAGTA AACTGCTTCG TGACTCCCAT       60

GTCCTTCACA GCAGACTGAG CCAGTGCCCA GAGGTTCACC CTTTGCCTAC ACCTGTCCTG      120

CTGCCTGCTG TGGACTTTAG CTTGGGAGAA TGGAAAACCC AGATGGAGGA GACCAAGGCA      180

CAGGACATTC TGGGAGCAGT GACCCTTCTG CTGGAGGGAG TGATGGCAGC ACGGGGACAA      240

CTGGGACCCA CTTGCCTCTC ATCCCTCCTG GGGCAGCTTT CTGGACAGGT CCGTCTCCTC      300

CTTGGGGCCC TGCAGAGCCT CCTTGGAACC CAGCTTCCTC CACAGGGCAG GACCACAGCT      360

CACAAGGATC CCAATGCCAT CTTCCTGAGC TTCCAACACC TGCTCCGAGG AAAGGTGCGT      420

TTCCTGATGC TTGTAGGAGG GTCCACCCTC TGCGTCAGGG AATTCCATGC ATACGTAATC      480

GAGGGAAGGA TTTCCCCGGG TGGTGGTTCT GGCGGCGGCT CCAACATGGC TAACTGCTCT      540

ATAATGATCG ATGAAATTAT ACATCACTTA AAGAGACCAC CTAACCCTTT GCTGGACCCG      600

AACAACCTCA ATTCCGAAGA CATGGATATC CTGATGGAAC GAAACCTTCG AACTCCAAAC      660

CTGCTCGCAT TCGTAAGGGC TGTCAAGCAC TTAGAAAATG CATCAGGTAT TGAGGCAATT      720

CTTCGTAATC TCCAACCATG TCTGCCCTCT GCCACGGCCG CACCCTCTCG ACATCCAATC      780

ATCATCAAGG CAGGTGACTG GCAAGAATTC CGGGAAAAAC TGACGTTCTA TCTGGTTACC      840

CTTGAGCAAG CGCAGGAACA ACAG                                             864

(2) INFORMATION FOR SEQ ID NO: 65:

(i) SEQUENCE CHARACTERISTICS:
        (A) LENGTH: 153 amino acids
        (B) TYPE: amino acid
        (C) STRANDEDNESS:
        (D) TOPOLOGY: linear (ii) MOLECULE TYPE: protein
```

(xi) SEQUENCE DESCRIPTION: SEQ ID NO: 65:

Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
                20                  25                  30

His Pro Leu Pro Thr Pro Val Leu Leu Pro Ala Val Asp Phe Ser Leu
            35                  40                  45

Gly Glu Trp Lys Thr Gln Met Glu Glu Thr Lys Ala Gln Asp Ile Leu
50                      55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
130                 135                 140

Val Gly Gly Ser Thr Leu Cys Val Arg
145                 150

(2) INFORMATION FOR SEQ ID NO: 66:

(i) SEQUENCE CHARACTERISTICS:
        (A) LENGTH: 332 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 66:

Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
                20                  25                  30

His Pro Leu Pro Thr Pro Val Leu Leu Pro Ala Val Asp Phe Ser Leu
            35                  40                  45

Gly Glu Trp Lys Thr Gln Met Glu Glu Thr Lys Ala Gln Asp Ile Leu
50                      55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Glu Asp Pro Asn Ala Ile Phe
            115                 120                 125

Leu Ser Phe Gln His Leu Leu Arg Gly Lys Val Arg Phe Leu Met Leu
130                 135                 140

Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu Pro Asn
                165                 170                 175

```
Arg Thr Ser Gly Leu Leu Glu Thr Asn Phe Thr Ala Ser Ala Arg Thr
            180                 185                 190

Thr Gly Ser Gly Leu Leu Lys Trp Gln Gln Gly Phe Arg Ala Lys Ile
        195                 200                 205

Pro Gly Leu Leu Asn Gln Thr Ser Arg Ser Leu Asp Gln Ile Pro Gly
    210                 215                 220

Tyr Leu Asn Arg Ile His Glu Leu Leu Asn Gly Thr Arg Gly Leu Phe
225                 230                 235                 240

Pro Gly Pro Ser Arg Arg Thr Leu Gly Ala Pro Asp Ile Ser Ser Gly
                245                 250                 255

Thr Ser Asp Thr Gly Ser Leu Pro Pro Asn Leu Gln Pro Gly Tyr Ser
            260                 265                 270

Pro Ser Pro Thr His Pro Pro Thr Gly Gln Tyr Thr Leu Phe Pro Leu
        275                 280                 285

Pro Pro Thr Leu Pro Thr Pro Val Val Gln Leu His Pro Leu Leu Pro
    290                 295                 300

Asp Pro Ser Ala Pro Thr Pro Thr Pro Thr Ser Pro Leu Leu Asn Thr
305                 310                 315                 320

Ser Tyr Thr His Ser Gln Asn Leu Ser Gln Glu Gly
                325                 330

(2) INFORMATION FOR SEQ ID NO: 67:

(i) SEQUENCE CHARACTERISTICS:
        (A) LENGTH: 312 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 67:

Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Leu Ser Leu
        35                  40                  45

Gly Glu Trp Lys Thr Gln Met Glu Glu Thr Lys Ala Gln Asp Ile Leu
    50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
            100                 105                 110

Pro Pro Gln Gly Arg Thr Thr Ala His Lys Asp Pro Asn Ala Ile Phe
        115                 120                 125

Leu Ser Phe Gln His Leu Leu Arg Gly Lys Val Arg Phe Leu Met Leu
    130                 135                 140

Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu Pro Asn
                165                 170                 175

Arg Thr Ser Gly Leu Leu Glu Thr Asn Phe Thr Ala Ser Ala Arg Thr
            180                 185                 190
```

```
Thr Gly Ser Gly Leu Leu Lys Arg Gln Gln Gly Phe Arg Ala Lys Ile
        195                 200                 205

Pro Gly Leu Leu Asn Gln Thr Ser Arg Ser Leu Asp Gln Ile Pro Gly
    210                 215                 220

Tyr Leu Asn Arg Ile His Glu Leu Leu Asn Gly Thr Arg Gly Leu Phe
225                 230                 235                 240

Pro Gly Pro Ser Arg Arg Thr Leu Gly Ala Pro Asp Ile Ser Ser Gly
            245                 250                 255

Thr Ser Asp Thr Gly Ser Leu Pro Pro Asn Leu Gln Pro Gly Tyr Ser
            260                 265                 270

Pro Ser Pro Thr His Pro Pro Thr Pro Leu Leu Pro Asp Pro Ser Ala
        275                 280                 285

Pro Thr Pro Thr Pro Thr Ser Pro Leu Leu Asn Thr Ser Tyr Thr His
    290                 295                 300

Ser Gln Asn Leu Ser Gln Glu Gly
305                 310
```

(2) INFORMATION FOR SEQ ID NO: 68:

(i) SEQUENCE CHARACTERISTICS:
        (A) LENGTH: 396 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 68:

```
Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
                20                  25                  30

His Pro Leu Pro Thr Pro Val Leu Leu Pro Ala Val Asp Phe Ser Leu
            35                  40                  45

Gly Glu Trp Lys Thr Gln Met Glu Glu Thr Lys Ala Gln Asp Ile Leu
        50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
130                 135                 140

Val Gly Gly Ser Thr Leu Cys Val Arg Glu Phe Ile Glu Gly Arg Gln
145                 150                 155                 160

Phe Lys Leu Glu Pro Arg Gly Pro Thr Ile Lys Pro Cys Pro Pro Cys
                165                 170                 175

Lys Cys Pro Ala Pro Asn Leu Leu Gly Gly Pro Ser Val Phe Ile Phe
            180                 185                 190

Pro Pro Lys Ile Lys Asp Val Leu Met Ile Ser Leu Ser Pro Ile Val
            195                 200                 205

Thr Cys Val Val Val Asp Val Ser Glu Asp Asp Pro Asp Val Gln Ile
        210                 215                 220
```

-continued

```
Ser Trp Phe Val Asn Asn Val Glu Val His Thr Ala Gln Thr Gln Thr
225                 230                 235                 240

His Arg Glu Asp Tyr Asn Ser Thr Leu Arg Val Val Ser Ala Leu Pro
                245                 250                 255

Ile Gln His Gln Asp Trp Met Ser Gly Lys Glu Phe Lys Cys Lys Val
                260                 265                 270

Asn Asn Lys Asp Leu Pro Ala Pro Ile Glu Arg Thr Ile Ser Lys Pro
            275                 280                 285

Lys Gly Ser Val Arg Ala Pro Gln Val Tyr Val Leu Pro Pro Pro Glu
        290                 295                 300

Glu Glu Met Thr Lys Lys Gln Val Thr Leu Thr Cys Met Val Thr Asp
305                 310                 315                 320

Phe Met Pro Glu Asp Ile Tyr Val Glu Trp Thr Asn Asn Gly Lys Thr
                325                 330                 335

Glu Leu Asn Tyr Lys Asn Thr Glu Pro Val Leu Asp Ser Asp Gly Ser
            340                 345                 350

Tyr Phe Met Tyr Ser Lys Leu Arg Val Glu Lys Lys Asn Trp Val Glu
        355                 360                 365

Arg Asn Ser Tyr Ser Cys Ser Val Val His Glu Gly Leu His Asn His
    370                 375                 380

His Thr Thr Lys Ser Phe Ser Arg Thr Pro Gly Lys
385                 390                 395
```

(2) INFORMATION FOR SEQ ID NO: 69:

(i) SEQUENCE CHARACTERISTICS:
        (A) LENGTH: 285 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 69:

```
Ala Asn Cys Ser Ile Met Ile Asp Glu Ile Ile His His Leu Lys Arg
1               5                   10                  15

Pro Pro Asn Pro Leu Leu Asp Pro Asn Asn Leu Asn Ser Glu Asp Met
            20                  25                  30

Asp Ile Leu Met Glu Arg Asn Leu Arg Thr Pro Asn Leu Leu Ala Phe
        35                  40                  45

Val Arg Ala Val Lys His Leu Glu Asn Ala Ser Gly Ile Glu Ala Ile
    50                  55                  60

Leu Arg Asn Leu Gln Pro Cys Leu Pro Ser Ala Thr Ala Ala Pro Ser
65                  70                  75                  80

Arg His Pro Ile Ile Lys Ala Gly Asp Trp Gln Glu Phe Arg Glu
                85                  90                  95

Lys Leu Thr Phe Tyr Leu Val Thr Leu Glu Gln Ala Gln Glu Gln Gln
                100                 105                 110

Tyr Val Ile Glu Arg Ile Ser Pro Gly Gly Gly Ser Gly Gly Gly
            115                 120                 125

Ser Asn Met Ala Ser Pro Ala Pro Ala Cys Asp Leu Arg Val Leu
            130                 135                 140

Ser Lys Leu Leu Arg Asp Ser His Val Leu His Ser Arg Leu Ser Gln
145                 150                 155                 160

Cys Pro Glu Val His Pro Leu Pro Thr Pro Val Leu Leu Pro Ala Val
                165                 170                 175
```

```
Asp Phe Ser Leu Gly Glu Trp Lys Thr Gln Met Glu Glu Thr Lys Ala
            180                 185                 190

Gln Asp Ile Leu Gly Ala Val Thr Leu Leu Glu Gly Val Met Ala
        195                 200                 205

Ala Arg Gly Gln Leu Gly Pro Thr Cys Leu Ser Ser Leu Leu Gly Gln
        210                 215                 220

Leu Ser Gly Gln Val Arg Leu Leu Leu Gly Ala Leu Gln Ser Leu Leu
225                 230                 235                 240

Gly Thr Gln Leu Pro Pro Gln Gly Arg Thr Thr Ala His Lys Asp Pro
                245                 250                 255

Asn Ala Ile Phe Leu Ser Phe Gln His Leu Leu Arg Gly Lys Val Arg
                260                 265                 270

Phe Leu Met Leu Val Gly Gly Ser Thr Leu Cys Val Arg
                275                 280                 285

(2) INFORMATION FOR SEQ ID NO: 70:

(i) SEQUENCE CHARACTERISTICS:
        (A) LENGTH: 285 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 70:

Ala Asn Cys Ser Ile Met Ile Asp Glu Ile His His Leu Lys Arg
1               5                   10                  15

Pro Pro Asn Pro Leu Leu Asp Pro Asn Asn Leu Asn Ser Glu Asp Met
                20                  25                  30

Asp Ile Leu Met Glu Arg Asn Leu Arg Thr Pro Asn Leu Leu Ala Phe
            35                  40                  45

Val Arg Ala Val Lys His Leu Glu Asn Ala Ser Gly Ile Glu Ala Ile
        50                  55                  60

Leu Arg Asn Leu Gln Pro Cys Leu Pro Ser Ala Thr Ala Ala Pro Ser
65                  70                  75                  80

Arg His Pro Ile Ile Ile Lys Ala Gly Asp Trp Gln Glu Phe Arg Glu
                85                  90                  95

Lys Leu Thr Phe Tyr Leu Val Thr Leu Glu Gln Ala Gln Glu Gln Gln
            100                 105                 110

Tyr Val Glu Gly Gly Gly Ser Pro Gly Gly Ser Gly Gly Gly
        115                 120                 125

Ser Asn Met Ala Ser Pro Ala Pro Ala Cys Asp Leu Arg Val Leu
130                 135                 140

Ser Lys Leu Leu Arg Asp Ser His Val Leu His Ser Arg Leu Ser Gln
145                 150                 155                 160

Cys Pro Glu Val His Pro Leu Pro Thr Pro Val Leu Leu Pro Ala Val
                165                 170                 175

Asp Phe Ser Leu Gly Glu Trp Lys Thr Gln Met Glu Glu Thr Lys Ala
            180                 185                 190

Gln Asp Ile Leu Gly Ala Val Thr Leu Leu Glu Gly Val Met Ala
        195                 200                 205

Ala Arg Gly Gln Leu Gly Pro Thr Cys Leu Ser Ser Leu Leu Gly Gln
        210                 215                 220

Leu Ser Gly Gln Val Arg Leu Leu Leu Gly Ala Leu Gln Ser Leu Leu
225                 230                 235                 240
```

```
Gly Thr Gln Leu Pro Pro Gln Gly Arg Thr Thr Ala His Lys Asp Pro
                245                 250                 255

Asn Ala Ile Phe Leu Ser Phe Gln His Leu Leu Arg Gly Lys Val Arg
            260                 265                 270

Phe Leu Met Leu Val Gly Gly Ser Thr Leu Cys Val Arg
        275                 280                 285
```

(2) INFORMATION FOR SEQ ID NO: 71:

(i) SEQUENCE CHARACTERISTICS:
        (A) LENGTH: 288 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 71:

```
Ser Pro Ala Pro Ala Cys Asp Leu Arg Val Leu Ser Lys Leu Leu
1               5                   10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
            35                  40                  45

Gly Glu Trp Lys Thr Gln Met Glu Glu Thr Lys Ala Gln Asp Ile Leu
50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
            130                 135                 140

Val Gly Gly Ser Thr Leu Cys Val Arg Glu Phe His Ala Tyr Val Ile
145                 150                 155                 160

Glu Gly Arg Ile Ser Pro Gly Gly Ser Gly Gly Ser Asn Met
                165                 170                 175

Ala Asn Cys Ser Ile Met Ile Asp Glu Ile Ile His His Leu Lys Arg
            180                 185                 190

Pro Pro Asn Pro Leu Leu Asp Pro Asn Asn Leu Asn Ser Glu Asp Met
            195                 200                 205

Asp Ile Leu Met Glu Arg Asn Leu Arg Thr Pro Asn Leu Leu Ala Phe
210                 215                 220

Val Arg Ala Val Lys His Leu Glu Asn Ala Ser Gly Ile Glu Ala Ile
225                 230                 235                 240

Leu Arg Asn Leu Gln Pro Cys Leu Pro Ser Ala Thr Ala Ala Pro Ser
                245                 250                 255

Arg His Pro Ile Ile Ile Lys Ala Gly Asp Trp Gln Glu Phe Arg Glu
            260                 265                 270

Lys Leu Thr Phe Tyr Leu Val Thr Leu Glu Gln Ala Gln Glu Gln Gln
            275                 280                 285
```

(2) INFORMATION FOR SEQ ID NO: 72:

(i) SEQUENCE CHARACTERISTICS:
    (A) LENGTH: 864 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO: 72:

```
TCCCCAGCTC CACCTGCTTG TGACCTCCGA GTCCTCAGTA AACTGCTTCG TGACTCCCAT    60

GTCCTTCACA GCAGACTGAG CCAGTGCCCA GAGGTTCACC CTTTGCCTAC ACCTGTCCTG   120

CTGCCTGCTG TGGACTTTAG CTTGGGAGAA TGGAAAACCC AGATGGAGGA GACCAAGGCA   180

CAGGACATTC TGGGAGCAGT GACCCTTCTG CTGGAGGGAG TGATGGCAGC ACGGGGACAA   240

CTGGGACCCA CTTGCCTCTC ATCCCTCCTG GGGCAGCTTT CTGGACAGGT CCGTCTCCTC   300

CTTGGGGCCC TGCAGAGCCT CCTTGGAACC CAGCTTCCTC CACAGGGCAG GACCACAGCT   360

CACAAGGATC CCAATGCCAT CTTCCTGAGC TTCCAACACC TGCTCCGAGG AAAGGTGCGT   420

TTCCTGATGC TTGTAGGAGG GTCCACCCTC TGCGTCAGGG AATTCCATGC ATACGTAGAG   480

GGCGGTGGAG GCTCCCCGGG TGGTGGTTCT GGCGGCGGCT CCAACATGGC TAACTGCTCT   540

ATAATGATCG ATGAAATTAT ACATCACTTA AAGAGACCAC CTAACCCTTT GCTGGACCCG   600

AACAACCTCA ATTCCGAAGA CATGGATATC CTGATGGAAC GAAACCTTCG AACTCCAAAC   660

CTGCTCGCAT TCGTAAGGGC TGTCAAGCAC TTAGAAAATG CATCAGGTAT TGAGGCAATT   720

CTTCGTAATC TCCAACCATG TCTGCCCTCT GCCACGGCCG CACCCTCTCG ACATCCAATC   780

ATCATCAAGG CAGGTGACTG GCAAGAATTC CGGGAAAAAC TGACGTTCTA TCTGGTTACC   840

CTTGAGCAAG CGCAGGAACA ACAG                                         864
```

(2) INFORMATION FOR SEQ ID NO: 73:

(i) SEQUENCE CHARACTERISTICS:
    (A) LENGTH: 288 amino acids
    (B) TYPE: amino acid
    (C) STRANDEDNESS:
    (D) TOPOLOGY: linear (ii) MOLECULE TYPE: protein (xi) SEQUENCE DESCRIPTION: SEQ ID NO: 73:

```
Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
                20                  25                  30

His Pro Leu Pro Thr Pro Val Leu Leu Pro Ala Val Asp Phe Ser Leu
            35                  40                  45

Gly Glu Trp Lys Thr Gln Met Glu Glu Thr Lys Ala Gln Asp Ile Leu
50                  55                  60

Gly Ala Val Thr Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
130                 135                 140
```

-continued

```
Val Gly Gly Ser Thr Leu Cys Val Arg Glu Phe His Ala Tyr Val Glu
145                 150                 155                 160

Gly Gly Gly Gly Ser Pro Gly Gly Ser Gly Gly Ser Asn Met
                165                 170                 175

Ala Asn Cys Ser Ile Met Ile Asp Glu Ile Ile His His Leu Lys Arg
            180                 185                 190

Pro Pro Asn Pro Leu Leu Asp Pro Asn Asn Leu Asn Ser Glu Asp Met
        195                 200                 205

Asp Ile Leu Met Glu Arg Asn Leu Arg Thr Pro Asn Leu Leu Ala Phe
    210                 215                 220

Val Arg Ala Val Lys His Leu Glu Asn Ala Ser Gly Ile Glu Ala Ile
225                 230                 235                 240

Leu Arg Asn Leu Gln Pro Cys Leu Pro Ser Ala Thr Ala Ala Pro Ser
                245                 250                 255

Arg His Pro Ile Ile Ile Lys Ala Gly Asp Trp Gln Glu Phe Arg Glu
            260                 265                 270

Lys Leu Thr Phe Tyr Leu Val Thr Leu Glu Gln Ala Gln Glu Gln Gln
        275                 280                 285
```

THROMBOPOIETIN: IL-3 FUSION PROTEIN

This is a continuation-in-part of U.S. application Ser. No. 08/383,035 filed Feb. 3, 1995, now abandoned, which is incorporated herein by reference.

FIELD OF THE INVENTION

The present invention relates to human c-mpl ligands (thrombopoietin) with activity on hematopoietic differentiation and expansion.

BACKGROUND OF THE INVENTION

Megakaryocyte (MK) maturation and platelet production has been long thought to be regulated by lineage specific humoral growth factors in a manner similar to cytokines that induce erythrocyte (erythropoietin) and granulocyte (G-CSF) expansion and maturation. Platelets are responsible for the prevention of bleeding in response to vascular injury. Therefore, platelet production is a vital component of hematopoietic regulation. Patients undergoing chemotherapy or bone marrow transplantation usually experience severely depressed platelet levels (thrombocytopenia) which may result in life threatening bleeding episodes. Several known growth factors and cytokines have been found to stimulate megakaryocytes and platelet production but most are pleiotropic both in vitro and in vivo (IL-3, IL-6, IL-11, SCF). Plasma, serum and urine from thrombocytopenic dogs and humans have been found to contain growth factors that have specific megakaryopoietic and thrombopoietic activities distinct from all known cytokines. These factors have been termed Meg-CSF, MK-CSF, megakaryocyte growth and development factor (MGDF), megakaryopoietin, and thrombopoietin but the molecular structure has not been identified until recently.

The identification of the thrombopoietic cytokine, c-mpl ligand, originated with the identification of a myeloproliferative leukemia virus (MPLV, Wending et al., *Virology* 149:242–246 [1986]). Mice infected with this virus gave rise to multi-lineage myeloproliferation. Subsequent studies (Souyri et al., *Cell* 63:1137–1147, [1990]) demonstrated that the retrovirus encoded an oncogene (v-mpl) that when fused with viral envelope gene gave rise to a membrane anchored protein that resembles the cytoplasmic domain of the hematopoietic growth factor receptor family. V-mpl was used to probe both human and murine RNA libraries for homologous genes. Clones were identified in both species and termed c-mpl (Vigon et al., PNAS 89:5640–5644 [1992], Vigon et al., *Oncogene* 8:2607–2615 [1993]). C-mpl is a member of the cytokine receptor super-family with regions of homology to mIL-5rc, IL3rc, IL4rc, mEPOrc and mGCSFrc. A chimera of the intracellular domain of c-mpl and the extracellular domain of hIL-4rc was transfected into a growth factor dependent cell line (BaF3). Once transfected, the cells proliferated in response to hIL4 indicating that the c-mpl cytoplasmic domain was fully sufficient to transduce a proliferative signal (Skoda et al., *EMBO J.* 12(7):2645–2653 [1993]).

Message for c-mpl was found in a number of hematopoietic cell lines using reverse transcriptase polymerase chain reaction (RT-PCR) including the pluripotential cell lines TF-1, Mo-7E, UT-7 and KU812; and erythro/megakaryocytic cell lines HEL, DAMI and K153. Transcripts were also identified in bone marrow, fetal liver, megakaryocytes, platelets and CD34+enriched cells (Methia et al., *Blood* 82(5):1395–1401 [1993]).

The identification of a putative receptor triggered several investigative teams to search for a naturally occurring ligand for c-mpl. In June of 1994 several simultaneous publications reported on a ligand that bound to c-mpl and had megakaryocytopoietic properties (de Sauvage et al., *Nature* 369:533–539 [1994]; Lok et al., *Nature* 369:565–568 [1994]; Wendling et al., *Nature* 369:571–574 [1994] and Bartley et al., *Cell* 77:1117–1124 [1994]). The ligand referred to as c-mpl ligand, Megakaryocyte Growth and Development Factor (MGDF) or thrombopoietin (TPO) is a peptide with a predicted molecular mass of 35,000 kDa. The protein has a two domain structure with an amino-terminal domain (153 amino acids) with homology to erythropoietin and a carboxy-terminus rich in serine, threonine and proline residues which also contains several glycosylation sites. There are two potential arginine cleavage sites resulting in two shorter peptides of 25 kDa and 31 kDA forms both of which are biologically active. There is high inter-species homology between human, murine, porcine, canine, rat and rabbit c-mpl ligand and most forms are active on all species tested.

C-mpl ligand has been shown to stimulate the differentiation of CD34+ cells into cells with megakaryocyte characteristics. CD34+ cells, in the presence of c-mpl ligand, underwent endomitosis (Kaushansky et al., *Nature* 369:568–571 [1994]), expressed the megakaryocyte lineage specific cell surface antigen CD41a and had morphology characteristic of megakaryocytes. In vivo administration of c-mpl ligand gave rise to increased circulating platelets in normal mice (Lok et al., *Nature* 369:565–568 [1994]). C-mpl deficient mice generated by gene targeting demonstrated a 85% decrease in circulating platelets and megakaryocytes but had normal amounts of other hematopoietic lineages (Gurney et al., *Science* 265:1445–1447 [1994]). Absolute thrombocytopenia was not observed in these animals indicating that other cytokines may have some activity in expansion of the MK lineage.

Studies to date show that c-mpl ligand is a cytokine with specific activity on the maturation of megakaryocytes and in platelet production. Other cytokines have been shown to have activity on megakaryocyte expansion and differentiation, including IL-3, IL-6, IL-11 and c-kit ligand. Recent studies have demonstrated that these cytokines (with the exception of IL-3) act by stimulating the production of c-mpl ligand and do not have megakaryocyte stimulating activity by themselves (Kaushansky et al., PNAS 92:3234–3236 [1995]).

GB 2,285,446 relates to the c-mpl ligand (thrombopoietin) and various forms of thrombopoietin which are shown to influence the replication, differentiation and maturation of megakaryocytes and megakaryocytes progenitors which may be used for the treatment of thrombocytopenia.

The ability of c-mpl ligand to stimulate the proliferation and maturation of megakaryocytes and production of platelets indicates that c-mpl ligand may have therapeutic use in restoring circulating platelets to normal amounts in those cases where the number of platelets have been reduced due to diseases or therapeutic treatments such as radiation and/or chemotherapy.

EP 675,201 A1 relates to the c-mpl ligand (Megakaryocyte growth and development factor [MGDF]), allelic variations of c-mpl ligand and c-mpl ligand attached to water soluble polymers such as polyethylene glycol.

WO 95/21920 provides the murine and human c-mpl ligand and polypeptide fragments thereof. The proteins are useful for in vivo and ex vivo therapy for stimulating platelet production.

A previously published abstract (Eaton et al., *Blood* 84(10) Suppl. abstract 948, [1994]) reported c-DNA for an alternative splice form of c-mpl ligand identified in man, dog and mouse. The encoded protein has 4 amino deletion at position aa112–115. Although this molecule showed no activity in their bioassays, mRNA for this variant was found to be abundant in all three species indicating that it may be a naturally occurring alternative form of c-mpl ligand. Contrary to the previously published report, we found that the 1–153 Δ112–115 c-mpl ligand and the 1–332 Δ112–115 c-mpl ligand were biological active.

SUMMARY OF THE INVENTION

The present invention relates to novel c-mpl ligands of the following formula:

```
SerProAlaProProAlaCysAspLeuArgValLeuSerLysLeuLeu
1           5              10             15

ArgAspSerHisValLeuHisSerArgLeuSerGlnCysProGluVal
     1 20              25              30

HisProLeuProXaaProValLeuLeuProAlaValAspXaaXaaLeu
           35              40              45

GlyGluTrpLysThrGlnMetGluGluThrLysAlaGlnAspIleLeu
      50              55              60

GlyAlaValThrLeuLeuLeuGluGlyValMetAlaAlaArgGlyGln
65            70              75             80

LeuGlyProThrCysLeuSerSerLeuLeuGlyGlnLeuSerGlyGln
           85              90              95

ValArgLeuLeuLeuGlyAlaLeuGlnSerLeuLeuGlyThrGlnXaa
           100             105             110

XaaXaaXaaGlyArgThrThrAlaHisXaaAspProAsnAlaIlePhe
     115             120    122             125

LeuSerPheGlnHisLeuLeuArgGlyLysValArgPheLeuMetLeu
     130             135             140

ValGlyGlySerThrLeuCysValArgArgAlaProProThrThrAla
145           150             155             160

ValProSerArgThrSerLeuValLeuThrLeuAsnGluLeuProAsn
           165             170             175

ArgThrSerGlyLeuLeuGluThrAsnPheThrAlaSerAlaArgThr
          180             185             190

ThrGlySerGlyLeuLeuLysXaaGlnGlnGlyPheArgAlaLysIle
          195             200             205

ProGlyLeuLeuAsnGlnThrSerArgSerLeuAspGlnIleProGly
       210             215             220

TyrLeuAsnArgIleHisGluLeuLeuAsnGlyThrArgGlyLeuPhe
225           230             235             240

ProGlyProSerArgArgThrLeuGlyAlaProAspIleSerSerGly
           245             250             255

ThrSerAspThrGlySerLeuProProAsnLeuGlnProGlyTyrSer
          260             265             270

ProSerProThrHisProProThrGlyGlnTyrThrLeuPheProLeu
       275             280             285

ProProThrLeuProThrProValValGlnLeuHisProLeuLeuPro
   290             295             300

AspProSerAlaProThrProThrProThrSerProLeuLeuAsnThr
305           310             315             320

SerTyrThrHisSerGlnAsnLeuSerGlnGluGly
           325             330    332
``` wherein;

Xaa at position 37 is Thr, Asp or Glu;

Xaa at position 46 is Phe, Ala, Val, Leu, Ile, Pro, Trp, or Met;

Xaa at position 47 is Ser, Asp or Glu;

Xaa at position 112 is deleted or Leu, Ala, Val, Ile, Pro, Phe, Trp, or Met;

Xaa at position 113 is deleted or Pro, Phe, Ala, Val, Leu, Ile, Trp, or Met;

Xaa at position 114 is deleted or Pro, Phe, Ala, Val, Leu, Ile, Trp, or Met;

Xaa at position 115 is deleted or Gln, Gly, Ser, Thr, Tyr, or Asn;

Xaa at position 122 is Lys, Arg, His, Glu, or Asp;

Xaa at position 200 is Trp, Ala, Val, Leu, Ile, Pro, Phe, Met, Arg and Lys, or His and wherein from 1 to 179 amino acids can be deleted from the C-terminus and with the proviso that at least one of the amino acids designated by Xaa are different from the corresponding amino acids of native c-mpl ligand (1–332).

The present invention is also directed to a fragment of c-mpl with the following formula;

```
SerProAlaProProAlaCysAspLeuArgValLeuSerLysLeuLeu
1           5              10             15

ArgAspSerHisValLeuHisSerArgLeuSerGlnCysProGluVal
          20              25              30

HisProLeuProXaaProValLeuLeuProAlaValAspXaaXaaLeu
           35              40              45

GlyGluTrpLysThrGlnMetGluGluThrLysAlaGlnAspIleLeu
      50              55              60

GlyAlaValThrLeuLeuLeuGluGlyValMetAlaAlaArgGlyGln
65            70              75             80

LeuGlyProThrCysLeuSerSerLeuLeuGlyGlnLeuSerGlyGln
           85              90              95

ValArgLeuLeuLeuGlyAlaLeuGlnSerLeuLeuGlyThrGlnXaa
           100             105             110

XaaXaaXaaGlyArgThrThrAlaHisXaaAspProAsnAlaIlePhe
     115             120    122             125

LeuSerPheGlnHisLeuLeuArgGlyLysValArgPheLeuMetLeu
     130             135             140

ValGlyGlySerThrLeuCysValArg
145           150    153
``` wherein;

Xaa at position 37 is Thr, Asp or Glu;

Xaa at position 46 is Phe, Ala, Val, Leu, Ile, Pro, Trp, or Met;

Xaa at position 47 is Ser, Asp or Glu;

Xaa at position 112 is deleted or Leu, Ala, Val, Ile, Pro, Phe, Trp, or Met;

Xaa at position 113 is deleted or Pro, Phe, Ala, Val, Leu, Ile, Trp, or Met;

Xaa at position 114 is deleted or Pro, Phe, Ala, Val, Leu, Ile, Trp, or Met;

Xaa at position 115 is deleted or Gln, Gly, Ser, Thr, Tyr, or Asn;

Xaa at position 122 is Lys, Arg, His, Glu, or Asp;

and with the proviso that at least one of the amino acids designated by Xaa are different from the corresponding amino acids of native c-mpl ligand (1–332). These c-mpl ligand variants may have an improved biological profile, such as increased proliferative activity and/or decreased side-effects, and/or improved physical properties, such as improved half-life, stability, and/or re-fold efficiencies.

In addition to the use of the c-mpl ligands of the present invention in vivo, it is envisioned that in vitro uses would include the ability to stimulate bone marrow and blood cell activation and growth before infusion into patients.

The present invention also encompasses chimera proteins comprising recombinant human c-mpl ligand muteins joined to one or more colony stimulating factor (CSF) including, cytokines, lymphokines, interleukins, hematopoietic growth factors (herein collectively referred to as "colony stimulating factors") which include GM-CSF, CSF-1, G-CSF, M-CSF, erythropoietin (EPO), IL-1, IL-2, IL-3, IL-4, IL-5, IL-6, IL-7, IL-8, IL-9, IL-10, IL-11, IL-12, IL-13, IL-15, IL-16, LIF, flt3/flk2, human growth hormone, B-cell growth factor, B-cell differentiation factor, eosinophil differentiation factor and stem cell factor (SCF) also known as steel factor or c-kit ligand or IL-3 variant with or without a linker. These human c-mpl ligand muteins may contain amino acid substitutions, deletions and/or insertions and may also have amino acid deletions at either/or both the N- and C-termini.

This invention encompasses mixed function colony stimulating factors (chimera proteins) formed from covalently linked polypeptides, each of which may act through a different and specific cell receptor to initiate complementary biological activities. These chimeras may be characterized by having the usual activity of both of the peptides forming the chimera molecule or it may be further characterized by having a biological or physiological activity greater than simply the additive function of the presence of human c-mpl ligand or the second colony stimulating factor alone. The chimera molecule may also unexpectedly provide an enhanced effect on the activity or an activity different from that expected by the presence of human c-mpl ligand or the second colony stimulating factor. The chimera molecule may also have an improved activity profile which may include reduction of undesirable biological activities associated with native human c-mpl ligand or native cytokine.

In addition to the use of the chimera molecules of the present invention in vivo, it is envisioned that in vitro uses would include the ability to stimulate bone marrow and blood cell activation and growth before infusion into patients.

The present invention also encompasses recombinant human c-mpl ligand variant or mutant proteins (muteins) co-administrated with one or more additional colony stimulating factors (CSF) including, cytokines, lymphokines, interleukins, hematopoietic growth factors (herein collectively referred to as "colony stimulating factors") include GM-CSF, CSF-1, G-CSF, M-CSF, erythropoietin (EPO), IL-1, IL-2, IL-3, IL-4, IL-5, IL-6, IL-7, IL-8, IL-9, IL-10, IL-11, IL-12, IL-13, IL-15, IL-16, LIF, flt3/flk2, human growth hormone, B-cell growth factor, B-cell differentiation factor, eosinophil differentiation factor and stem cell factor (SCF) also known as steel factor or c-kit ligand. This invention encompasses co-administered colony stimulating factors, each of which may act through a different and specific cell receptor to initiate complementary biological activities. Co-administration of c-mpl ligand and other colony stimulating factors may be characterized by having the usual activity of both of the peptides or it may be further characterized by having a biological or physiological activity greater than simply the additive function of the presence of human c-mpl ligand or the second colony stimulating factor alone. The co-administration may also unexpectedly provide an enhanced effect on the activity or an activity different from that expected by the presence of human c-mpl ligand or the second colony stimulating factor or human c-mpl ligand variant. The co-administration may also have an improved activity profile which may include reduction of undesirable biological activities associated with native human c-mpl ligand or native cytokine.

In addition to the use of co-administration of the present invention in vivo, it is envisioned that in vitro uses would include the ability to stimulate bone marrow and blood cell activation and growth before infusion into patients.

It is also envisioned that c-mpl ligands of the present invention alone, co-administered with other colony stimulating factors, or as a component of a chimera molecule would be useful in blood banking. The c-mpl ligand would be given to a blood donor prior to giving blood to elevate their platelet count, increasing the number of platelets from each donor and thereby decreasing the cost of platelet transfusions.

Preferably the c-mpl ligand muteins of the present invention are co-administrated with or comprise a chimera protein with SCF, c-kit ligand, flt3/flk2, G-CSF, IL-3 or IL-3 variant.

Most preferably the c-mpl ligand muteins of the present invention are co-administrated with or comprise a chimera protein with G-CSF, or IL-3 variant.

DETAILED DESCRIPTION OF THE INVENTION

Variants of c-mpl ligand of the present invention may be useful in the treatment of diseases characterized by a decreased levels of megakaryocyte cells of the hematopoietic system.

A variant or mutein of c-mpl ligand may be useful in the treatment or prevention of thrombocytopenia. Currently the only therapy for thrombocytopenia is platelet transfusions which are costly and carry the significant risks of infection (HIV, HBV) and alloimunization. A variant or mutein of c-mpl ligand may alleviate or diminish the need for platelet transfusions. Severe thrombocytopenia may result from genetic defects such as Fanconi's Anemia, Wiscott-Aldrich, or May-Hegglin syndromes. Acquired thrombocytopenia may result from auto- or allo-antibodies as in Immune Thrombocytopenida Purpura, Systemic Lupus Erythromatosis, hemolytic anemia, or fetal maternal incompatibility. In addition, splenomegaly, disseminated intravascular coagulation, thrombotic thrombocytopenic purpura, infection or prosthetic heart valves may result in thrombocytopenia. Severe thrombocytopenia may also result from chemotherapy and/or radiation therapy or cancer. Thrombocytopenia may also result from marrow invasion by carcinoma, lymphoma, leukemia or fibrosis. c-mpl ligand of the present invention may be useful in the mobilization of hematopoietic progenitors and stem cells into peripheral blood. Peripheral blood derived progenitors have been shown to be effective in reconstituting patients in the setting of autologous marrow transplantation. Hematopoietic growth factors including G-CSF and GM-CSF have been shown to enhance the number of circulating progenitors and stem cells in the peripheral blood. This has simplified the procedure for peripheral stem cell collection and dramatically decreased the cost of the procedure by decreasing the number of plasmaphereses required. The c-mpl ligand of the present invention may be useful in mobilization of stem cells and further enhance the efficacy of peripheral stem cell transplantation. The c-mpl ligand may also be useful to increase platelet counts in platelet donors prior to apheresis to increase the number of platelets recovered from each donor.

Many drugs may cause bone marrow suppression or hematopoietic deficiencies. Examples of such drugs are AZT, DDI, alkylating agents and anti-metabolites used in chemotherapy, antibiotics such as chloramphenicol, penicillin, gancyclovir, daunomycin and sulfa drugs, phenothiazones, tranquilizers such as meprobamate, analgesics such as aminopyrine and dipyrone, anti convulsants such as phenytoin or carbamazepine, antithyroids such as propylthiouracil and methimazole and diuretics. c-mpl ligands may be useful in preventing or treating the bone marrow suppression or hematopoietic deficiencies which often occur in patients treated with these drugs.

Hematopoietic deficiencies may also occur as a result of viral, microbial or parasitic infections and as a result of treatment for renal disease or renal failure, e.g., dialysis. c-mpl ligand may be useful in treating such hematopoietic deficiency.

The proliferation and development of stem cells and lineage-restricted progenitor cells is controlled by a large number hematopoietic growth factors or cytokines. The role of the growth factors in vivo is complex and incompletely understood. Some growth factors, such as Interleukin-3 (IL-3), are capable of stimulating both multipotent stem cells as well as committed progenitor cells of several lineages. Other factors, such as Erythropoietin (EPO) and c-mpl ligand, are lineage restricted. Hematopoiesis requires a complex series of cellular events in which stem cells generate continuously into large populations of maturing cells in all major lineages. Most of these proliferative regulators can stimulate one or another type of colony formation in vitro, the precise pattern of colony formation stimulated by each regulator is quite distinctive. No two regulators stimulate exactly the same pattern of colony formation, as evaluated by colony numbers or, more importantly, by the lineage and maturation pattern of the cells making up the developing colonies. Proliferative responses can most readily be analyzed in simplified in vitro culture systems. Three quite different parameters can be distinguished: alteration in colony size, alteration in colony numbers and cell lineage. Two or more factors may act on the progenitor cell, inducing the formation of larger number of progeny thereby increasing the colony size. Two or more factors may allow increased number of progenitor cells to proliferate either because distinct subsets of progenitors cells exist that respond exclusively to one factor or because some progenitors require stimulation by two or more factors before being able to respond. Activation of additional receptors on a cell by the use of two or more factors is likely to enhance the mitotic signal because of coalescence of initially differing signal pathways into a common final pathway reaching the nucleus (Metcalf D., *Nature* 339:27, 1989). Other mechanisms could explain synergy. For example, if one signaling pathway is limited by an intermediate activation of an additional signaling pathway by a second factor may result in a superadditive response. In some cases, activation of one receptor type can induce a enhanced expression of other receptors (Metcalf D., *Blood* 82:3515–3523, 1993). Two or more factors may result in a different pattern of cell lineages then from a single factor. The use of chimera molecules comprising the c-mpl ligand of the present invention or the co-administration of the c-mpl ligands of the present invention may have the potential clinical advantage resulting from a proliferative response that is not possible by any single factor.

Novel compounds of this invention are represented by a formula selected from the group consisting of $R_1$—L—$R_2$, $R_2$—L—$R_1$, $R_1$—$R_2$, $R_2$—$R_1$, $R_1$—L—$R_1$ and $R_1$—$R_1$ where R1 is a c-mpl ligand variant and R2 is a colony stimulating factor with a different but complementary activity. By complementary activity is meant activity which enhances or changes the response to another cell modulator. The R1 polypeptide is joined either directly or through a linker segment to the R2 polypeptide. The term "directly" defines chimeras in which the polypeptides are joined without a peptide linker. Thus L represents a chemical bound or polypeptide segment to which both R1 and R2 are joined in frame, most commonly L is a linear peptide to which R1 and R2 are bound by amide bonds linking the carboxy terminus of R1 to the amino terminus of L and carboxy terminus of L to the amino terminus of R2. By "joined in frame" is meant that there is no translation termination or disruption between the reading frames of genes encoding R1 and R2. A nonexclusive list of other growth factors, colony stimulating factors (CSFs), cytokine, lymphokine, interleukin, hematopoietic growth factor within the definition of R2, which can be joined to a c-mpl ligand variant of the present invention include GM-CSF, CSF-1, G-CSF, M-CSF, erythropoietin (EPO), IL-1, IL-2, IL-3, IL-4, IL-5, IL-6, IL-7, IL-8, IL-9, IL-10, IL-11, IL-12, IL-13, IL-15, IL-16, LIF, flt3/flk2, human growth hormone, B-cell growth factor, B-cell differentiation factor, eosinophil differentiation factor and stem cell factor (SCF) also known as steel factor or c-kit ligand. Additionally, this invention encompasses the use of modified R2 molecules or mutated or modified DNA sequences encoding these R2 molecules. The present invention also includes chimera molecules in which R2 is a hIL-3 variant. A "hIL-3 variant" is defined as a hIL-3 variant disclosed in WO 94/12639, WO 94/12638 and WO 95/00646 as well as other variants known in the art.

The linking group (L) is generally a polypeptide of between 1 and 500 amino acids in length. The linkers joining the two molecules are preferably designed to (1) allow the two molecules to fold and act independently of each other, (2) not have a propensity for developing an ordered secondary structure which could interfere with the functional domains of the two proteins, (3) have minimal hydrophobic or charged characteristic which could interact with the functional protein domains and (4) provide steric separation of R1 and R2 such that R1 and R2 could interact simultaneously with their corresponding receptors on a single cell. Typically surface amino acids in flexible protein regions include Gly, Asn and Ser. Virtually any permutation of amino acid sequences containing Gly, Asn and Ser would be expected to satisfy the above criteria for a linker sequence. Other neutral amino acids, such as Thr and Ala, may also be used in the linker sequence. Additional amino acids may also be included in the linkers due to the addition of unique restriction sites in the linker sequence to facilitate construction of the chimeras. More details about methods of making such chimera molecules can be found in WO 95/21254 which is herein incorporated by reference in it's entirety.

A c-mpl ligand that has reduced activity may be useful in a chimera molecule. For example it may be advantageous to have only a small amount of megakaryocyte maturation and platelet production activity relative to the activity of the other growth factor component of the chimera molecule, such as IL-3 which stimulates multipotent stem cells as well as committed progenitor cells of several lineages including megakaryocytes. Conversely a c-mpl ligand that has increased activity would be useful when increased megakaryocyte maturation and platelet production activity relative to the activity of the other growth factor component of the chimera molecule is desired.

The c-mpl ligands of the present invention may also be a component of a chimera, joined to a modified mouse Fc (IgG2a) constant region (Gross A. H. et al, *J. Clin. Invest.* 95:2783–2789, [1995]). Such a chimera might be useful for purification of the c-mpl ligand, increasing protein stability and the formation of a dimer through the Fc region.

One aspect of the present invention provides a method for selective ex-vivo expansion of stem cells. The term "stem cell" refers to the totipotent hematopoietic stem cells as well as early precursors and progenitor cells which can be isolated from bone marrow, spleen or peripheral blood. The term "expanding" refers to the differentiation and proliferation of the cells. The present invention provides a method for selective ex-vivo expansion of stem cells, comprising the steps of; (a) separating stem cells from other cells, (b) culturing said separated stem cells with a selected media which comprises a c-mpl ligand or chimera protein(s) which are in part comprised of a c-mpl ligand and (c) harvesting said stems cells. Stem cells as well as committed progenitor cells destined to become neutrophils, erythrocytes, platelets. etc., may be distinguished from most other cells by the presence or absence of particular progenitor marker antigens, such as CD34, that are present on the surface of these cells and/or by morphological characteristics. The phenotype for a highly enriched human stem cell fraction is reported as CD34+, Thy-1+ and lin-, but it is to be understood that the present invention is not limited to the expansion of this stem cell population. The CD34+ enriched human stem cell fraction can be separated by a number of reported methods, including affinity columns or beads, magnetic beads or flow cytometry using antibodies directed to surface antigens such as the CD34+. Further, physical separation methods such as counterflow elutriation may be used to enrich hematopoietic progenitors. The CD34+ progenitors are heterogeneous, and may be divided into several sub-populations characterized by the presence or absence of co-expression of different lineage associated cell surface associated molecules. The most immature progenitor cells do not express any known lineage-associated markers, such as HLA-DR or CD38, but they may express CD90(thy-1). Other surface antigens such as CD33, CD38, CD41, CD71, HLA-DR or c-kit can also be used to selectively isolate hematopoietic progenitors. The separated cells can be incubated in selected medium in a culture flask, sterile bag or in hollow fibers. Various colony stimulating factors may be utilized in order to selectively expand cells. Representative factors that have been utilized for ex-vivo expansion of bone marrow include, c-kit ligand, IL-3, G-CSF, GM-CSF, IL-1, IL-6, IL-11, flt-3 ligand or combinations thereof. The proliferation of the stem cells can be monitored by enumerating the number of stem cells and other cells, by standard techniques (e.g. hemacytometer, CFU, LTCIC) or by flow cytometry prior and subsequent to incubation.

Several methods for ex-vivo expansion of stem cells have been reported utilizing a number of selection methods and expansion using various colony stimulating factors including c-kit ligand (Brandt et al., *Blood* 8 3:1507–1514 [1994], McKenna et al., *Blood* 86:3413–3420 [1995]), IL-3 (Brandt et al., *Blood* 83:1507–1514 [1994], Sato et al., *Blood* 82:3600–3609 [1993]), G-CSF (Sato et al., *Blood* 82:3600–3609 [1993]), GM-CSF (Sato et al., *Blood* 82:3600–3609 [1993]), IL-1 (Muench et al., *Blood* 81:3463–3473 [1993]), IL-6 (Sato et al., *Blood* 8 2:3600–3609 [1993]), IL-11 (Lemoli et al., *Exp. Hem.* 21:1668–1672 [1993], Sato et al., *Blood* 82:3600–3609 [1993]), flt-3 ligand (McKenna et al., *Blood* 86:3413–3420 [1995]) and/or combinations thereof (Brandt et al., *Blood* 83:1507–1514 [1994], Haylock et al., *Blood* 80:1405–1412 [1992], Koller et al., *Biotechnology* 11:358–363 [1993], (Lemoli et al., *Exp. Hem.* 21:1668–1672 [1993]), McKenna et al., *Blood* 86:3413–3420 [1995], Muench et al., *Blood* 81:3463–3473 [1993], Patchen et al., *Biotherapy* 7:13–26 [1994], Sato et al., *Blood* 82:3600–3609 [1993], Smith et al., *Exp. Hem.* 21:870–877 [1993], Steen et al., *Stem Cells* 12:214–224 [1994], Tsujino et al., *Exp. Hem>*21:1379–1386 [1993]). Among the individual colony stimulating factors, hIL-3 has been shown to be one of the most potent in expanding peripheral blood CD34+ cells (Sato et al., *Blood* 82:3600–3609 [1993], Kobayashi et al., *Blood* 73:1836–1841 [1989]). However, no single factor has been shown to be as effective as the combination of multiple factors. The present invention provides methods for ex vivo expansion that utilize molecules that are more effective than IL-3 alone.

Another projected clinical use of growth factors has been in the in vitro activation of hematopoietic progenitors and stem cells for gene therapy. Due to the long life-span of hematopoietic progenitor cells and the distribution of their daughter cells throughout the entire body, hematopoietic progenitor cells are good candidates for ex vivo gene transfection. In order to have the gene of interest incorporated into the genome of the hematopoietic progenitor or stem cell one needs to stimulate cell division and DNA replication. Hematopoietic stem cells cycle at a very low frequency which means that growth factors may be useful to promote gene transduction and thereby enhance the clinical prospects for gene therapy. Potential applications of gene therapy (review Crystal, *Science* 270:404–410 [1995]) include; 1) the treatment of many congenital metabolic disorders and immunodifiencies (Kay and Woo, *Trends Genet.* 10:253–257 [1994]), 2) neurological disorders (Freedmann, *Trends Genet.* 10:210–214 [1994]), 3) cancer (Culver and Blaese, *Trends Genet.* 10:174–178 [1994]) and 4) infectious diseases (Gilboa and Smith, *Trends Genet.* 10:139–143 [1994]).

There are a variety of methods, known to those with skill in the art, for introducing genetic material into a host cell. A number of vectors, both viral and non-viral have been developed for transferring therapeutic genes into primary cells. Viral based vectors include; 1) replication-deficient recombinant retrovirus (Boris-Lawrie and Temin, *Curr. Opin. Genet. Dev.* 3:102–109 [1993], Boris-Lawrie and Temin, *Annal. New York Acad. Sci.* 716:59–71 [1994], Miller, *Current Top. Microbiol. Immunol.* 158:1–24 [1992]) and replication-deficient recombinant adenovirus (Berkner, *BioTechniques* 6:616–629 [1988], Berkner, *Current Top. Microbiol. Immunol.* 158:39–66 [1992], Brody and Crystal, *Annal. New York Acad. Sci.* 716:90–103 [1994]). Non-viral based vectors include protein/DNA complexes (Cristiano et al., *PNAS USA.* 90:2122–2126 [1993], Curiel et al., *PNAS USA* 88:8850–8854 [1991], Curiel, *Annal. New York Acad. Sci.* 716:36–58 [1994]), electroporation and liposome mediated delivery such as cationic liposomes (Farhood et al., *Annal. New York Acad. Sci.* 716:23–35 [1994]).

The present invention provides an improvement to the existing methods of expanding hematopoietic cells, which new genetic material has been introduced, in that it provides methods utilizing chimera proteins that have improved biological, including an activity not seen by any single colony stimulation factor and/or physical properties.

The present invention also provides genes, encoding c-mpl ligands and chimera proteins, which can be introduced into cells for gene therapy.

As another aspect of the present invention, there is provided a novel method for producing the novel family of human c-mpl ligand muteins. The method of the present invention involves culturing a suitable cell or cell line, which has been transformed with a vector containing a DNA sequence coding for expression of a novel c-mpl ligand mutant polypeptide. Suitable cells or cell lines may be bacterial cells. For example, the various strains of *E. coli* are well-known as host cells in the field of biotechnology. Examples of such strains include *E. Coli* strains JM101 (Yanisch-Perron, et al., *Gene*, 33: 103–119 [1985]) and MON105 (Obukowicz, et al., *Appl. and Envir. Micr*., 58: 1511–1523 [1992]). Various strains of *B. subtilis* may also be employed in this method. Many strains of yeast cells known to those skilled in the art are also available as host cells for expression of the polypeptides of the present invention.

Also suitable for use in the present invention are mammalian cells, such as Chinese hamster ovary cells (CHO). General methods for expression of foreign genes in mammalian cells are reviewed in: Kaufman, R. J. (1987) High level production of proteins in mammalian cells, in Genetic Engineering, Principles and Methods, Vol. 9, J. K. Setlow, editor, Plenum Press, New York. An expression vector is constructed in which a strong promoter capable of functioning in mammalian cells drives transcription of a eukaryotic secretion signal peptide coding region, which is translationally joined to the coding region for the c-mpl ligand variant. For example, plasmids such as pcDNA I/Neo, pRc/RSV, and pRc/CMV (obtained from Invitrogen Corp., San Diego, Calif.) can be used. After construction of the vector containing the c-mpl ligand gene, the vector DNA is transfected into mammalian cells. Such cells can be, for example, the COS7, HeLa, BHK, CHO, or mouse L lines. The cells can be cultured, for example, in DMEM media (JRH Scientific). The c-mpl ligand secreted into the media can be recovered by standard biochemical approaches following transient expression 24–72 hours after transfection of the cells or after establishment of stable cell lines following selection for neomycin resistance. The selection of suitable mammalian host cells and methods for transformation, culture, amplification, screening and product production and purification are known in the art. See, e.g., Gething and Sambrook, *Nature* 293:620–625 [1981], or alternatively, Kaufman et al., *Mol. Cell. Biol*. 5 (7):1750–1759 [1985] or Howley et al., U.S. Pat. No. 4,419,446. Another suitable mammalian cell line is the monkey COS-1 cell line. A similarly useful mammalian cell line is the CV-1 cell line.

Where desired, insect cells may be utilized as host cells in the method of the present invention. See, e.g. Miller et al, Genetic Engineering, 8:277–298 (Plenum Press 1986) and references cited therein. In addition, general methods for expression of foreign genes in insect cells using Baculovirus vectors are described in: Summers, M. D. and Smith, G. E. (1987)—A manual of methods for Baculovirus vectors and insect cell culture procedures, Texas Agricultural Experiment Station Bulletin No. 1555. An expression vector is constructed comprising a Baculovirus transfer vector, in which a strong Baculovirus promoter (such as the polyhedron promoter) drives transcription of a eukaryotic secretion signal peptide coding region, which is translationally joined to the coding region for the c-mpl ligand polypeptide. For example, the plasmid pVL1392 (obtained from Invitrogen Corp., San Diego, California) can be used. After construction of the vector carrying the c-mpl ligand gene, two micrograms of this DNA is cotransfected with one microgram of Baculovirus DNA (see Summers & Smith, 1987) into insect cells, strain SF9. Pure recombinant Baculovirus carrying the hIL-3 variant is used to infect cells cultured, for example, in Excell 401 serum-free medium (JRH Biosciences, Lenexa, Kansas). The c-mpl ligand secreted into the medium can be recovered by standard biochemical approaches.

Another aspect of the present invention provides plasmid DNA vectors for use in the method of expression of these novel c-mpl ligand muteins. These vectors contain the novel DNA sequences described above which code for the novel polypeptides of the invention. Appropriate vectors which can transform microorganisms capable of expressing the c-mpl ligand muteins include expression vectors comprising nucleotide sequences coding for the c-mpl ligand muteins joined to transcriptional and translational regulatory sequences which are selected according to the host cells used.

Vectors incorporating modified sequences as described above are included in the present invention and are useful in the production of the c-mpl ligand mutant polypeptides. The vector employed in the method also contains selected regulatory sequences in operative association with the DNA coding sequences of the invention and capable of directing the replication and expression thereof in selected host cells.

Other aspects of the present invention are methods and therapeutic compositions for treating the conditions referred to above. Such compositions comprise a therapeutically effective amount of one or more of the c-mpl ligand muteins of the present invention in a mixture with a pharmaceutically acceptable carrier. This composition can be administered either parenterally, intravenously or subcutaneously. When administered, the therapeutic composition for use in this invention is preferably in the form of a pyrogen-free, parenterally acceptable aqueous solution. The preparation of such a parenterally acceptable protein solution, having due regard to pH, isotonicity, stability and the like, is within the skill of the art.

The dosage regimen involved in a method for treating the above-described conditions will be determined by the attending physician considering various factors which modify the action of drugs, e.g. the condition, body weight, sex and diet of the patient, the severity of any infection, time of administration and other clinical factors. Generally, a daily regimen may be in the range of 0.1–100 $\mu$g/kg of non-glycosylated c-mpl ligand protein per kilogram of body weight. Dosages would be adjusted relative to the activity of a given mutein and it would not be unreasonable to note that dosage regimens may include doses as low as 0.1 microgram and as high as 1 milligram per kilogram of body weight per day. In addition, there may exist specific circumstances where dosages of c-mpl ligand mutein would be adjusted higher or lower than the range of 0.1–100 micrograms per kilogram of body weight. These include co-administration with other CSF or growth factors; co-administration with chemotherapeutic drugs and/or radiation; the use of glycosylated c-mpl ligand mutein; and various patient-related issues mentioned earlier in this section. As indicated above, the therapeutic method and compositions may also include co-administration with other human factors. A non-exclusive list of other appropriate hematopoietins, CSFs and interleukins for simultaneous or serial co-administration or chimera with the polypeptides of the present invention includes GM-CSF, CSF-1, G-CSF, Meg-CSF, M-CSF, erythropoietin (EPO), IL-1, IL-3, IL-4, IL-2, IL-5, IL-6, IL-7, IL-8, IL-9, IL-10, IL-11, IL-12, IL-13, IL-15, IL-16, LIF, flt2/flk3 ligand, B-cell growth factor, B-cell differentiation factor and eosinophil differentiation factor, stem cell factor (SCF) also known as steel factor or c-kit ligand (herein collectively referred to as "colony stimulating factors"), or combinations thereof. In addition to the list above, IL-3 variants taught in WO 94/12638, WO 94/12639 and WO 95/00646 can be co-administered or joined as a chimera with the c-mpl ligand polypeptides of the present invention. The c-mpl ligands of the present invention can be joined or co-administered as with another "colony stimulating factor" as discussed above in a fashion taught in WO 95/20977 and WO 95/21254. The dosage recited above would be adjusted to compensate for such additional components in the therapeutic composition. Progress of the treated patient can be monitored by periodic assessment of the hematological profile, e.g., differential cell count and the like.

All references, patents or applications cited herein are incorporated by reference in their entirety.

Recombinant DNA methods

Unless noted otherwise, all specialty chemicals were obtained from Sigma Co., (St. Louis, Mo.). Restriction endonucleases and T4 DNA ligase were obtained from New England Biolabs (Beverly, Mass.).

Reverse transcriotase/Dolymerase chain reaction

The alternate forms of c-mpl ligand can be isolated using reverse transcriptase/polymerase chain reaction (RT/PCR) technology. Synthetic primers are designed so that they would anneal to either c-mpl ligand DNA or mRNA (c-mpl ligand sequence based on Genebank accession #L33410 or de Sauvage et al., *Nature* 369: 533–538 [1994]) for priming first-strand complementary DNA (cDNA) synthesis. The resulting cDNA is used as a template in PCR (Saiki, 1985) to generate double-stranded DNA (dsDNA or DNA) which can be used in additional PCR or digested with appropriate restriction enzymes for transfer to Baculovirus, mammalian or bacterial, such as *E. coli*, expression plasmids. For the reverse transcriptase (RT) reaction, human fetal (lot #38130) and adult liver (lot #46018) A+ RNA can be obtained from Clontech (Palo Alto, Calif.). The RT reactions are carried out using a cDNA Cycle™ Kit obtained from Invitrogen (San Diego, Calif.). One microgram (ug) of each RNA sample is denatured at 65° C. for 10 min. in the presence of either random primers, oligo dT primer or a specific 3' anti-sense primer. Following denaturation, the samples are cooled for 2 min. on ice and spun down for 10 sec. at 10,000×g. RNAse inhibitor, reverse transcriptase buffer, deoxynucleotides, sodium pyrophosphate and reverse transcriptase are added as described by manufacturer, and the 20 microliter reaction is incubated at 42° C. for 1 hr. For PCR specific 5' sense and 3' anti-sense primers are added to the RT reactions and the PCR is carried out using reagents from Boehringer Mannheim (Indianapolis, Ind.) or Perkin-Elmer (Norwalk, Conn.) as described by the manufacturers using Taq polymerase. The PCR reactions are subjected to 30 cycles of the following; 1 min. @ 94° C., 1 min. @ 58° C., 90 sec. @ 72° C. An equal volume of loading dye (0.01% each bromophenol blue and xylene cyanole blue) is added to 10 microliters of the final product for electrophoresis through a 1% SeaKem$^R$ LE agarose (FMC, Rockland, Me.) gel in the presence of 1× TBE/EtBr (Trisborate-EDTA plus ethidium bromide; Sambrook et al., *Molecular Cloning: A Laboratory Manual*, 2nd ed., Cold Spring Harbor Laboratory Press, Cold Spring Harbor, N.Y., [1989]). For molecular weight standards, 1 microgram of phiX174 phage DNA digested with HaeIII restriction enzyme (New England Biolabs, Beverly, Mass.) is loaded onto the gel. The product (about 1090 base pairs) is visualized using a short-wave UV light source. The reactions are purified using a Wizard™ PCR Preps kit from Promega (Madison, Wis.). Briefly, the PCR reactions are added to 100 microliters of Direct Purification buffer, and 1 milliliter (mL) of PCR Preps DNA Purification Resin is added to this mixture. After 1 minute incubation at 24° C., the supernatant is removed by vacuum filtration through a filtration column. Two mLs of 80% isopropanol is used to wash the resin via vacuum filtration. The column containing the resin is then subjected to centrifugation at 10,000×g for 30 seconds to remove residual isopropanol. The PCR product is eluted with 50 microliters of 10 mM Tris-HCl, 1 mM EDTA, pH7.4, via centrifugation at 10,000×g for 30 seconds followed by transfer of supernatant to a new tube.

Subcloning c-mpl ligand forms into expression vectors

The c-mpl ligand PCR products are digested with the appropriate restriction enzymes for ligation to either baculovirus, mammalian or *E. coli* expression vectors. The mammalian expression vectors are derivatives of pMON3359 which is a pUC18-based vector containing a mammalian expression cassette. The cassette includes a herpes simplex viral promoter IE110 (−800 to +120) and a SV40 late poly-adenylation (poly-A) signal which has been subcloned into the pUC18 polylinker (See Hippenmeyer et al., *Bio/Technology*: 1037–1041 [1993]). Restriction enzyme digestions are incubated for 1 hour at 37° C. as described by the manufacturer prior to electrophoresis through a 1% agarose/1×TBE/EtBr gel. Fragments are first visualized by long-wave UV and gel-purified using a Qiaex DNA Extraction kit (Qiagen, Chatsworth, Calif.). The DNA fragments are purified from the resin by agarose solubilization, addition of a DNA-binding resin, and extensive washing of the resin prior to elution with water. The purified DNA products are combined at a molar excess of PCR product to vector and the ligation reactions are carried out according to the manufacturer's recommended conditions for T4 DNA ligase. The *E. coli* expression vectors that direct high-level production of heterologous proteins in the cytoplasm are derivatives of that described elsewhere (Olins et al., *Methods Enzym.*, 185: 115–119 [1988] and Rangwala et al., *Gene*, 122: 263–269 [1992]). The expression cassette consists of the recA promoter and T7 gene 10 ribosome binding site (RBS) as well as an M13 origin of replication or a tandem inverted repeat of a phage P22 gene which acts as a transcription terminator. These cassettes are on a plasmid with the pBR327 origin of replication and encode a gene either for spectinomycin or ampicillin resistance.

Transformation of *E. coli* strains

*E. coli* strains such as TG1 (Amersham Corp., Arlington Heights, Ill.) JM101 (Yanish-Perron C., et al. *Gene* 33: 103–119 [1985]), or DH5α (Life Technologies, Gaithersburg, Md.) are used for transformation of ligation reactions and are the source of plasmid DNA for transfecting mammalian cells. *E. coli* strains MON105 and JM101 can be obtained from the American Type Culture Collection (ATCC, Rockville, Md.) and are hosts for expressing alternate forms of c-mpl ligand in the cytoplasm and periplasmic space of *E. coli*.

MON105 ATCC#55204: F-, lambda-,IN(rrnD, rrE)1, rpoD+, rpoH358

JM101 ATCC#33876: delta (pro lac), supE, thi, F' (traD36, proA+B+, lacI$^q$, lacZdeltaM15)

TG1: delta (lac-pro), supE, thi, hsdD5/F' (traD36, proA+B+, lacI$^q$, lacZdeltaM15)

DH5α: F-Φ80dlacZM15 Δ(lacZYA-argF)U169 deoR recA1 endA1 hsdR17 ($r_K$−, $m_K$+) supE44 λ- thi-1 gyrA96 relA1

*E. coli* strains can be rendered competent to take up DNA using a CaCl$_2$ method. Typically, 20 to 50 mLs of cells are grown in LB medium (1% bacto-tryptone, 0.5% bacto-yeast extract, 150 millimolar NaCl) to a density of approximately 1.0 optical density units at 600 nanometers ($OD_{600}$) as measured by a Baush & Lomb Spectronic spectrophotometer (Rochester, N.Y.). The cells are collected by centrifugation and resuspended in one-fifth culture volume of $CaCl_2$ solution (50 millimolar $CaCl_2$, 10 millimolar Tris-HCl, pH7.4) and are held at 4° C. for 30 minutes. The cells are again collected by centrifugation and resuspended in one tenth culture volume of $CaCl_2$ solution. Ligated DNA is added to 0.2 mL of these cells, and the samples are held at 4° C. for 1 hour. The samples are shifted to 42° C. for two minutes and 1.0 mL of LB is added prior to shaking the samples at 37° C. for one hour. Cells from these samples are spread on plates (LB medium plus 1.5% bacto-agar) containing either ampicillin (100 micrograms/mL, ug/mL) when selecting for ampicillin-resistant transformants, or spectinomycin (75 ug/mL) when selecting for spectinomycin-resistant transformants. The plates are incubated overnight at 37° C. Single colonies are picked, grown in LB supplemented with appropriate antibiotic for 6–16 hours at 37° C. with shaking. Colonies are picked and inoculated into LB plus appropriate antibiotic (100 ug/mL ampicillin or 75 ug/mL spectinomycin) and are grown at 37° C. while shaking. Before harvesting the cultures, 1 ul of cells are analyzed by PCR for the presence of a c-mpl ligand gene. The PCR is carried out using a combination of primers that anneal to the c-mpl ligand gene and/or vector. After the PCR is complete, loading dye is added to the sample followed by electrophoresis as described earlier. A gene has been ligated to the vector when a PCR product of the expected size is observed.

DNA isolation and characterization

Plasmid DNA is isolated using the Promega Wizard™ Miniprep kit (Madison, Wis.) or the Qiagen QIAwell Plasmid isolation kits (Chatsworth, Calif.). Both kits follow the same general procedure for plasmid DNA isolation. Briefly, cells are pelleted by centrifugation (5000×g), plasmid DNA released with sequential NaOH & acid treatment, and cellular debris is removed by centrifugation (10000×g). The supernatant (containing the plasmid DNA) is loaded onto a column containing a DNA-binding resin, the column is washed, and plasmid DNA eluted with TE. Between 0.2 and 1.0 ug of plasmid DNA from the truncated c-mpl ligand clones is digested with appropriate restriction enzymes followed by electrophoresis as described earlier to confirm the presence of a c-mpl gene fragment released from the vector. E. coli harboring the desired plasmid DNA are inoculated into 100 mls of LB plus appropriate antibiotic for overnight growth at 37° C. in an air incubator while shaking. Plasmid DNA is isolated using the Qiagen Plasmid Midi kit (Chatsworth, Calif.) which is a scaled-up version of the Qiagen QIAwell Plasmid isolation kit described earlier. The DNA is used for DNA sequencing, further restriction enzyme digestion, additional subcloning of DNA fragments and transfection into mammalian or E. coli cells.

Purified recombinant double-stranded DNA is sequenced using either the Applied Biosystems Inc. (ABI, Foster City, Calif.) PRISM™ Ready Reaction DyeDeoxy™ Terminator Sequencing system or United States Biochemical (Cleveland, Ohio) Sequenase™ Version 2.0 DNA Sequencing kit. The ABI system relies on incorporation of four fluorescence labelled dideoxy nucleotides into single-stranded DNA during multiple rounds of amplification. Plasmid DNA and a sequencing primer are added to the reaction mixture (including Taq DNA polymerase, buffer and nucleotides), which is subjected to 25 cycles of amplification (30 seconds at 96° C., 15 seconds at 50° C., 4 minutes at 60° C.). Following amplification, unincorporated nucleotides are removed using Centri-Sep spin columns (equilibrated in water) as described by Princeton Separations, Inc. (Adelphia, N.J.). Briefly, the samples are loaded onto a column that has excess water removed by centrifugation (700×g) for 2 minutes, and the purified sequencing product is eluted by centrifugation (700×g) for 4 minutes. The samples are then dried down in a Speed Vac (Savant, Hicksville, N.Y.) prior to addition of loading solution. The samples are electrophoresed through a 4.75% polyacrylamide sequencing gel containing 7M urea in 1×TBE at 70 watts constant power. The ABI system uses a detector that recognizes each differentially labelled PCR product as they are being subjected to electrophoresis.

For the Sequenase™ sequencing system, plasmid DNA is denatured with NaOH and neutralized with ammonium hydroxide (as described by manufacturer) to provide single-stranded DNA for sequencing. After annealing a sequencing primer to the denatured DNA for 30 minutes in the presence of buffer, alpha[$^{33}$P] deoxy adenosine triphosphate, DTT, deoxy and dideoxy nucleotides are added. After 5 minutes at room temperature, the reaction is split into four tubes, each of which contains additional deoxy nucleotides as well as one type of dideoxy nucleotide per tube. After 5 minutes at 37° C., the reactions are terminated with loading dye. The samples are heated to 80° C. for 2 minutes and subjected to electrophoresis on a 6.0% polyacrylamide sequencing gel containing 7M urea in 1×TBE at 70 watts constant power. The gel is fixed in 10% acetic acid for 30 minutes and dried under a vacuum at 80° C. for 30 minutes. The dried gel is placed next to X ray film overnight at room temperature and the film is developed using an Eastman Kodak X-OMAT M20 processor (Rochester, N.Y.).

Production of novel forms of c-mpl ligand

Mammalian Cell Transfection/Production of Conditioned Media

The BHK-21 cell line can be obtained from the ATCC (Rockville, Md.). The cells are cultured in Dulbecco's modified Eagle media (DMEM/high-glucose), supplemented to 2 millimolar (mM) L-glutamine and 10% fetal bovine serum (FBS). This formulation is designated BHK growth media. Selective media is BHK growth media supplemented with 453 units/ml hygromycin B (Calbiochem, San Diego, Calif.). The BHK-21 cell line was previously stably transfected with the HSV transactivating protein VP16, which transactivates the IE110 promoter found on the plasmid pMON3359 (See Hippenmeyer et al., Bio/Technology:1037–1041 [1993]). The VP16 protein drives expression of genes inserted behind the IE110 promoter. BHK-21 cells expressing the transactivating protein VP16 is designated BHK-VP16. The plasmid pMON1118 (See Highkin et al., Poultry Sci. 70: 970–981 [1991]) expresses the hygromycin resistance gene from the SV40 promoter. A similar plasmid is available from ATCC, pSV2-hph.

BHK-VP16 cells are seeded into a 60 millimeter (mm) tissue culture dish at 3×10$^5$ cells per dish 24 hours prior to transfection. Cells are transfected for 16 hours in 3 mL of "OPTIMEM"™ (Gibco-BRL, Gaithersburg, Md.) containing 10 ug of plasmid DNA containing the gene of interest, 3 ug hygromycin resistance plasmid, pMON1118, and 80 ug of "LIPOFECTAMINE"™ (Gibco-BRL) per dish. The media is subsequently aspirated and replaced with 3 mL of growth media. At 48 hours post-transfection, media from each dish is collected and assayed for activity (transient conditioned media). The cells are removed from the dish by trypsin-EDTA, diluted 1:10 and transferred to 100 mm tissue culture dishes containing 10 mL of selective media. After approximately 7 days in selective media, resistant cells grow into colonies several millimeters in diameter. The colonies were removed from the dish with filter paper (cut to approximately the same size as the colonies and soaked in trypsin/EDTA) and transferred to individual wells of a 24 well plate containing 1 mL of selective media. After the clones are grown to confluence, the conditioned media is reassayed, and positive clones are expanded into growth media.

Expression and purification of recombinant c-mpl ligand proteins from *E. coli*

*E. coli* strain MON105 harboring the plasmid of interest are grown at 37° C. in M9 plus casamino acids medium with shaking in a air incubator Model G25 from New Brunswick Scientific (Edison, N.J.). Growth is monitored at $OD_{600}$ until it reaches a value of 1.0 at which time Nalidixic acid (10 milligrams/mL) in 0.1 N NaOH is added to a final concentration of 50 μg/mL. The cultures are then shaken at 37° C. for three to four additional hours. A high degree of aeration is maintained throughout culture period in order to achieve maximal production of the desired gene product. The cells are examined under a light microscope for the presence of inclusion bodies (IB). One mL aliquots of the culture are removed for analysis of protein content by boiling the pelleted cells, treating them with reducing buffer and electrophoresis via SDS-PAGE (see Maniatis et al. *Molecular Cloning: A Laboratory Manual*, [1982]). After centrifugation (5000×g) to pellet the cells, the first step in purification of the protein is either sonication or homogenization of the cells. For sonication, the cells are resuspended in one-tenth volume (based on culture size) sonication buffer (10 mM Tris-HCl, pH 7.5, 1 mM EDTA). These resuspended cells are subjected to several repeated sonication bursts using the microtip from a Sonicator cell disrupter, Model W-375 obtained from Heat Systems-Ultrasonics Inc. (Farmingdale, N.Y.). The extent of sonication is monitored by examining the homogenates under a light microscope. After all of the cells are disrupted, the homogenates are fractionated by centrifugation at 10000×g for 20 minutes at 4° C. in a JA-20 rotor and J2–21 centrifuge (Beckman, Fullerton, Calif.). Alternatively, the IBs are released from the cells by lysing the cells in sonication buffer with a Manton-Gaulin homogenizer (Holland) followed by centrifugation as above. The IB pellets, which are highly enriched for the recombinant protein, are then subjected to another round of sonication and centrifugation as described above. The recombinant protein is purified by a variety of standard methods. The most common methods involve solubilization of the IBs with 4–6 molar urea or guanidine-HCl buffers at pH 9–12, and air oxidation/folding in the presence of catalytic concentrations of cysteine, beta-mercaptoethanol or dithiothreitol for 24 to 72 hours. The protein is purified from *E. coli* contaminants using ion-exchange chromatography, such as Q-sepharose (anion) and S-sepharose (cation), gel filtration, hydrophobic chromatography or reversed phase HPLC. After dialysis against a low ionic strength buffer, the purified protein is stored frozen or lyophilized.

Additional details about recombinant DNA methods which may be used to create the variants and chimera proteins, express them in bacteria, mammalian cells or insect cells, purification and refold of the desired proteins and assays for determining the bioactvity of the proteins may be found in WO 95/00646, WO 94/12639, WO 94/12638, WO 95/20976, WO 95/21197, W095/20977, and WO 95/21254 which are hereby incorporated by reference in their entirety.

Further details known to those skilled in the art may be found in T. Maniatis, et al., *Molecular Cloning, A Laboratory Manual*, Cold Spring Harbor Laboratory (1982) and references cited therein, incorporated herein by reference; and in J. Sambrook, et al., *Molecular Cloning, A Laboratory Manual*, 2nd edition, Cold Spring Harbor Laboratory (1989) and references cited therein, incorporated herein by reference.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

Isolation of c-mpl ligand gene products

A. Reverse transcriptase reaction Human fetal (lot #38130) and adult liver (lot #46018) A+ RNA were obtained from Clontech (Palo Alto, Calif.). The first strand cDNA reactions were carried out using a cDNA Cycle™ Kit obtained from Invitrogen (San Diego, Calif.). In the first reverse transcriptase reaction (RT#1) random primers (supplied in cDNA Cycle# Kit) were used. In the second reverse transcriptase reaction (RT#2) oligo dT primer (supplied in cDNA Cycle™ Kit) and the specific 3' antisense primer, c-mplEcoRI [SEQ ID NO:23] were used. The c-mplEcoRI primer anneals to the 3' end of the c-mpl ligand gene coding sequence (bases #1257–1278 based on c-mpl ligand sequence from Genebank accession #L33410 or de Sauvage et al., *Nature* 369: 533–538 [1994]) and encodes an EcoRI restriction enzyme site 3' to the termination codon.

B. Polymerase chain reaction 1. 1–332 c-mpl ligand

For amplification of 1–332 amino acid c-mpl ligand gene fragments, the product of reverse transcriptase reactions RT#1 and RT#2 were used as templates in PCR. In the first polymerase chain reaction (PCR#1), RT#1 served as the template and the primers c-mplEcoRI [SEQ ID NO:23] and the 5' sense primer c-mplBglII [SEQ ID NO:24] were added to the reaction. The c-mplBglII [SEQ ID NO:24] primer anneals to the 5' end of the coding sequence for the c-mpl ligand gene (bases #207–230) and encodes a BglII restriction enzyme site 5' to the initiator methionine codon. In (PCR#2), RT#2 served as the template and only the c-mplBglII [SEQ ID NO:24] primer was added.

2. 1–153 c-mpl ligand

For amplification of 1–153 amino acid c-mpl ligand gene fragments, PCR#2 served as the template for amplification with a combination of the following primers; c-mplNcoI [SEQ ID NO:25], c-mplHindIII [SEQ ID NO:26], Ecocmpl [SEQ ID NO:29]

In polymerase chain reaction #3 (PCR #3), for generation of a 1–153 c-mpl ligand with a translation termination codon following amino acid #153, the c-mplNcoI [SEQ ID NO:25] and c-mplHindIII [SEQ ID NO:26] primers were used. The c-mplNcoI primer [SEQ ID NO:25] anneals to the c-mpl ligand gene (bases #279–311) resulting in codon choice degeneracy so that the gene could be efficiently transcribed and translated in Escherichia coli (*E. coli*). Transcription and translation of foreign genes in *E. coli* is affected by codon choice at the 5' end of the gene, and *E. coli*-preferred codons (See Chen et al., *DNA*:365–374 [1982]) usually lead to higher levels of expression. By providing multiple choices in codon sequence, multiple clones can be screened for high level expression. The NcoI restriction enzyme site added to the 5' end of the gene codes for methionine and alanine codons prior to the serine which is referred here as c-mpl ligand amino acid #1. The c-mplHindIII [SEQ ID NO:26] adds both a termination codon and a HindIII restriction enzyme site immediately following the final codon, arginine, which is referred to herein as amino acid #153. In polymerase chain reaction #4 (PCR#4), for generation of a 1–153 c-mpl ligand without a termination codon following amino acid #153, the c-mplNcoI [SEQ ID NO:25] and Ecocmpl [SEQ ID NO:29] primers were used with PCR#2 as the template. The Ecocmpl [SEQ ID NO:29] primer encodes a EcoRI site (GAATTC) in-frame with the c-mpl ligand gene, which create a glutamate and phenylalanine codons. These PCR reactions were designed so that the product resulted in the sequence from bases #279–737, encoding amino acids #1–153, which could be transferred into multiple expression systems.

EXAMPLE 2

BHK expression plasmid for 1–332 c-mpl ligand gene products

The full length c-mpl ligand PCR products (PCR#1 and PCR#2) were digested with BglII and EcoRI restriction enzymes and combined for transfer to a mammalian expression vector. The expression vector, pMON3976, was digested with BamHI and EcoRI (ca. 3750 bp), which allowed it to accept the BglII-EcoRI PCR fragments (ca. 1050 bp). pMON3976 is a derivative of pMON3359 which is a pUC18-based vector containing a mammalian expression cassette. The cassette includes the herpes simplex viral promoter IE110 (–800 to +120) and a SV40 late poly-adenylation (poly-A) signal subcloned into the pUC18 polylinker (See Hippenmeyer et al., Bio/Technology:1037–1041 [1993]). The original EcoRI site 5' to the promoter had been removed and a new EcoRI site added 3' to the BamHI site. These unique restriction enzyme sites are located between the promoter and poly-A signal to facilitate subcloning DNA fragments as BamHI-EcoRI or BglII-EcoRI fragments in a 5' to 3' direction for transcription and translation. The BglII site (5' end of the gene) is destroyed when ligated to the BamHI site of the vector. Plasmid DNA was prepared from individual clones and the c-mpl ligand insert portion were sequenced. One of the clones identified, pMON26451-3, encodes amino acids 1–332 c-mpl ligand with a deletion of amino acids #112–115. The plasmid, pMON26451-3, contains the DNA sequence [SEQ ID NO:39] which encodes the polypeptide represented by [SEQ ID NO:37]. One of the clones identified, pMON26451-1, encodes amino acids 1–332 c-mpl ligand with a amino acid substitution K(122)E. The plasmid, pMON26451-1, contains the DNA sequence [SEQ ID NO:59] which encodes the polypeptide represented by [SEQ ID NO:66]. One of the clones identified, pMON26451-4, encodes amino acids 1–332 c-mpl ligand with two amino acid substitutions P(46)L and W(200)R. The plasmid, pMON26451-4, contains the DNA sequence [SEQ ID NO:60] which encodes the polypeptide represented by [SEQ ID NO:67].

EXAMPLE 3

BHK expression plasmid for 1–153 c-mpl ligand gene products

The 1–153 c-mpl ligand PCR product (PCR#3) was digested with NcoI and HindIII restriction enzymes (ca. 460 bp) for transfer to a mammalian expression vector. The expression vector, pMON3934, was digested with NcoI and HindIII (ca. 3800 bp). pMON3934 is a derivative of pMON3359 which is a pUC18-based vector containing a mammalian expression cassette. The cassette includes the herpes simplex viral promoter IE110 (–800 to +120), a modified human IL-3 signal peptide sequence and a SV40 late poly-adenylation (poly-A) signal subcloned into the pUC18 polylinker (See Hippenmeyer et al., Bio/Technology:1037–1041 [1993]). The human IL-3 signal peptide sequence, which had been subcloned as a BamHI fragment into the unique BamHI site between the IE110 promoter and poly-A signal, contains an NcoI site at its 3' end followed by a HindIII site. This cloning also leaves a BamHI site 5' to the signal peptide and another BamHI site 3' to the HindIII site. When an NcoI-HindIII fragment is subcloned into pMON3934, the DNA sequence between the NcoI and HindIII sites is lost. This expression cassette is useful for secretion of proteins outside the cell. The DNA sequence of the signal peptide is shown below (restriction enzyme sites are indicated above). The ATG (methionine) codon within the NcoI site is in-frame with the initiator ATG of the signal peptide (underlined);

```
            BamHI                                                              NcoI
5'GGATCCACCATGAGCCGCCTGCCCGTCCTGCTCCTGCTCCAACTCCTGGTCCGCCCCGCCATGG     [SEQ ID NO:27]

MetSerArgLeuProValLeuLeuLeuLeuGlnLeuLeuValArgProAlaMet      [Seq ID NO:28]
```

Plasmid DNA was prepared from individual clones and the c-mpl ligand insert portion were sequenced. One of the clones identified, pMON26448, encodes amino acids 1–153 c-mpl ligand. The plasmid, pMON26448, contains the DNA sequence [SEQ ID NO:58] which encodes the polypeptide represented by [SEQ ID NO:65]. One of the clones identified, pMON26450, encodes amino acids 1–153 c-mpl ligand with a deletion of amino acids #112–115. The plasmid, pMON26450, contains the DNA sequence [SEQ ID NO:40] which encodes the polypeptide represented by [SEQ ID NO:38].

EXAMPLE 4

E. coli expression plasmid for 1–153 Δ112–115 c-mpl ligand gene product

The 1–153 c-mpl ligand PCR products (PCR#3) were digested with NcoI and HindIII restriction enzymes (ca. 460 bp) for transfer to an E. coli expression vector, pMON3935, digested with NcoI and HindIII (ca. 3250 bp). pMON3935 directs high-level production of heterologous proteins in the cytoplasm. The expression cassette of pMON3935 consists of the recA promoter and T7 gene 10 ribosome binding site (RBS) described elsewhere (Olins et al., Methods Enzym., 185: 115–119 [1988]) as well as a tandem inverted repeat of a phage P22 gene which functions as a transcription terminator. The cassette is on a plasmid that contains the pBR327 origin of replication and a gene that encodes for spectinomycin resistance. The NcoI restriction enzyme site follows the gene 10 RBS, and the HindIII restriction enzyme site is located between the NcoI site and the P22 terminator. Several different clones were screened for expression of a unique 17 Kd protein via SDS-PAGE as described earlier. pMON26453, encoding amino acids 1–153 c-mpl ligand with a deletion of amino acids #112–115, is a result of this cloning event. The plasmid, pMON26453, contains the DNA sequence [SEQ ID NO:49] which encodes the polypeptide represented by [SEQ ID NO:38].

EXAMPLE 5

Baculovirus expression plasmid for 1–153 c-mpl ligand/mouse Fc

The 1–153 c-mpl ligand PCR product (PCR#4) was digested with NcoI and EcoRI restriction enzymes (ca. 460 bp) for transfer to a Baculovirus expression vector. The expression vector, pMON26440, was digested with NcoI and EcoRI (ca. 10 Kb). pMON26440 is a derivative of pVL1393 (Invitrogen) containing a DNA sequence encoding a modified human IL-3 secretion signal peptide sequence (Example 3, above) and a DNA gene fragment encoding a modified mouse Fc (IgG2a) constant region and hinge region (Gross A. H., *J.Clin.Invest.* 95:2783–2789, [1995]). The DNA sequence, encoding the hIL-3 secretion signal peptide was subcloned into the BamHI site of the vector leaving the NcoI site at the 3' end of the signal sequence for cloning. The mouse Fc gene fragment (EcoRI-BglII) was subcloned into the BglII site of the vector such that the EcoRI site was available for cloning at the 5' end of the Fc. This facilitates cloning genes as NcoI-EcoRI fragments into the vector. A termination codon is introduced in-frame between the gene of interest and the EcoRI site. The EcoRI site (GAATTC) is added directly 3' to the gene of interest such that it encodes glutamate (GAA) and phenylalanine (TTC) codons. Following the EcoRI site is a DNA sequence encoding a Factor Xa proteolytic cleavage site, a small polypeptide linker region which is followed by the mouse Fc gene fragment. Plasmid DNA was prepared from individual clones and the c-mpl ligand insert portion were sequenced. pMON26454-4, encoding a chimera protein consisting of 1–153 Δ#112–115 c-mpl ligand joined to a mouse Fc, is a result of this cloning event. The plasmid, pMON26454-4, contains the DNA sequence [SEQ ID NO:50] which encodes the polypeptide represented by [SEQ ID NO:41]. pMON26454-8, encoding a chimera protein consisting of amino acids 1–153 c-mpl ligand joined to a mouse Fc, is also a result of this cloning event. The plasmid, pMON26454-8, contains the DNA sequence [SEQ ID NO:61] which encodes the polypeptide represented by [SEQ ID NO:68].

EXAMPLE 6

BHK expression plasmid for 1–153 c-mtl ligand Δ112–115/mouse Fc

In order to create a BHK plasmid for expression of 1–153 c-mpl ligand Δ112–115/mouse Fc, the NcoI-PstI fragment (ca. 310 bp) of pMON26448 was combined with the PstI-EcoRI fragment (ca. 150 bp) of pMoN26454-4 for ligation to the NcoI-EcoRI vector fragment of pMON3993 (ca. 4550 bp.). pMON3993 is a derivative of pMON3934 (above) and contains a modified mouse Fc gene fragment. An EcoRI-BglII mouse Fc gene fragment was transferred into the vector 3' to the NcoI site, leaving an EcoRI site between the NcoI site and the mouse Fc gene. An EcoRI site else-where in the vector had previously been destroyed. This facilitates cloning genes as NcoI-EcoRI fragments into the vector and fuses the gene of interest in-frame to the mouse Fc. A termination codon was introduced in-frame between the gene of interest and the EcoRI site. The EcoRI site (GAATTC) is added directly 3' to the gene of interest such that it encodes glutamate (GAA) and phenylalanine (TTC) codons. pMON26465, encoding amino acids 1–153 Δ112–115 c-mpl ligand joined to a mouse Fc, is a result of this cloning. The plasmid, pMON26465, contains the DNA sequence [SEQ ID NO:51] which encodes the polypeptide represented by [SEQ ID NO:42].

EXAMPLE 7

BHK expression plasmid for 1–153 c-mul ligand Δ112–115

A second BHK expression plasmid encoding amino acids 1–153 Δ112–115 c-mpl ligand was constructed in which the DNA sequence at the 5' end of the 1–153 Δ112–115 c-mpl ligand gene was changed, without altering the resulting amino acid sequence, to optimize protein expression which might result in increased secretion of the protein. This plasmid, pMON30214, was constructed by ligating the NcoI-BamHI fragment of pMON26465 (ca. 370 bp), the BamHI-HindIII fragment of pMON26448 (ca. 90 bp) and the NcoI-HindIII fragment of pMON3934 (ca. 3800 bp). Plasmid DNA was prepared from individual clones and the c-mpl ligand insert portion were sequenced. The plasmid, pMON30214, contains the DNA sequence [SEQ ID NO:48] which encodes the polypeptide represented by [SEQ ID NO:38].

EXAMPLE 8

*E. coli* expression plasmid for 1–153 c-mpl ligand/ glyser/IL-3 variant 13288 pMON26461, encoding the chimera protein, 1–153 c-mpl ligand/glyser/IL-3 variant 13288 (WO 94/12638), was constructed by ligating the NcoI-EcoRI fragment of pMON26454-8 (ca. 460 bp.) and a synthetic linker (EcoSna1 [SEQ ID NO:30], EcoSna2 [SEQ ID NO:31]) to the SnaBI-NcoI vector fragment (ca. 3500 bp.) of pMON13057 [WO 9 5/21254]. The plasmid, pMON26461, contains the DNA sequence [SEQ ID NO:72] which encodes the polypeptide represented by [SEQ ID NO:73].

EXAMPLE 9

BHK expression vector for 1–153 c-mpl ligand/ FXa/gl vser/IL-3 variant 13288 pMON26474, encoding the chimera protein, 1–153 c-mpl ligand/FXa/glyser/IL-3 variant 13288, was constructed by ligating the NcoI-HindIII fragment of pMON26472 (ca. 860 bp.) to the NcoI-HindIII fragment of pMON3934 (ca. 3800). pMON26472, an *E. coli* expression plasmid for amino acids 1–153 c-mpl ligand/FXa/glyser/IL-3 variant 13288 , was constructed by combining the NcoI-SnaBI fragment of pMON26461 (ca. 460 bp.) and the SnaBI-HindIII fragment of pMON3988 (ca. 400 bp.) (WO 95/21254) for ligation to the NcoI-HindIII vector fragment of pMON3935 (ca. 3250 bp.). The plasmid, pMON26474, contains the DNA sequence [SEQ ID NO:64] which encodes the polypeptide represented by [SEQ ID NO:71].

EXAMPLE 10

BHK expression plasmid for 1–153 Δ112–115 c-mpl ligand/FXa/glyser/IL-3 variant 13288 pMON26469, encoding the chimera protein, 1–153 Δ#112–115 c-mpl ligand joined to IL-3 variant 13288, was constructed. The NcoI-BamHI fragment from pMON26454-4 (ca. 370 bp) was combined with the BamHI-HindIII fragment of pMON26474 (ca. 490 bp) and the NcoI-HindIII vector fragment of pMON3934 (ca. 3800 bp). The plasmid, pMON26469, contains the DNA sequence [SEQ ID NO:52] which encodes the polypeptide represented by [SEQ ID NO:43].

EXAMPLE 11

BHK expression plasmid for 1–153 Δ112–115 c-mpl ligand/IL-3 variant 13288 chimera pMON30243, encoding the chimera protein, 1–153 Δ112–115 c-mpl ligand joined to IL-3 variant 13288, was constructed by combining the NcoI-SnaBI fragment of pMON26469 (ca. 460 bp) with the SnaBI-HindIII fragment (ca. 400 bp) of pMON26427 (WO 95/21254) and ligating to the NcoI-HindIII fragment (ca. 3800 bp) of pMON3934. The plasmid, pMON30243, contains the DNA sequence [SEQ ID NO:53] which encodes the polypeptide represented by [SEQ ID NO:44].

EXAMPLE 12

E. coli expression plasmid for IL-3 variant 13288/ FXa/glyser/1–153 c-mil ligand pMON26460, an E. coli expression plasmid for production of the chimera protein, IL-3 variant 13288/Fxa/glyser/ amino acids 1–153 c-mpl ligand, was constructed by ligating the NcoI-HindIII fragment of pMON26448 (ca. 460 bp.) to the AflIII-HindIII vector fragment (ca. 3500 bp) of pMON13018 (WO 95/21254). The plasmid, pMON26460, contains the DNA sequence [SEQ ID No:62] which encodes the polypeptide represented by [SEQ ID NO:69].

EXAMPLE 13

E. coli expression plasmid for IL-3 variant 13288/ glyser/1–153 c-mpl ligand pMON26471, an E. coli expression plasmid for the production of the chimera protein, IL-3 variant 13288/glyser/ 1–153 c-mpl ligand, was constructed by ligating the NcoI-SmaI fragment of pMON26426 (ca. 370 bp.) to the SmaI-HindIII fragment of pMON26460 (ca. 490 bp) into the NcoI-HindIII vector fragment of pMON3935 (3250 bp.). pMON26426 was constructed by transferring the NcoI-HindIII fragment (ca. 950 bp.) of pMON13056 (WO 95/21254) to the NcoI-HindIII vector fragment (ca. 3800 bp.) of pMON3934 (ca. 3800 bp.). The plasmid, pMON26471, contains the DNA sequence [SEQ ID NO:63] which encodes the poly-peptide represented by [SEQ ID NO:70].

EXAMPLE 14

BHK expression plasmid for IL-3 variant 13288/ glyser/1–153 Δ112–115 c-mpl ligand pMON26272, expressing IL-3 variant 13288 joined via a glycine-serine linker to amino acids 1–153 Δ112–115 c-mpl ligand, was constructed by combining the NcoI-PstI fragment of pMON26473 (ca. 700 bp) with the PstI-HindIII fragment of pMON30214 (ca. 160 bp) and ligating to the NcoI-HindIII fragment of pMON3934 (ca. 3800 bp). pMON26473 was constructed by ligating the NcoI-HindIII fragment of pMON26471 (ca. 880 bp.) to the NcoI-HindIII vector fragment of pMON3934 (ca. 3800 bp.). The plasmid, pMON30272, contains the DNA sequence [SEQ ID NO:54] which encodes the polypeptide represented by [SEQ ID NO:45].

EXAMPLE 15

BHK expression plasmid for 1–153 Δ112–115/his$_6$ c-mpl ligand pMON30253, expressing 1–153 Δ112–115/his6 c-mpl ligand, was constructed by digesting pMON26465 with ECORI and ligation of a synthetic linker that adds a C-terminal poly-histidine tag. The linker was constructed by annealing the HisC1 [SEQ ID NO:32] and HisC2 [SEQ ID NO:33] primers which creates a GluPheHisHisHisHisHisHis [SEQ ID NO:57] tail immediately following the c-mpl ligand molecule. A termination codon following the last His codon prevents translation beyond that point. The DNA was sequenced to confirm orientation of the linker which keeps a unique EcoRI site immediately 3' to the c-mpl ligand gene and 5' to the poly-histidine tail. The plasmid, pMON30253, contains the DNA sequence [SEQ ID NO:55] which encodes the polypeptide represented by [SEQ ID NO:46].

EXAMPLE 16

BHK expression plasmid for his$_6$/1–153 Δ112–115 c-mpl ligand pMON30274, expressing his$_6$/1–153 Δ112–115 c-mpl ligand, was constructed by digesting pMON30214 with NcoI and ligation of a synthetic linker that adds an N-terminal poly-histidine tag. The linker was constructed by annealing the HisN1 [SEQ ID NO:34] and HisN2 [SEQ ID NO:35] primers which creates a HisHisHisHisHisHisAla-MetAla [SEQ ID NO:36] tag immediately proceeding the c-mpl ligand molecule. The DNA was sequenced to confirm the orientation of the linker which keeps a unique NcoI site 3' to the tag and 5' to the c-mpl ligand gene. The plasmid, pMON30274, contains the DNA sequence [SEQ ID NO:56] which encodes the polypeptide represented by [SEQ ID NO:47].

EXAMPLE 17

Assembling genes from previous examples

A variety of different of c-mpl ligand genes can be assembled from Examples 1 through 6 by combining various gene fragments via restriction enzyme digestion and ligation (see Sambrook et al., *Molecular Cloning: A Laboratory Manual*, 2nd ed., Cold Spring Harbor Laboratory Press, Cold Spring Harbor, N.Y., [1989]). The genes from the examples can be digested with restriction enzymes on either end of the gene as well as internally to release desired gene fragments. Then, the different pieces can be ligated together and to an expression vector through complementary ends using DNA ligase. The ligated DNA can be transformed into E. coli and colonies are screened for the desired gene product through DNA sequencing of plasmid DNA. After identification of positive clones, the plasmid DNA can be transfected into an appropriate mammalian cell or E. coli strain for production.

EXAMPLE 18

Site-directed mutagenesis

A variety of amino acid substitutions can be made at each position using either synthetic gene assembly or site-directed mutagenesis (see Taylor et al., *Nucl. Acids Res.*, 13: 7864–8785 [1985]; Kunkel et al., *Proc. Natl. Acad. Sci. USA*, 82: 488–492 [1985]; Sambrook et al., *Molecular Cloning: A Laboratory Manual*, 2nd ed., Cold Spring Harbor Laboratory Press, Cold Spring Harbor, N.Y., [1989], (WO 94/12639) and (WO 94/12638)). These substitutions can be made one at a time or in combination with other amino acid substitutions. After sequence verification of the changes, the plasmid DNA can be transfected into an appropriate mammalian cell or *E. coli* strain for production.

EXAMPLE 19

SDS Folding Protocol For c-mpl Chimera Proteins

A. Recovery of c-mpl chimera protein from inclusion bodies.

*E. coli* cells from a 300 ml culture expressing the chimera protein are resuspended in 150 mls of 20 mM Tris-HCl, 5 mM EDTA, pH 8.0. The cell resuspension is sonicated by standard means for ~3 minutes on ice, and then centrifuged at 5,000×g for 30 minutes. The recovered inclusion body (IB) pellet is washed 2×by resuspending in 150 mls of 20 mM Tris-HCl, 1 mM EDTA, pH 8.0, sonicating as above, and centrifuging at 5000×g for 30 minutes. The washed IB pellet can be used immediately or stored at—70° C. A Manton-Gaulin homogenizer can also be used to disrupt larger quantities of cells when processing IB material in a similar manner at a larger scale.

B. Solubilization and refold of monomeric c-mpl ligand Chimera Protein.

The washed IB pellet is resuspended in 100 mM Tris-HCl, pH 9.0(pH 8.0–9.75 suitable) containing 0.1% (w/v) sodium dodecyl sulfate (SDS) at a ratio of 50 mls per ~1 gm of cell pellet using a hand tissue homogenizer. Dilute suspension to 200 mls in same buffer and stir at 4° C. until completely mixed (5–15 minutes). Dithiothreitol (DTT) is added to a final conc. of 20 mM and L-cysteine (Sigma #4820) to a final conc. of 1 mM (DTT added from a fresh 50×stock, and cysteine added from a fresh 100×stock; stocks prepared in 100 mM Tris-HCl pH 9.00). The refold solution is air oxidized at 4° C. (4° C. to 25° C. suitable) with moderate stirring in a loosely covered container (18–72 hrs). Refold is monitored by rHPLC analysis to determine completion.

EXAMPLE 20

Determination of bioactivity of c-mpl ligands and chimera molecules pMON26448 (1–332 c-mpl ligand) and hIL-3 variant, pMON13288 (WO 94/12638), are used as activity reference standards in the following assays.

1. TF1 proliferation assay c-mpl ligand proliferative activity is assayed using a subclone of the pluripotential human cell line TF1 (Kitamura et al., *J. Cell Physiol* 140:323–334. [1989]). TF1 cells are maintained in h-IL3 (100 U/mL). To establish a sub-clone responsive to c-mpl ligand, cells are maintained in passage media containing 10% supernatant from BHK cells transfected with the gene expressing the 1–153 form of c-mpl ligand (pMON26448). Most of the cells die, but a subset of cells survive. After dilution cloning, a c-mpl ligand responsive clone is selected, and these cells are split into passage media to a density of $0.3 \times 10^6$ cells/mL the day prior to assay set-up. Passage media for these cells is the following: RPMI 1640 (Gibco), 10% FBS (Harlan, Lot #91206), 10% c-mpl ligand supernatant from transfected BHK cells, 1 mM sodium pyruvate (Gibco), 2 mM glutamine (Gibco), and 100 ug/mL penicillin-streptomycin (Gibco). The next day, cells are harvested and washed twice in RPMI or IMDM media with a final wash in the ATL, or assay media. ATL media consists of the following:IMDM (Gibco), 500 ug/mL of bovine serum albumin, 100 ug/mL of human transferrin, 50 ug/mL soybean lipids, $4 \times 10^{-8}$M beta-mercaptoethanol and 2 mL of A9909 (Sigma, antibiotic solution) per 1000 mL of ATL. Cells are diluted in assay media to a final density of $0.25 \times 10^6$ cells/mL in a 96-well low evaporation plate (Costar) to a final volume of 50 ul. Transient supernatants (conditioned media) from transfected clones are added at a volume of 50 ul as duplicate samples at a final concentration of 50% and diluted three-fold to a final dilution of 1.8%. Triplicate samples of a dose curve of IL-3 variant pMON13288 starting at 1 ng/mL and diluted using three-fold dilutions to 0.0014 ng/mL is included as a positive control. Plates are incubated at 5% $CO_2$ and 37° C. At day six of culture, the plate is pulsed with 0.5 Ci of $^3$H/well (NEN) in a volume of 20 ul/well and allowed to incubate at 5% $CO_2$ and 37° C., for four hours. The plate is harvested and counted on a Betaplate counter.

TABLE 1

TF1 Proliferation Assay

| transfection pMON # | c-mpl ligand | TOTAL COUNTS tritiated thymidine incorporation 10% supernatants | Standard Deviation |
|---|---|---|---|
| mock | | 21910 | 561 |
| pMON26448 | 1–153 | 114888 | 5269 |
| pMON26450 | 1–153 Δ112–115 | 60827 | 1741 |
| pMON26451-1 | 1–332 Glu$^{122}$ | 133722 | 10040 |
| pMON26451-3 | 1–332 Δ112–115 | 35600 | 3627 |
| pMON26451-4 | 1–332 Leu$^{46}$,Arg$^{200}$ | 121684 | 2611 |

Table 1. The c-mpl ligands listed above were tested in the TF1 proliferation assay. All of the c-mpl ligands tested were active in this assay.

Other in vitro cell based assays may also be useful to determine the activity of the c-mpl ligands or chimera molecules depending on the colony stimulating factors that comprise the chimera. The following are examples of other useful assays. In addition blocking monoclonal antibodies, raised against one of the components of a chimera, can be used in a cell proliferation assay to determine that each component of a chimera is active.

32D proliferation assay: 32D is a murine IL-3 dependent cell line which does not respond to human IL-3 but does respond to human G-CSF which is not species restricted.

Baf/3 proliferation assay: Baf/3 is a murine IL-3 dependent cell line which does not respond to human IL-3 or human c-mpl ligand but does respond to human G-CSF which is not species restricted.

T1165 proliferation assay: T1165 cells are a IL-6 dependent murine cell line (Nordan et al., 1986) which respond to IL-6 and IL-11.

AML193 proliferation assay: This cell line, established from a patient with acute myelogenous leukemia, is a growth factor dependent cell line which displayed enhanced growth in GM-CSF supplemented medium (Lange, B., et al., (1987); Valtieri, M., et al., (1987). The AML cell line also responds to human IL-3 and G-CSF.

Transfected cell lines: Cell lines such as Baf/3 cell line can be transfected with a colony stimulating factor receptor, such as the human IL-3 receptor or human c-mpl receptor, which the cell line does not have. These transfected cell lines can be used to determine the activity of the ligand for which the receptor has been transfected into the cell line.

One such transfected Baf/3 cell line was made by cloning the cDNA encoding c-mpl from a library made from a c-mpl responsive cell line and cloned into the multiple cloning site of the plasmid pcDwA3 (Invitrogen, San Diego Calif.). Baf/3 cells were transfected with the plasmid via electroporation. The cells were grown under G418 selection in the presence of mouse IL-3 in Wehi conditioned media. Clones were established through limited dilution.

TABLE 2

AML and TF1 Proliferation Assay of c-mpl ligand/Fc chimera

| factor | Baf/3-cmpl-R Cells tested at 1 μg/ml | TF1.2.B4 Cells tested at 2 μg/ml |
|---|---|---|
| pMON26465 | 10470 +/− 700 | 4400 +/− 110 |
| pMON26458 | 25000 +/− 580 | 20300 +/− 1200 |
| CTLA-4 mFc control | 1020 +/− 120 | 580 +/− 260 |

Table 2. pMON26465 and pMON26458 were assayed for proliferative activity in both Baf/3 cells transfected with the human c-mpl-R (Baf/3-cmpl-R) and in the TF1.2.B4 cell line. Cells were pulsed with 1 μCi/well of tritiated thymidine for overnight (Baf/3-cmpl-R cells) or for 4 hours (TF1.2.B4 cells) and total counts cpm (3H) determined on a beta plate counter.

2. Bone marrow Proliferation assay a. CD34+ Cell Purification:

Between 15–20 mL bone marrow aspirates are obtained from normal allogeneic marrow donors after informed consent. Cells are diluted 1:3 in phosphate buffered saline (PBS, Gibco-BRL), 30 mL are layered over 15 mL Histopaque-1077 (Sigma) and centrifuged for 30 minutes at 300 RCF. The mononuclear interface layer is collected and washed in PBS. CD34+ cells are enriched from the mononuclear cell preparation using an affinity column per manufacturers instructions (CellPro, Inc, Bothell Wash.). After enrichment, the purity of CD34+ cells is 70% on average as determined by using flow cytometric analysis using anti-CD34 monoclonal antibody conjugated to fluorescein and anti-CD38 conjugated to phycoerythrin (Becton Dickinson, San Jose Calif.).

Cells are resuspended at 40,000 cells/mL in X-Vivo 10 media (Bio-Whittaker, Walkersville, Md.) and 1 mL is plated in 12-well tissue culture plates (Costar). Human IL-3 variant, pMON13288, is used at 10 ng/mL or 100 ng/mL. Conditioned media from BHK cells transfected with plasmid encoding c-mpl ligand are tested by addition of 100 μl of supernatant added to 1 mL cultures (approximately a 10% dilution). Cells are incubated at 37° C. for 8–14 days at 5% $CO_2$ in a 37° C. humidified incubator.

b. Cell Harvest and Analysis:

At the end of the culture period a total cell count is obtained for each condition. For fluorescence analysis and ploidy determination cells, are washed in megakaryocyte buffer (MK buffer, 13.6 mM Sodium Citrate, 1 mM Theophylline, 2.2 μm PGE1, 11 mM Glucose, 3% W/V BSA, in PBS, pH 7.4,) (Tomer et al., *Blood* 70(6): 1735–42 [1987]) resuspended in 500 μl of MK buffer containing anti-CD41a FITC antibody (1:200, AMAC, Westbrook, Me.) and washed in MK buffer. For DNA analysis cells are made permeable in MK buffer containing 0.5% Tween 20 (Fisher, Fair Lawn N.J.) for 20 minutes on ice followed by fixation in 0.5% Tween-20 and 1% paraformaldehyde (Fisher Chemical) for 30 minutes followed by incubation in Propidium Iodide (Calbiochem, La Jolla Calif.) (50 μg/mL) with RNAase (400 U/mL) in 55% v/v MK buffer (200 mOsm) for 1–2 hours on ice. Cells are analyzed on a FACScan or Vantage flow cytometer (Becton Dickinson, San Jose, Calif.). Green fluorescence (CD41a-FITC) is collected along with linear and log signals for red fluorescence (PI) to determine DNA ploidy. All cells are collected to determine the percent of cells that are CD41+. Data analysis is performed using LYSIS software (Becton Dickinson, San Jose, Calif.). Percent of cells expressing the CD41 antigen is obtained from flow cytometry analysis (Percent). Absolute (Abs) number of CD41+ cells/mL is calculated by: (Abs)= (Cell Count)*(Percent)/100.

TABLE 3

Bone Marrow Proliferation Assay
Proliferation of CD34 + enriched
cells in the presence of c-mpl ligand variants

| Transfection Construct | c-mpl ligand | Cells/Well after 10 Day Culture (4000 cells plated) |
|---|---|---|
| Mock Control | | <500 |
| pMON26448 | 1-153 | 22,500 |
| pMON26450 | 1-153 Δ112–115 | <500 |
| pMON26451-3 | 1-332 Glu$^{122}$ | <500 |
| pMON26451-4 | 1-332 leu$^{46}$, Arg$^{200}$ | 16,000 |

Table 3. The c-mpl ligands listed above were tested in the megakaryocyte liquid culture assay. pMON26448 and pMON26451-4 were active in this assay.

TABLE 4

Megakaryocyte liquid culture assay
Absolute number of CD41 + cells
after 10 days in culture in the presence or absence of IL-3 pMON13288

| Transfection Construct | c-mpl ligand | No pMON13288 | pMON13288 10 ng/mL |
|---|---|---|---|
| Mock Control | | <500 | 3000 |
| pMON26448 | 1-153 | 19,000 | 45,000 |
| pMON26450 | 1-153 Δ112–115 | <500 | 8,500 |
| pMON26451-3 | 1-332 Glu$^{122}$ | <500 | 9,000 |
| pMON26451-4 | 1-332 leu$^{46}$, Arg$^{200}$ | 12,500 | 16,000 |

Table 4. The c-mpl ligands listed above were tested in the megakaryocyte liquid culture assay as described above. pMON26450 and pMON26451-3 were not active by themselves but were active when co-administered with the human IL3 receptor agonist, pMON13288, over and above pMON13288 by itself.

3. Megakaryocyte fibrin clot assay.

CD34+ enriched population are isolated as described above. Cells are suspended at 25,000 cells/mL with/without cytokine(s) in a media consisting of a base Iscoves IMDM media supplemented with 0.3% BSA, 0.4 mg/mL apotransferrin, 6.67 μM $FeCl_2$, 25 μg/mL $CaCl_2$, 25 μg/mL L-asparagine, 500 μg/mL E-amino-n-caproic acid and Penicillin/Streptomycin. Prior to plating into 35 mm plates, thrombin is added (0.25 units/mL) to initiate clot formation. Cells are incubated at 37° C. for 13 days at 5% $CO_2$ in a 37° C. humidified incubator. At the end of the culture period plates are fixed with methanol:acetone (1:3), air dried and stored at −200C until staining. A peroxidase immunocytochemistry staining procedure is used (Zymed, Histostain-SP. San Francisco, Calif.) using a cocktail of primary monoclonal antibodies consisting of anti-CD41a, CD42 and CD61. Colonies are counted after staining and classified as negative, CFU-MK (small colonies, 1–2 foci and less that approx. 25 cells), BFU-MK (large, multi-foci colonies with>25 cells) or mixed colonies (mixture of both positive and negative cells).

What is claimed is:

1. A chimera protein comprising the sequence (SEQ ID NO:44)

```
Ser Pro Ala Pro Pro Ala Cys Asp Leu Arg
1               5                   10

Val Leu Ser Lys Leu Leu Arg Asp Ser His
            15                  20

Val Leu His Ser Arg Leu Ser Gln Cys Pro
            25                  30

Glu Val His Pro Leu Pro Thr Pro Val Leu
            35                  40

Leu Pro Ala Val Asp Phe Ser Leu Gly Glu
            45                  50

Trp Lys Thr Gln Met Glu Glu Thr Lys Ala
            55                  60

Gln Asp Ile Leu Gly Ala Val Thr Leu Leu
            65                  70

Leu Glu Gly Val Met Ala Ala Arg Gly Gln
            75                  80

Leu Gly Pro Thr Cys Leu Ser Ser Leu Leu
            85                  90

Gly Gln Leu Ser Gly Gln Val Arg Leu Leu
            95                  100

Leu Gly Ala Leu Gln Ser Leu Leu Gly Thr
            105                 110

Gln Gly Arg Thr Thr Ala His Lys Asp Pro
            115                 120

Asn Ala Ile Phe Leu Ser Phe Gln His Leu
            125                 130

Leu Arg Gly Lys Val Arg Phe Leu Met Leu
            135                 140

Val Gly Gly Ser Thr Leu Cys Val Arg Glu
Phe His Ala Tyr Val Glu Gly Gly Gly Gly
            145                 150
                                155                 160

Ser Pro Gly Gly Gly Ser Gly Gly Gly Ser
            165                 170

Asn Met Ala Asn Cys Ser Ile Met Ile Asp
            175                 180

Glu Ile Ile His His Leu Lys Arg Pro Pro
            185                 190

Asn Pro Leu Leu Asp Pro Asn Asn Leu Asn
            195                 200

Ser Glu Asp Met Asp Ile Leu Met Glu Arg
            205                 210

Asn Leu Arg Thr Pro Asn Leu Leu Ala Phe
            215                 220

Val Arg Ala Val Lys His Leu Glu Asn Ala
            225                 230

Ser Gly Ile Glu Ala Ile Leu Arg Asn Leu
            235                 240

Gln Pro Cys Leu Pro Ser Ala Thr Ala Ala
            245                 250

Pro Ser Arg His Pro Ile Ile Ile Lys Ala
            255                 260

Gly Asp Trp Gln Glu Phe Arg Glu Lys Leu
            265                 270

Thr Phe Tyr Leu Val Thr Leu Glu Gln Ala
            275                 280

Gln Glu Gln Gln;
``` and said chimera protein is optionally immediately preceded by Met$^{-1}$, Ala$^{-1}$ or Met$^{-2}$ Ala$^{-1}$.

2. The chimera protein according to claim 1, having the amino acid sequence

```
Ser Pro Ala Pro Pro Ala Cys Asp Leu Arg Val Leu Ser Lys Leu Leu        (SEQ ID NO:44)
1               5                   10                  15

Arg Asp Ser His Val Leu His Ser Arg Leu Ser Gln Cys Pro Glu Val
                20                  25                  30

His Pro Leu Pro Thr Pro Val Leu Leu Pro Ala Val Asp Phe Ser Leu
            35                  40                  45

Gly Glu Trp Lys Thr Gln Met Glu Glu Thr Lys Ala Gln Asp Ile Leu
    50                  55                  60

Gly Ala Val Thr Leu Leu Leu Glu Gly Val Met Ala Ala Arg Gly Gln
65              70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Gly
            100                 105                 110

Arg Thr Thr Ala His Lys Asp Pro Asn Ala Ile Phe Leu Ser Phe Gln
        115                 120                 125

His Leu Leu Arg Gly Lys Val Arg Phe Leu Met Leu Val Gly Gly Ser
    130                 135                 140

Thr Leu Cys Val Arg Glu Phe His Ala Tyr Val Glu Gly Gly Gly Gly
145                 150                 155                 160

Ser Pro Gly Gly Gly Ser Gly Gly Ser Asn Met Ala Asn Cys Ser
                165                 170                 175

Ile Met Ile Asp Glu Ile Ile His His Leu Lys Arg Pro Pro Asn Pro
            180                 185                 190

Leu Leu Asp Pro Asn Asn Leu Asn Ser Glu Asp Met Asp Ile Leu Met
        195                 200                 205

Glu Arg Asn Leu Arg Thr Pro Asn Leu Leu Ala Phe Val Arg Ala Val
    210                 215                 220

Lys His Leu Glu Asn Ala Ser Gly Ile Glu Ala Ile Leu Arg Asn Leu
225                 230                 235                 240

Gln Pro Cys Leu Pro Ser Ala Thr Ala Ala Pro Ser Arg His Pro Ile
            245                 250                 255

Ile Ile Lys Ala Gly Asp Trp Gln Glu Phe Arg Glu Lys Leu Thr Phe
            260                 265                 270

Tyr Leu Val Thr Leu Glu Gln Ala Gln Glu Gln Gln.
        275                 280
```

3. A method of producing a chimeric protein comprising the steps of:
   (a) culturing a host cell containing a recombinant vector DNA comprising a DNA sequence that encodes the chimeric protein of claim 1, or 2 under conditions permitting expression of the chimeric protein; and
   (b) harvesting the chimeric protein.

4. The method of claim 3 wherein said DNA sequence is SEQ ID NO:53.

5. A method for selective ex vivo expansion of hematopoietic stem cells, comprising the steps of;
   (a) separating hematopoietic stem cells from other cells;
   (b) culturing said separated hematopoietic stem cells with a selected media which comprises; a chimeric protein of claim 1, or 2; and
   (c) harvesting said cultured cells.

6. A method for selective ex vivo expansion of hematopoietic stem cells, comprising the steps of;
   (a) removing hematopoietic stem cells from a patient;
   (b) separating hematopoietic stem cells from other cells;
   (c) culturing said separated hematopoietic stem cells with a selected media which comprises; a chimeric protein of claim 1, or 2; and
   (d) harvesting said cultured cells.

* * * * *